(12) United States Patent
Williams et al.

(10) Patent No.: US 10,952,772 B2
(45) Date of Patent: Mar. 23, 2021

(54) ACCESS DEVICE

(71) Applicant: Atropos Limited, County Wicklow (IE)

(72) Inventors: Stephen Williams, County Dublin (IE); Lucy Dolores Halpin, Dublin (IE); Shane Joseph MacNally, County Wicklow (IE); Frank Bonadio, County Wicklow (IE)

(73) Assignee: Atropos Limited, County Wicklow (IE)

( * ) Notice: Subject to any disclaimer, the term of this patent is extended or adjusted under 35 U.S.C. 154(b) by 88 days.

(21) Appl. No.: 15/637,586

(22) Filed: Jun. 29, 2017

(65) Prior Publication Data

US 2018/0036034 A1 Feb. 8, 2018

Related U.S. Application Data

(60) Provisional application No. 62/462,630, filed on Feb. 23, 2017.

(30) Foreign Application Priority Data

Jul. 4, 2016 (EP) .................................... 16177844

(51) Int. Cl.
*A61B 17/34* (2006.01)
*A61B 17/02* (2006.01)
*A61B 17/00* (2006.01)

(52) U.S. Cl.
CPC .......... *A61B 17/3498* (2013.01); *A61B 17/02* (2013.01); *A61B 17/0293* (2013.01); *A61B 17/3423* (2013.01); *A61B 17/3462* (2013.01); *A61B 2017/00265* (2013.01); *A61B 2017/00557* (2013.01); *A61B 2017/3466* (2013.01)

(58) Field of Classification Search
CPC . A61B 17/0218; A61B 17/0293; A61B 17/02; A61B 17/3498; A61B 2017/0225; A61B 2017/3464; A61B 17/3462; A61B 17/3439
See application file for complete search history.

(56) References Cited

U.S. PATENT DOCUMENTS

| 4,094,492 A | 6/1978 | Beeman et al. |
|---|---|---|
| 5,366,478 A | 11/1994 | Brinkerhoff et al. |
| 5,389,080 A * | 2/1995 | Yoon .................. A61B 17/3421 604/167.03 |

(Continued)

FOREIGN PATENT DOCUMENTS

| EP | 1816968 B1 | 3/2010 |
|---|---|---|
| WO | WO 0054677 A1 | 9/2000 |

(Continued)

*Primary Examiner* — Amy R Sipp
(74) *Attorney, Agent, or Firm* — Bookoff McAndrews, PLLC

(57) ABSTRACT

A surgical access sealing device comprises expansile chambers 306, 307, 308, 309 which define inflation spaces. An upper layer 304 in one case comprises two chambers 306, 307 which are overlapped when uninflated. A lower layer 305 comprises two chambers 308, 309 which are also overlapped, when uninflated. The region of overlap between the chambers 306, 307 of the first layer is offset from the region of overlap between the chambers 308, 309 of the second layer. The walls of the inflated chambers are movable for passage of an object such as a surgeon's arm/hand whilst maintaining a seal.

18 Claims, 48 Drawing Sheets

(56) References Cited

U.S. PATENT DOCUMENTS

| | | | |
|---|---|---|---|
| 5,480,410 A | 1/1996 | Cuschieri et al. | |
| 5,514,133 A | 5/1996 | Golub et al. | |
| 5,522,791 A | 6/1996 | Leyva | |
| 5,524,644 A | 6/1996 | Crook | |
| 5,526,536 A | 6/1996 | Cartmill | |
| 5,636,645 A | 6/1997 | Ou | |
| 5,640,977 A | 6/1997 | Leahy et al. | |
| 5,649,550 A | 7/1997 | Crook | |
| 5,653,705 A | 8/1997 | de la Torre et al. | |
| 5,672,168 A | 9/1997 | de la Torre et al. | |
| 5,741,298 A | 4/1998 | MacLeod | |
| 5,803,921 A | 9/1998 | Bonadio | |
| 5,813,409 A | 9/1998 | Leahy et al. | |
| 5,853,395 A | 12/1998 | Crook et al. | |
| 5,899,208 A | 5/1999 | Bonadio | |
| 5,906,577 A | 5/1999 | Beane et al. | |
| 5,957,913 A | 9/1999 | de la Torre et al. | |
| 5,997,515 A * | 12/1999 | de la Torre | A61B 17/3417 604/246 |
| 6,033,426 A | 5/2000 | Kaji | |
| 6,042,573 A | 5/2000 | Lucey | |
| 6,110,154 A | 8/2000 | Shimomura et al. | |
| 6,142,936 A | 11/2000 | Beane et al. | |
| 6,149,642 A | 11/2000 | Gerhart et al. | |
| 6,254,534 B1 | 7/2001 | Butler et al. | |
| 6,578,577 B2 | 6/2003 | Bonadio et al. | |
| 6,582,364 B2 | 6/2003 | Butler et al. | |
| 6,623,426 B2 | 9/2003 | Bonadio et al. | |
| 6,846,287 B2 | 1/2005 | Bonadio et al. | |
| 6,908,430 B2 | 1/2005 | Caldwell et al. | |
| 6,958,037 B2 | 10/2005 | Ewers et al. | |
| 7,008,377 B2 | 3/2006 | Beane et al. | |
| 7,052,454 B2 | 5/2006 | Taylor | |
| 7,081,089 B2 | 7/2006 | Bonadio et al. | |
| 7,163,510 B2 | 1/2007 | Kahle et al. | |
| 7,195,590 B2 | 3/2007 | Butler et al. | |
| 7,214,185 B1 | 5/2007 | Rosney et al. | |
| 7,238,154 B2 | 7/2007 | Ewers et al. | |
| 7,300,399 B2 | 11/2007 | Bonadio et al. | |
| 7,445,597 B2 | 11/2008 | Butler et al. | |
| 7,473,221 B2 | 1/2009 | Ewers et al. | |
| 7,481,765 B2 | 1/2009 | Ewers et al. | |
| 7,559,893 B2 | 7/2009 | Bonadio et al. | |
| 7,650,887 B2 | 1/2010 | Nguyen et al. | |
| 7,749,161 B2 | 7/2010 | Beckman et al. | |
| 7,998,068 B2 | 8/2011 | Bonadio et al. | |
| 8,012,088 B2 | 9/2011 | Butler et al. | |
| 8,016,755 B2 | 9/2011 | Ewers et al. | |
| 8,021,296 B2 | 9/2011 | Bonadio et al. | |
| 8,070,676 B2 | 12/2011 | Ewers et al. | |
| 8,105,234 B2 | 1/2012 | Ewers et al. | |
| 8,109,873 B2 | 2/2012 | Albrecht et al. | |
| 8,187,177 B2 | 5/2012 | Kahle et al. | |
| 8,187,178 B2 | 5/2012 | Bonadio et al. | |
| 8,317,691 B2 | 11/2012 | Bonadio et al. | |
| 8,465,494 B2 | 6/2013 | Butler et al. | |
| 8,657,740 B2 | 2/2014 | Bonadio et al. | |
| 8,672,839 B2 | 3/2014 | Ewers et al. | |
| 8,696,557 B2 | 4/2014 | Fischvogt | |
| 8,752,553 B2 | 6/2014 | Bonadio et al. | |
| 8,911,366 B2 | 12/2014 | Ewers et al. | |
| 8,986,202 B2 | 3/2015 | Butler et al. | |
| 9,095,300 B2 | 8/2015 | Bonadio et al. | |
| 9,271,753 B2 | 3/2016 | Butler et al. | |
| 9,277,907 B2 | 3/2016 | Fischvogt | |
| 9,277,908 B2 | 3/2016 | Butler et al. | |
| 2004/0015185 A1 | 1/2004 | Ewers et al. | |
| 2004/0254426 A1 | 12/2004 | Wenchell | |
| 2005/0020884 A1 * | 1/2005 | Hart | A61B 17/0293 600/206 |
| 2005/0137460 A1 | 1/2005 | Bertolero et al. | |
| 2005/0225582 A1 | 10/2005 | Wenchell | |
| 2005/0241647 A1 | 11/2005 | Nguyen et al. | |
| 2005/0267419 A1 | 12/2005 | Smith | |
| 2006/0030755 A1 | 2/2006 | Ewers et al. | |
| 2006/0084842 A1 | 4/2006 | Hart et al. | |
| 2006/0161050 A1 * | 7/2006 | Butler | A61B 17/0293 600/208 |
| 2006/0229501 A1 | 10/2006 | Jensen et al. | |
| 2006/0264701 A1 | 11/2006 | Kumar et al. | |
| 2007/0055107 A1 | 3/2007 | Wenchell | |
| 2007/0060884 A1 | 3/2007 | Hayek | |
| 2007/0085232 A1 | 4/2007 | Brustad et al. | |
| 2007/0118175 A1 | 5/2007 | Butler et al. | |
| 2007/0149859 A1 | 6/2007 | Albrecht et al. | |
| 2007/0225569 A1 | 9/2007 | Ewers et al. | |
| 2008/0011307 A1 | 1/2008 | Beckman et al. | |
| 2008/0021359 A1 | 1/2008 | Beckman et al. | |
| 2008/0132765 A1 | 6/2008 | Beckman et al. | |
| 2008/0146882 A1 | 6/2008 | Cropper et al. | |
| 2008/0146883 A1 | 6/2008 | Kistler et al. | |
| 2008/0146884 A1 | 6/2008 | Beckman et al. | |
| 2008/0221389 A1 | 9/2008 | Beckman et al. | |
| 2008/0249373 A1 | 10/2008 | Wenchell | |
| 2009/0069837 A1 | 3/2009 | Bonadio et al. | |
| 2010/0069859 A1 | 3/2010 | Weig | |
| 2010/0100043 A1 | 4/2010 | Racenet | |
| 2010/0113883 A1 | 5/2010 | Widenhouse et al. | |
| 2010/0145152 A1 | 6/2010 | Smith et al. | |
| 2010/0261974 A1 | 10/2010 | Shelton, IV et al. | |
| 2010/0268162 A1 | 10/2010 | Shelton, IV et al. | |
| 2010/0274093 A1 | 10/2010 | Shelton, IV | |
| 2010/0312060 A1 | 12/2010 | Widenhouse et al. | |
| 2010/0312061 A1 | 12/2010 | Hess et al. | |
| 2010/0312063 A1 | 12/2010 | Hess et al. | |
| 2010/0312065 A1 | 12/2010 | Shelton, IV et al. | |
| 2010/0312067 A1 | 12/2010 | Jensen et al. | |
| 2011/0054258 A1 | 3/2011 | O'Keefe et al. | |
| 2012/0136214 A1 | 5/2012 | Wenchell | |
| 2012/0174278 A1 | 7/2012 | Spivak | |
| 2012/0190932 A1 | 7/2012 | Okoniewski | |
| 2013/0066161 A1 | 3/2013 | Wenchell | |
| 2013/0253278 A1 | 9/2013 | Smith | |
| 2013/0253279 A1 | 9/2013 | Smith | |
| 2014/0121630 A1 * | 5/2014 | Dooney, Jr. | A61B 17/3498 604/500 |
| 2015/0038796 A1 | 2/2015 | Okoniewski | |
| 2015/0223835 A1 | 8/2015 | Smith | |
| 2018/0036034 A1 * | 2/2018 | Williams | A61B 17/02 |

FOREIGN PATENT DOCUMENTS

| | | | |
|---|---|---|---|
| WO | WO 2004075730 A2 | 9/2004 | |
| WO | WO 2006059318 A1 | 6/2006 | |
| WO | WO 2010141409 A1 | 12/2010 | |
| WO | WO 2014109706 A1 | 7/2014 | |
| WO | WO 2016064617 A1 | 4/2016 | |
| WO | WO-2018007244 A1 * | 1/2018 | A61B 17/3462 |

* cited by examiner

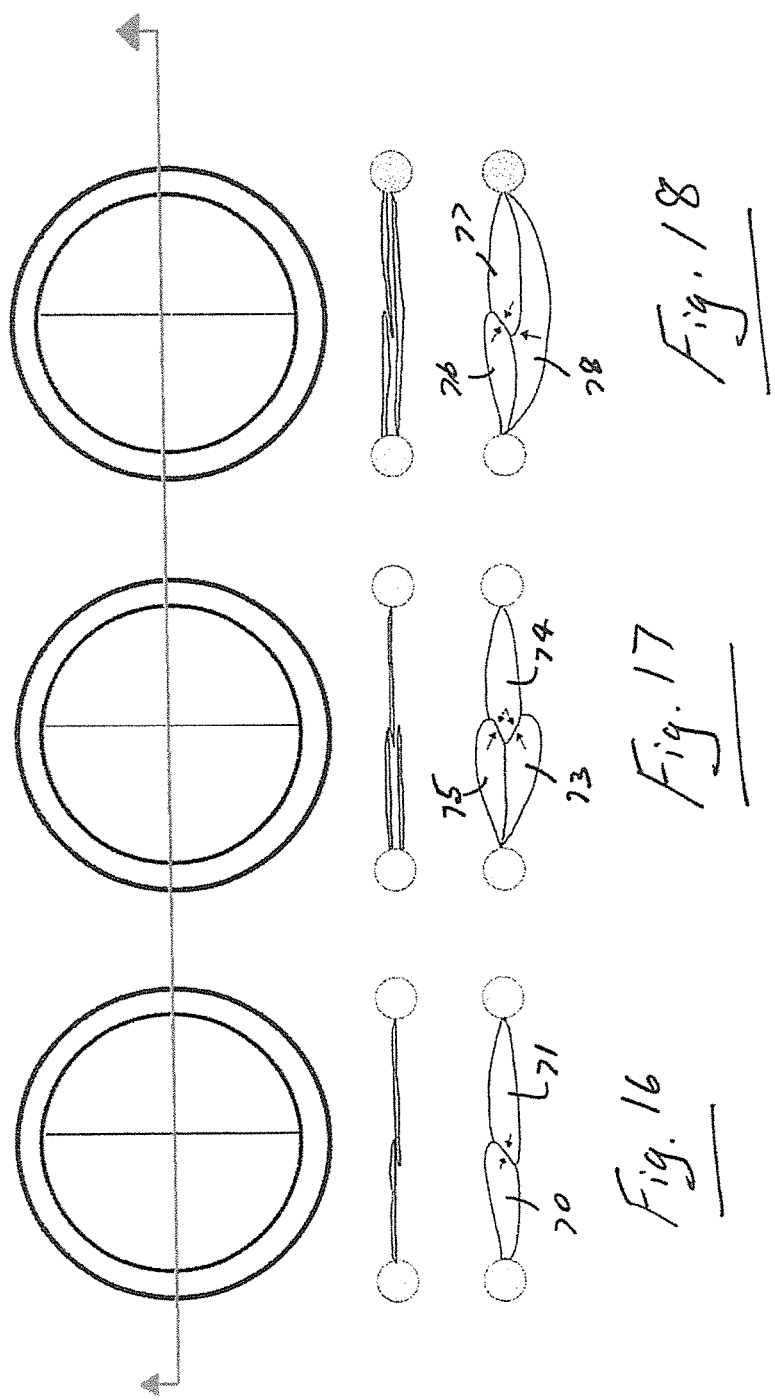

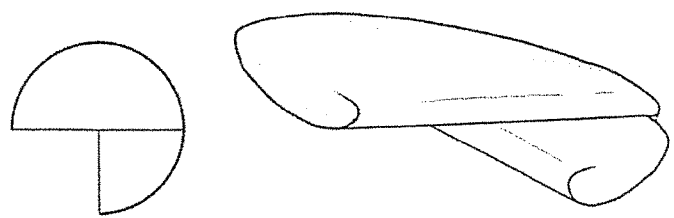
Fig. 31
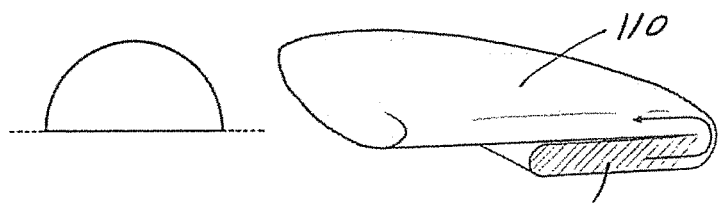
Fig. 32
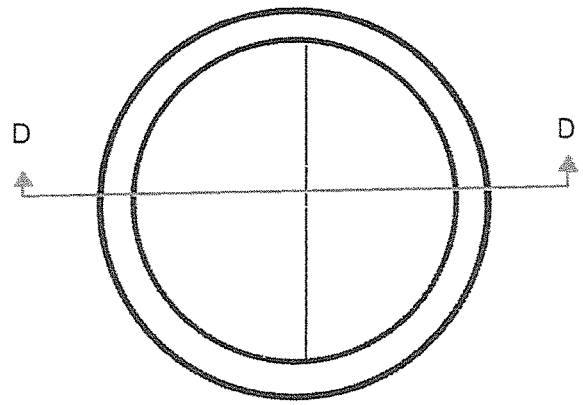
Fig. 33
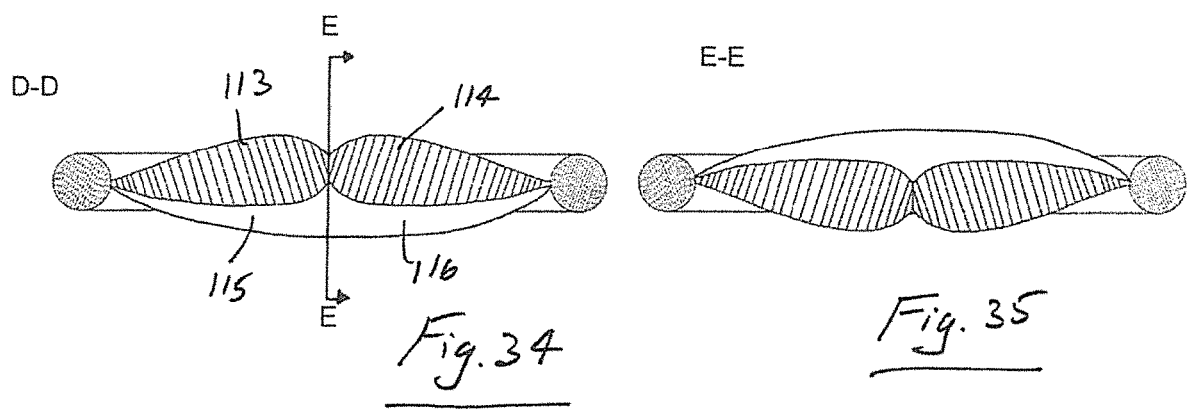
Fig. 34
Fig. 35

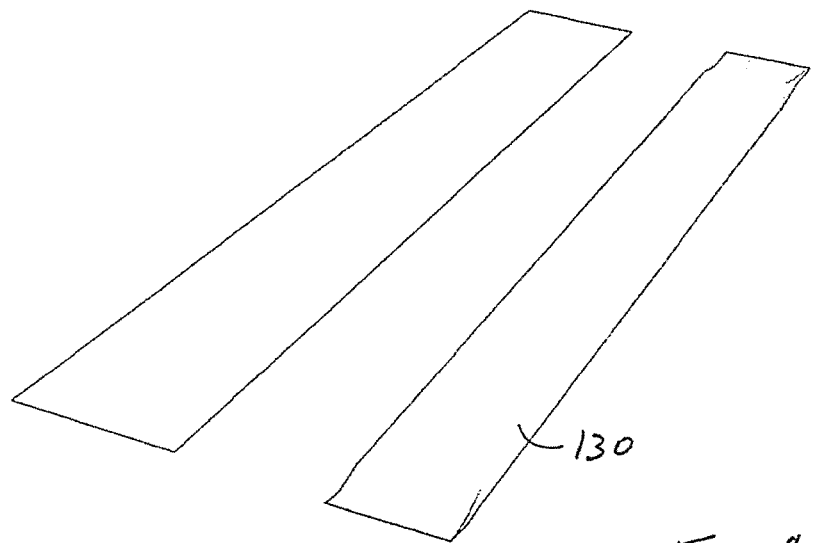
Fig. 41
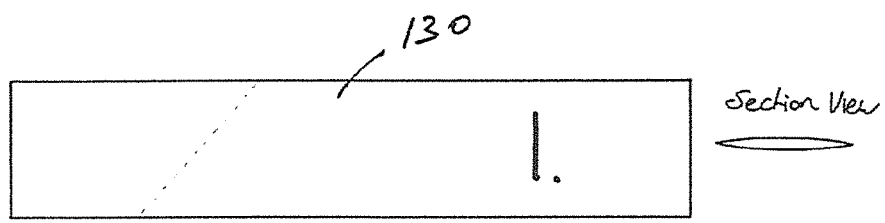
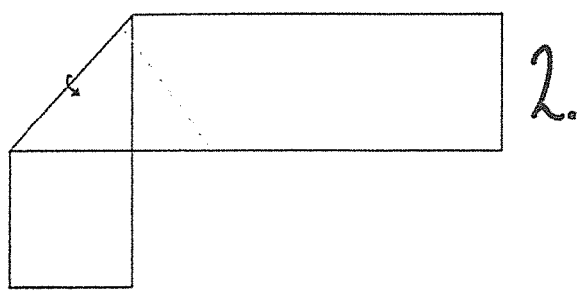
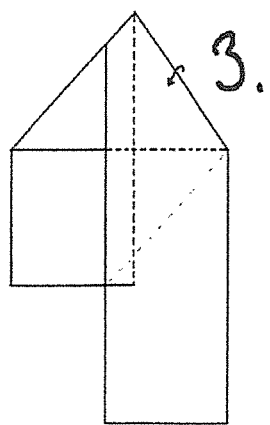 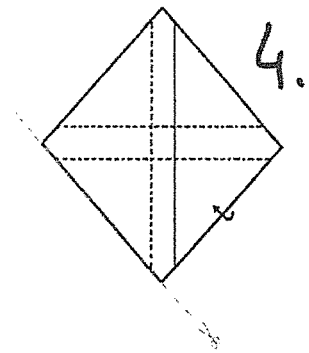
Fig. 42

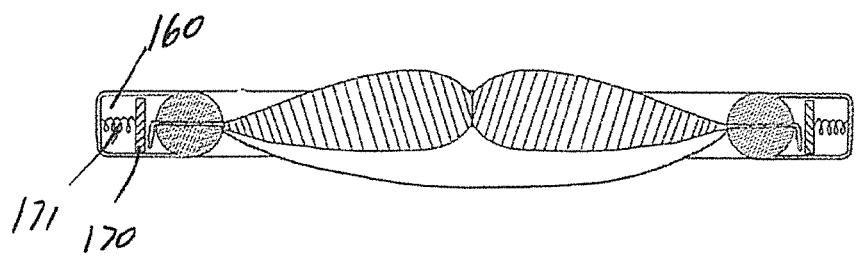
Fig. 60
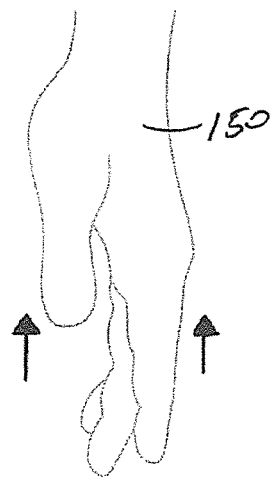
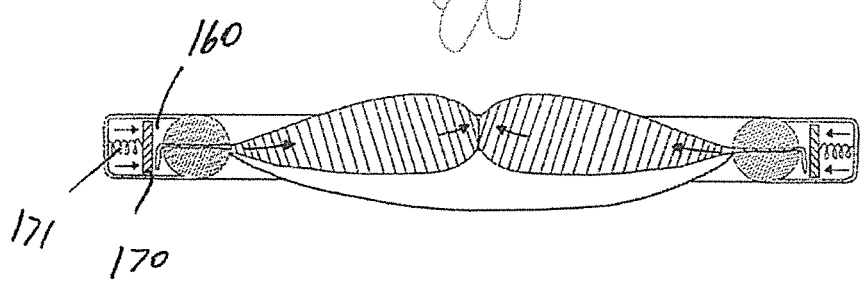
Fig. 61

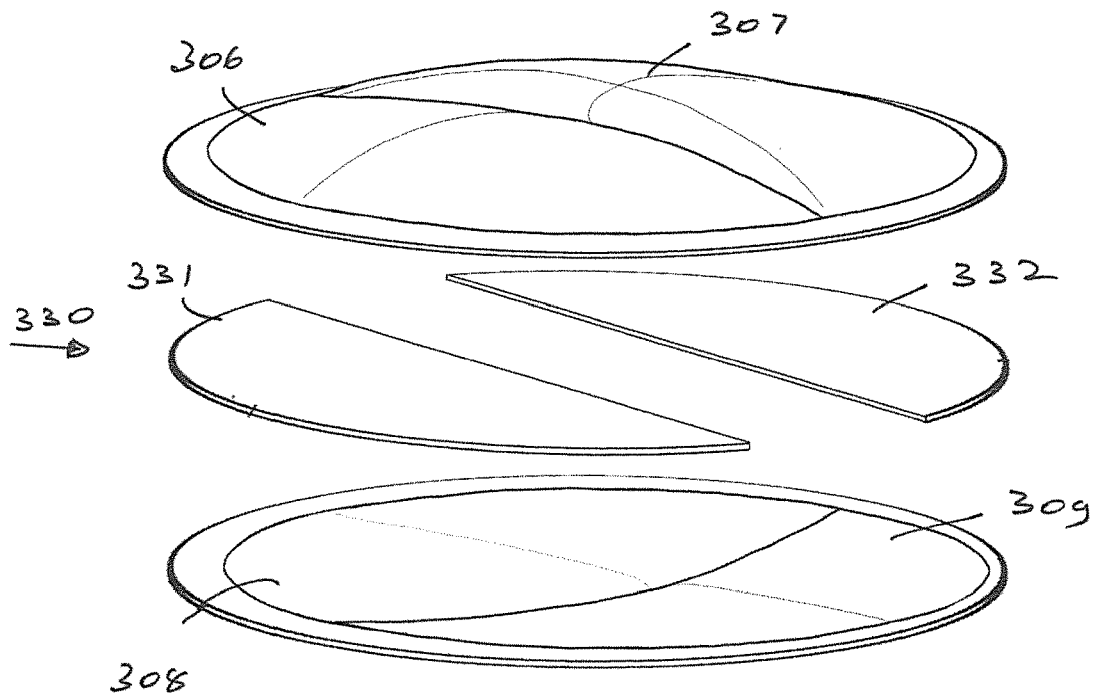
Fig. 88
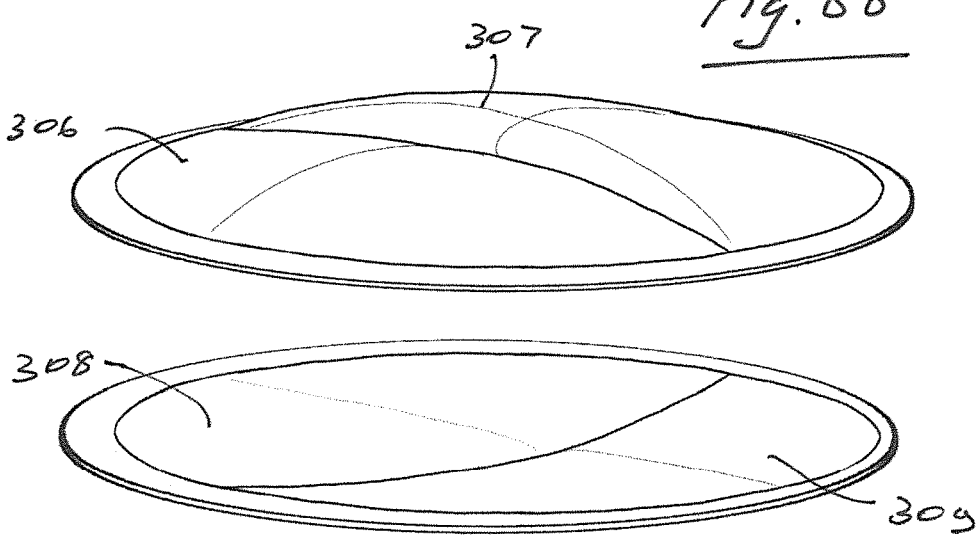
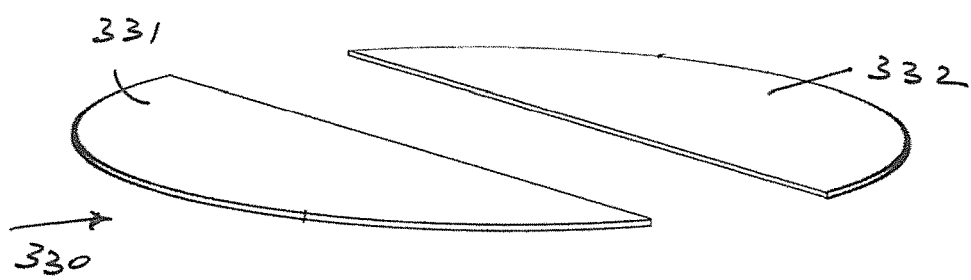
Fig. 89

351

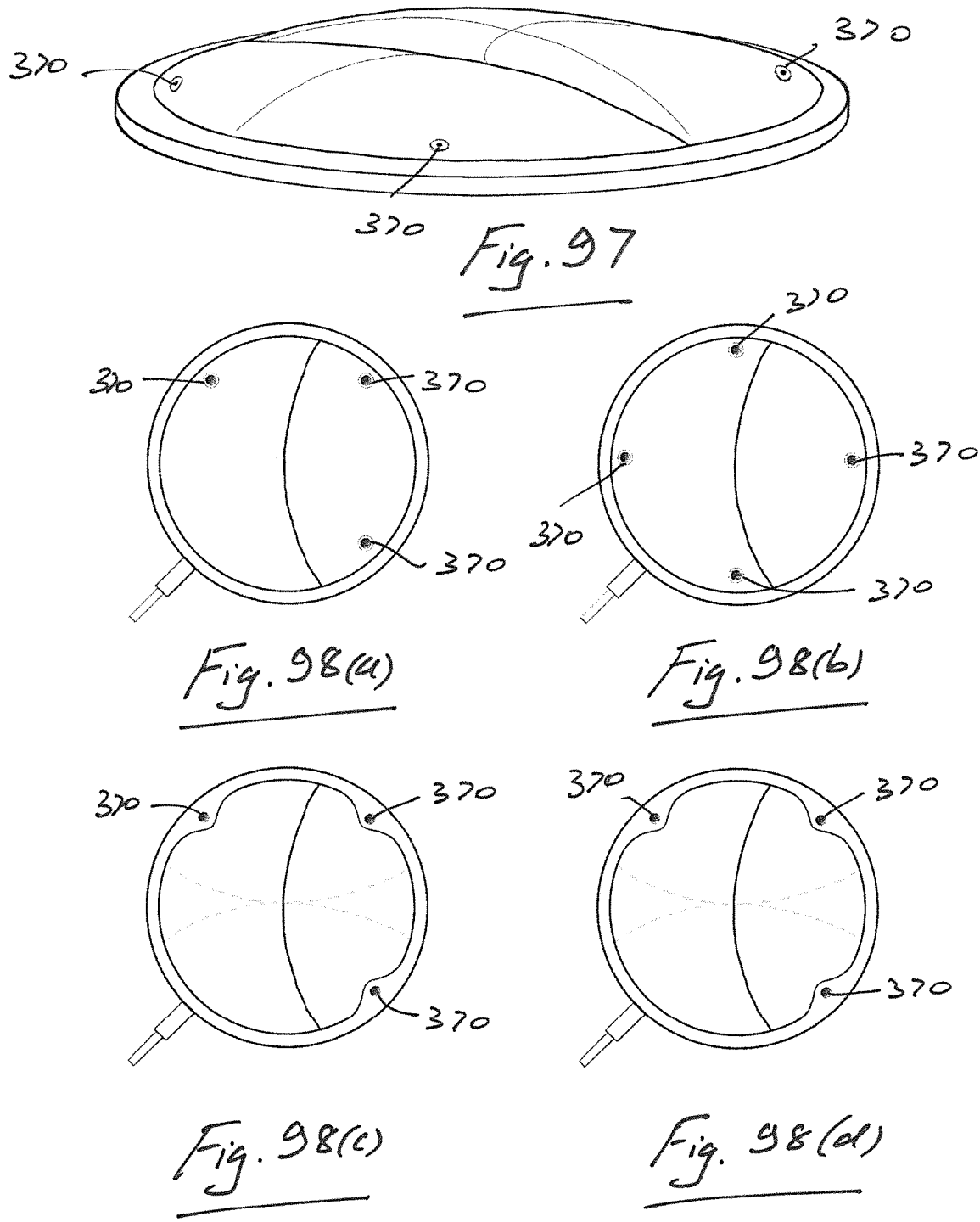

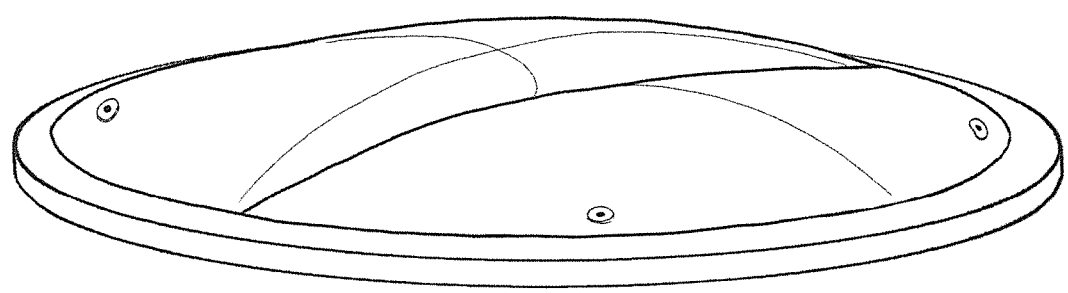
Fig. 99
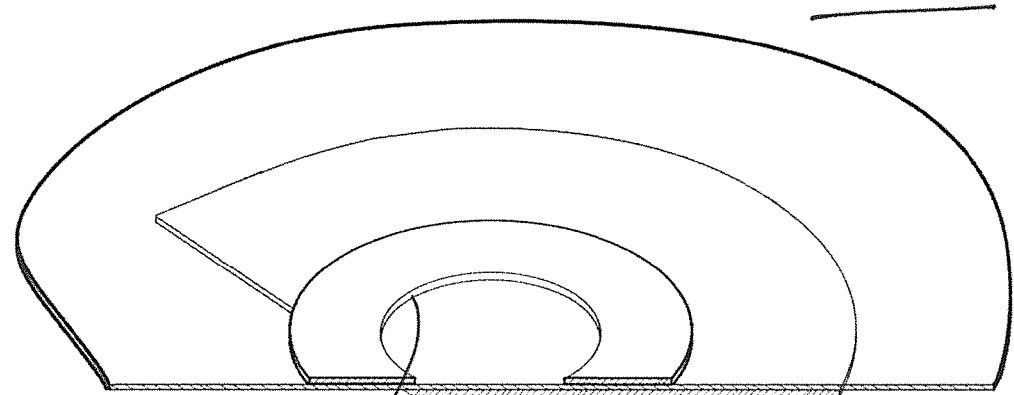
381  380  Fig. 100

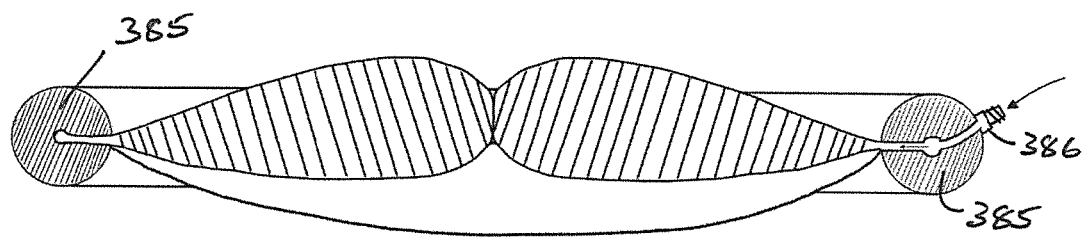
Fig. 101
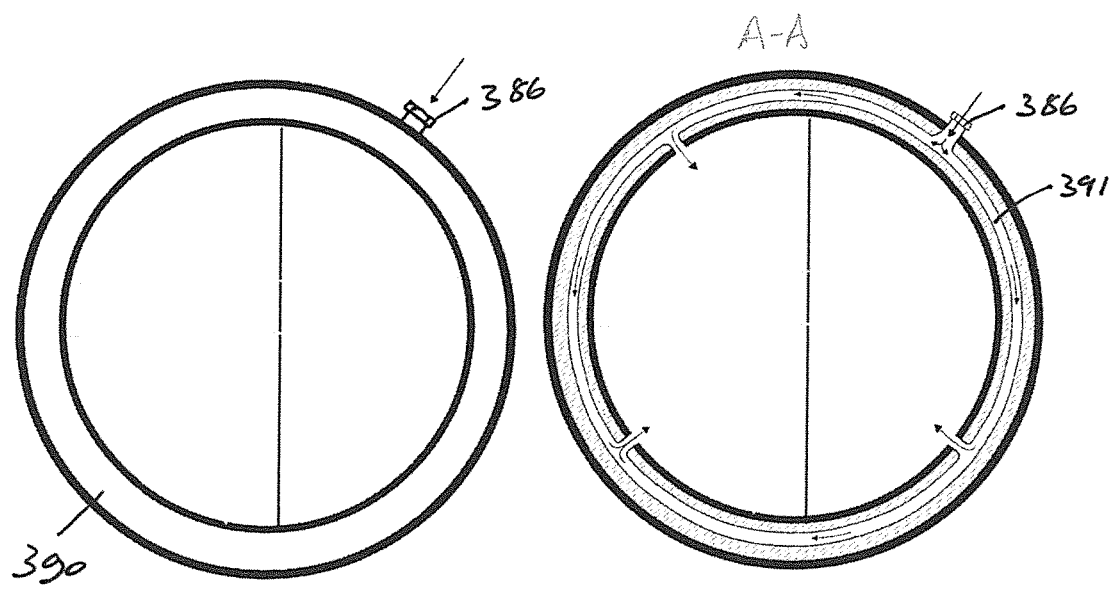
Fig. 102
Fig. 103
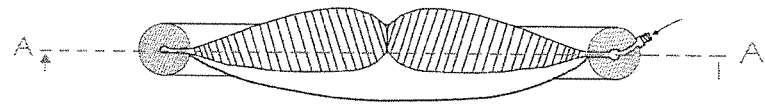
Fig. 104

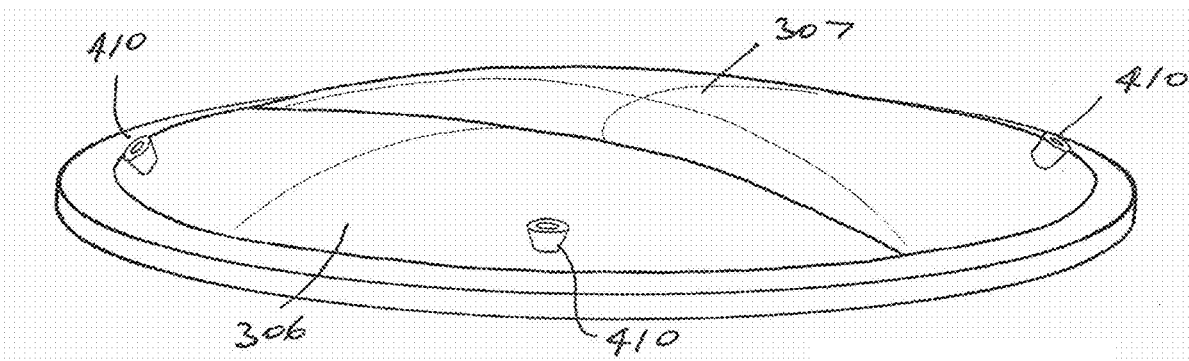
FIG. 108
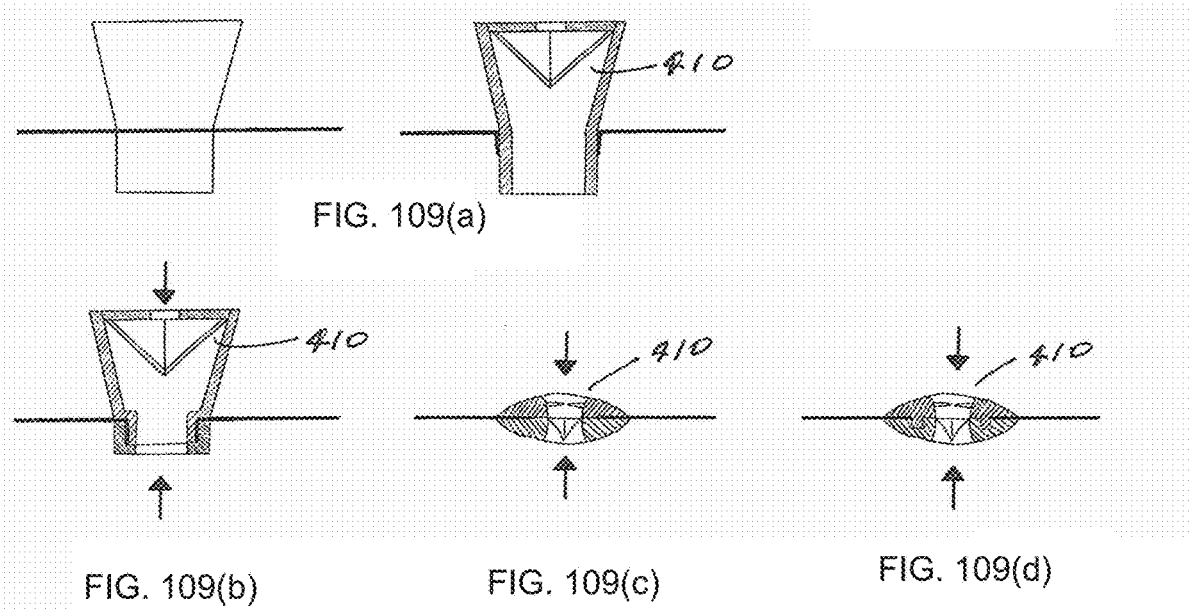
FIG. 109(a)
FIG. 109(b)　　　FIG. 109(c)　　　FIG. 109(d)

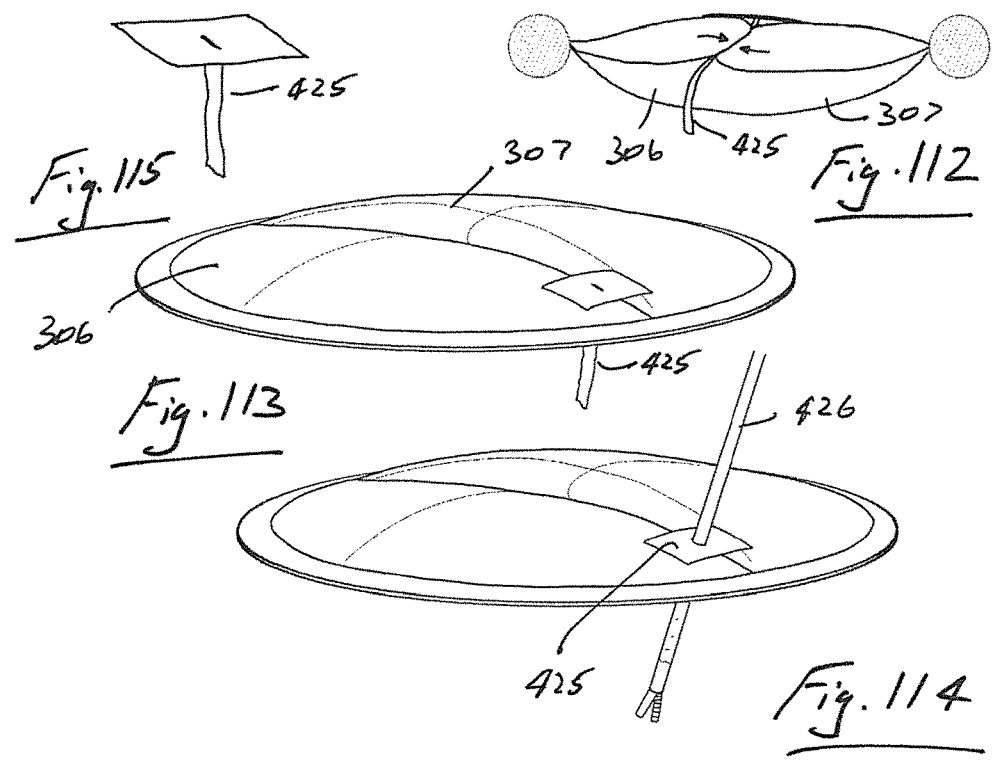
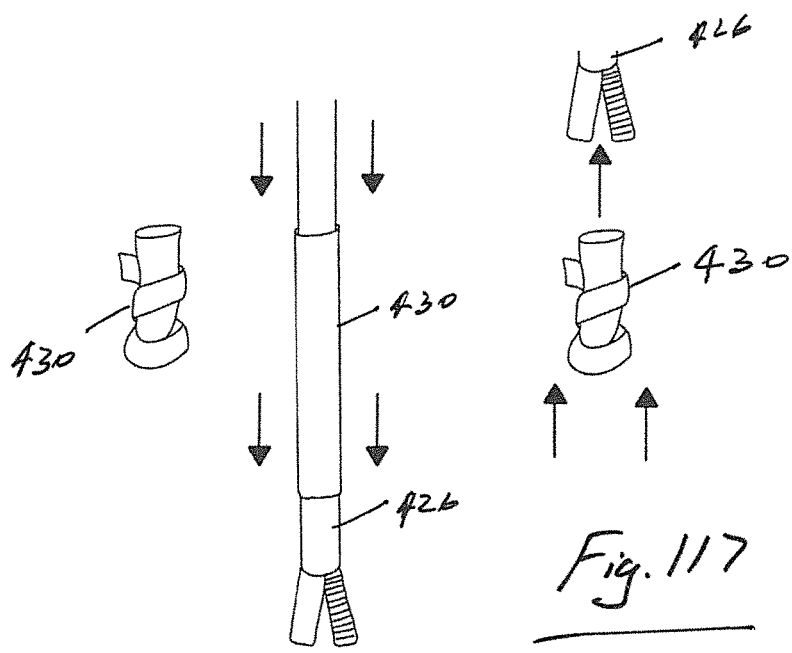

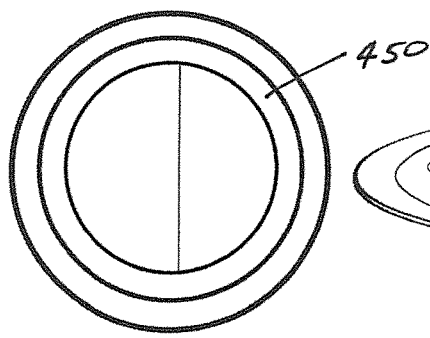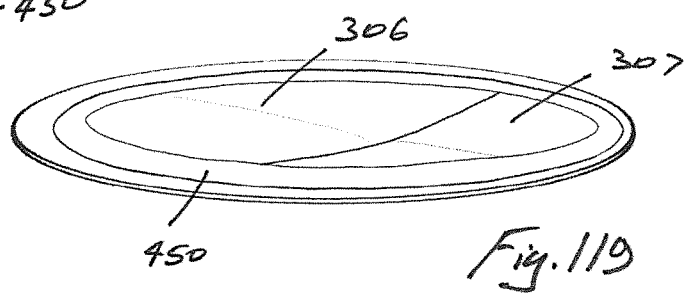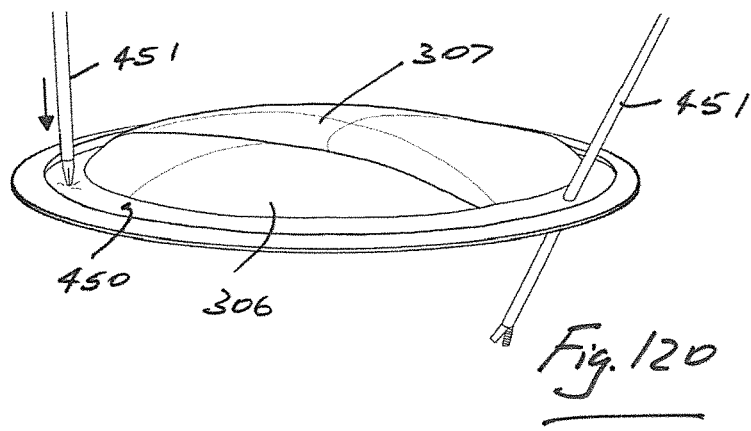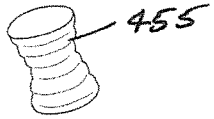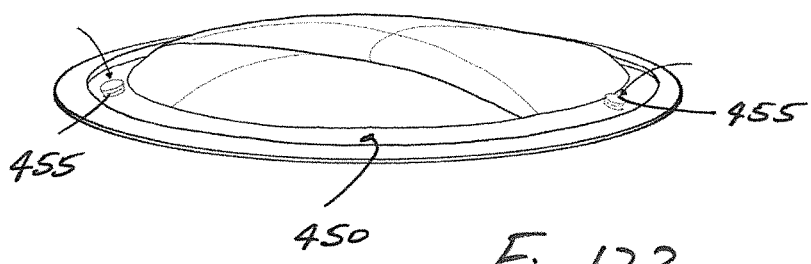

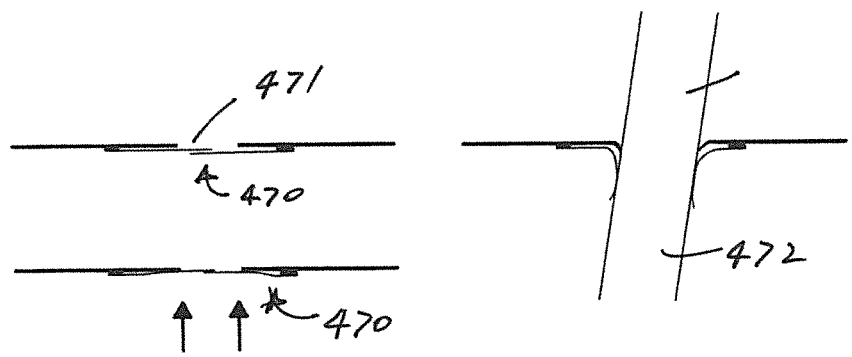
Fig. 127
Fig. 128
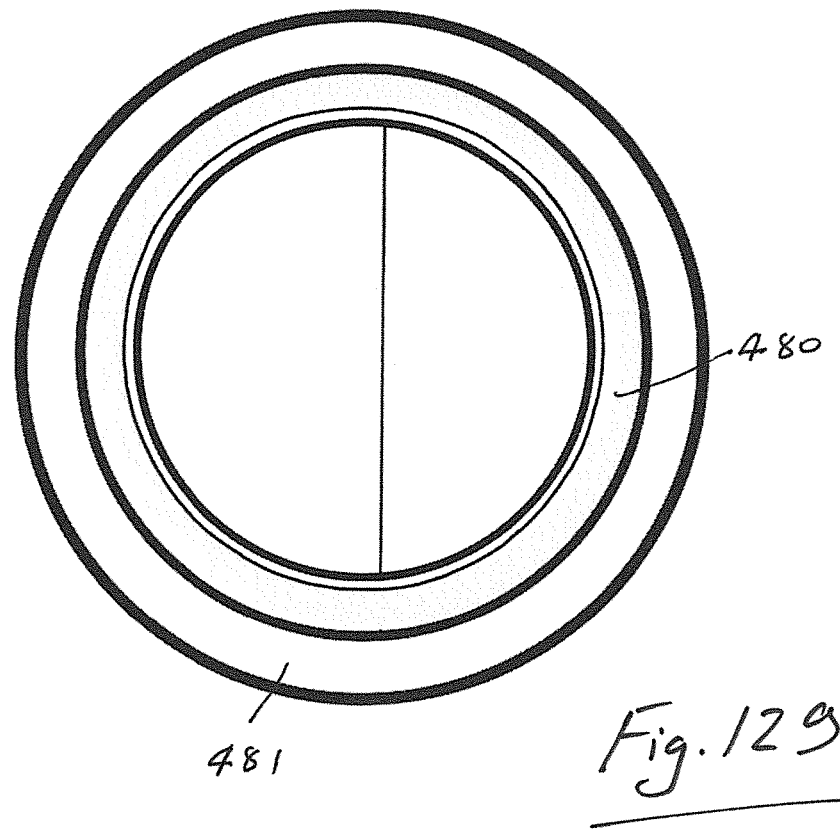
Fig. 129

ACCESS DEVICE

CROSS-REFERENCE TO RELATED APPLICATIONS

This application claims the benefits of priority under 35 U.S.C. § 119 of U.S. Provisional Application No. 62/462,630, filed on Feb. 23, 2017, and European Application No. 16177844.4, filed on Jul. 5, 2016. The disclosures of all of the above-listed applications are incorporated herein by reference in their entireties.

INTRODUCTION

This invention relates to an access device, especially for use in hand assisted laparoscopic surgery.

STATEMENTS OF INVENTION

According to the invention there is provided a surgical access device comprising at least two chambers, the chambers having an uninflated configuration and an inflated configuration, the chambers having a region of overlap in the uninflated configuration and the chambers being configured for sealing with an object inserted through the region of overlap in the inflated configuration.

In one embodiment the device comprises a first layer having at least two of the chambers and a second layer having at least two of the chambers. The region of overlap between the chambers of the first layer may be offset from the region of overlap between the chambers of the second layer.

The invention also provides a surgical access device comprising a plurality of chambers, the chambers having an uninflated configuration and an inflated configuration,
the device comprising a first layer of chambers and a second layer of chambers,
the first layer of chambers having a first region of overlap between the chambers,
the second layer of chambers having a second region of overlap between the chambers,
the second region of overlap being offset from the first region of overlap.

The leaves or chambers do not strangulate the wrist, allowing a blood flow path which reduces the chance and severity of tingling in the user's fingers and makes the valve more comfortable to use over a longer period of time. The device can be rotated around to move the pressure points if, over time, the pressure points become uncomfortable. The surgeon can also adjust the pressure in the leaves of the device to suit their needs by adding or releasing air via an inflation port.

In some embodiments the regions of overlap are offset by an angle of from 5° to 175°, 10° to 170°, 15° to 165°, 20° to 160°, 25° to 155°, 30° to 150°, 35° to 145°, 40° to 140°, 45° to 135°, 50° to 130°, 55° to 125°, 60° to 120°, 65° to 115°, 70° to 110°, 75° to 105°, 80° to 100° or 85° to 95°.

In one case the regions of overlap are offset by about 90°.

In some embodiments the region of overlap extends laterally for a distance between 5 mm and 50 mm, from 10 mm to 45 mm, or from 20 mm to 40 mm.

In one case the region of overlap extends laterally for a distance of about 30 mm.

In some embodiments the chambers of one layer have different properties to the chambers of another layer.

In one configuration the device comprises the first layer and only one other layer.

In another configuration the device comprises the first layer and two further layers.

In a further configuration the device comprises the first layer and three further layers.

In one case the device comprises the first layer and four or more further layers.

In some embodiments the chambers of the first layer are interconnected and the chambers of the further layer are interconnected but the chambers of the first layer are not interconnected with the chambers of the further layer.

At least some of the chambers of different layers may be interconnected.

In some cases, on inflation, at least one chamber of one layer is in sealing engagement with a chamber of an adjacent layer.

In one embodiment the device comprises a connection between at least some of the chambers to facilitate movement of an inflation medium between the chambers. There may be a valve device to control the flow of inflation medium between the chambers.

In some cases there is a connection between at least some of the chambers to facilitate movement of the inflation medium (such as air) between the chambers. There may be a constriction or valve to control the movement of air between the chambers.

In some cases the device further comprises a casing. The outer edge of the chambers may be fixed to the casing.

In some cases the fixing constricts or prevents flow between the chambers. In other cases the fixing is adapted to facilitate free flow of inflation medium between the chambers.

The casing may comprise a ring which may be of a rigid material.

In one embodiment the casing comprises an inner element to which the chambers are mounted and an outer element for containing the inner element.

In one case the engagement between the inner element and the outer element constricts the flow of air. In another case the engagement between the inner element and the outer element does not constrict the flow of air.

The casing may be adapted for mounting to another device such as a retractor and/or a valve cap.

In some embodiments the device further comprises a passageway through the device for reception of a trocar or an instrument. The passageway may have a valve or seal.

In some cases the device comprises an overflow chamber to facilitate movement of an inflation medium, in use. There may be a biasing element to control the flow of inflation medium into and/or out of the overflow chamber.

In some embodiments the device comprises an additional sealing layer. The additional sealing layer may be juxtaposed to an inflatable layer.

The hand access device according to the invention may include an additional sealing layer as a means to further improve sealing at extreme positions of a surgeons arm. This may also act as a safety/back-up feature in the unlikely event of a major leak path occurring—for example due to puncturing of one or more of the leaves. The additional safety layer may be of any suitable type and/or material and may be non-inflating. Some examples include overlapping sheets, non-overlapping sheets, an overlap sheet or a lip seal. Such an additional sealing layer may be juxtaposed to one of the other layers (such as an inflatable layer) described herein.

In one arrangement the additional sealing layer is located between two adjacent inflatable layers. In another arrangement the additional sealing layer is located on a distal side of the device. In one case the additional sealing layer is located on a proximal side of the device.

In some embodiments the additional sealing layer comprises at least two sheets. The additional sealing layer sheets may be overlapped. Alternatively the additional sealing layer sheets are spaced-apart.

In one case at least one of the additional sealing layer sheets are folded, for example, to define a chamber.

In one embodiment the additional sealing layer comprises a lip seal.

A port for introduction of an inflation medium into a chamber may be provided. The port may comprise a valve.

In one embodiment the device has a longitudinal axis and the chambers extend laterally of the longitudinal axis.

In one embodiment the device has a longitudinal axis and the overlap regions extend generally transverse to the longitudinal axis.

Also provided is a system comprising a device of the invention and a retractor base. In some cases the device is configured for coupling to the retractor base.

According to the invention there is also provided a surgical access device comprising at least two chambers which define inflation spaces, at least some of the chambers overlapping for sealing engagement when the inflation spaces are inflated, the walls of the inflated chambers being movable for passage of an object such as a surgeon's hand/arm or an instrument between the chambers whilst maintaining a seal.

In one embodiment the device comprises a connection between at least some of the chambers to facilitate movement of an inflation medium between the chambers.

In one case there is a valve device to control the flow of inflation medium between the chambers.

In one embodiment the device comprises a first layer having at least two overlapping chambers and at least one further layer having a least two overlapping chambers.

In one case the region of overlap between the chambers of the first layer is offset from the region of overlap between the chambers of the further layer. The regions of overlap may be offset, for example by an angle of from 30 to 150°, or at an angle of from 60° to 120°.

In one case the regions of overlap are offset by about 90°.

In one embodiment the device comprises the first layer and only one other layer.

In another embodiment the device comprises the first layer and two further layers.

In a further embodiment the device comprises the first layer and three further layers.

In another embodiment the device comprises the first layer and four or more further layers.

In one case the chambers of the first layer are interconnected and the chambers of the further layer are interconnected but the chambers of the first layer are not interconnected with the chambers of the further layer.

In one embodiment at least some of the chambers of different layers are interconnected.

In one case, on inflation, at least one chamber of one layer is in sealing engagement with a chamber of an adjacent layer.

In one embodiment the device further comprises a casing.

The outer edge of the chambers may be fixed to the casing. In some cases the fixing constricts or prevents flow between the chambers. In other cases, the fixing is adapted to facilitate free flow of inflation medium between the chambers.

In one embodiment the casing comprises a ring which may be of rigid material.

In some cases the casing comprises an inner element to which the leaves are mounted and an outer element for containing the inner element.

In one embodiment the engagement between the inner element constricts the flow of air.

In another embodiment the engagement between the inner element does not constrict the flow of air.

In some cases the casing is adapted for mounting to another device such as a retractor and/or a valve cap.

In one embodiment the device further comprises a passageway through the device for reception of a trocar or an instrument.

The passageway may have a valve or seal.

In one embodiment the device comprises an overflow chamber to facilitate movement of an inflation medium, in use. There may be a biasing element to control the flow of inflation medium into and/or out of the overflow chamber.

In one embodiment, a surgical access sealing device comprises expansile chambers 306, 307, 308, 309 which define inflation spaces. An upper layer 304 in one case comprises two chambers 306, 307 which are overlapped when uninflated. A lower layer 305 comprises two chambers 308, 309 which are also overlapped, when uninflated. The region of overlap between the chambers 306, 307 of the first layer is offset from the region of overlap between the chambers 308, 309 of the second layer. The walls of the inflated chambers are movable for passage of an object such as a surgeon's arm/hand whilst maintaining a seal.

In one embodiment the device comprises a port for introduction of an inflation medium into a chamber. In some cases, the port comprises a valve.

BRIEF DESCRIPTION OF THE DRAWINGS

The invention will be more clearly understood from the following description thereof, given by way of example only, in which:

FIG. 16 are views of flat and inflated two leafs overlapped;

FIG. 17 are view of a hand access device with three overlapped leaves flat and inflated;

FIG. 18 are views of a hand access device with four overlapped leaves flat and inflated;

FIGS. 31 and 32 illustrate the use of a single chamber to create leaves;

FIGS. 33 to 35 are views of a hand access device having four leaves;

FIGS. 36 to 41 illustrate the scaling or clamping of the edges of the device;

FIG. 42 are a series of images illustrating one method of manufacture;

FIGS. 60 and 61 are views of another hand access device including a mechanical biasing system;

FIGS. 88 and 89 are exploded views of devices according to further embodiments of the invention with an additional 2 part layer in place;

FIGS. 97 and 98(a) to 98(d) illustrate devices according to the invention with various secondary valves;

FIGS. 99 and 100 are views of a secondary valve and a reinforced hole;

FIG. 101 is a cross sectional view of another device according to the invention;

FIGS. 102 to 104 are views of further devices with housings having a conduit system;

FIG. 108 is an isometric view showing the location of a secondary (instrument) valve;

FIGS. 109(a) to 109(d) are cross sectional views of some secondary valves;

FIGS. 112 to 115 are views illustrating a further secondary seal;

FIGS. 116 and 117 are isometric views of a still further secondary seal;

FIGS. 118 to 120 are views of another device according to the invention;

FIGS. 121 to 123 are views of plugs and a device with the plug in situ;

FIGS. 127 and 128 are views of another device with a sealing flap system;

FIG. 129 is an underneath plan view of a device of the invention with one flap valve fixed to the valve housing;

DETAILED DESCRIPTION

Figure 1:
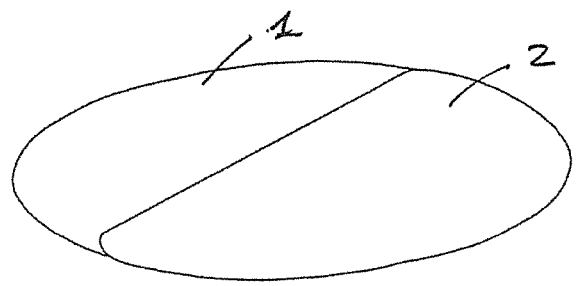
FIG. 1 is an isometric view of a hand access device according to the invention.

Referring to the drawings there are illustrated various surgical access devices which are used to seal a wound opening, for example, in an abdominal wall during hand assisted laparoscopic surgery. The devices facilitate access for a surgeon's hand/arm or an instrument whilst maintaining a seal to prevent or at least minimise leakage of gas from the pneumoperitoneum.

In general, the sealing device comprises at least two expansile chambers (or leaves) which define inflation spaces. At least some of the chambers are overlapped for sealing engagement between the chambers when the spaces defined by the chambers are inflated. In one case the chambers are overlapped in the plane of the abdomen. The walls of the inflated chambers are movable for passage of an object such as a surgeon's arm/hand or an instrument between the chambers whilst still maintaining a seal.

Preferably, for enhanced sealing, the device comprises a first layer of chambers and at least one further layer of chambers. The first layer of chambers have a first region of overlap between the chambers and the further layer of chambers have a further region of overlap between the chambers of the further layer. The further region of overlap is offset from the first region of overlap.

The access device has a longitudinal axis and the leaves/chambers extend laterally of this longitudinal axis. The overlap regions are generally transverse to the longitudinal axis.

The access device is used during surgical procedures, for example to seal a wound opening in an abdominal wall during laparoscopic surgery. The access device facilitates access for a surgeon's hand/arm or an instrument whilst maintaining a seal to prevent or at least minimise leakage of gas from the pneumoperitoneum. The chambers are preferably overlapped in the plane of the abdomen for enhanced sealing.

In some cases there is a connection between at least some of the chambers to facilitate movement of the inflation medium (such as air) between the chambers. There may be a constriction or valve to control the movement of air between the chambers. There may be two or more layers and the regions of overlap of the layers may be offset for enhanced sealing. There may or may not be connections to allow air to flow or not flow between the chambers in different layers.

In some embodiments there is an outer casing for the chambers to assist in retaining a fixed outer margin. The casing may, for example, comprise a rigid ring.

The device may be adapted for use with other surgical devices such as a wound protector and/or retractor such as those described in our U.S. Pat. No. 6,846,287, U.S. Pat. No. 7,559,893 and U.S. Pat. No. 6,254,534, the entire contents of which are incorporated herein by reference.

FIG. 1 illustrates a hand access device comprising two chambers or leaves 1, 2 in an overlapped configuration at rest. In this case the leaves 1, 2 are fully independent of each other. In this case the leaf edges are parallel but the edges may be angularly aligned.

Figure 2:
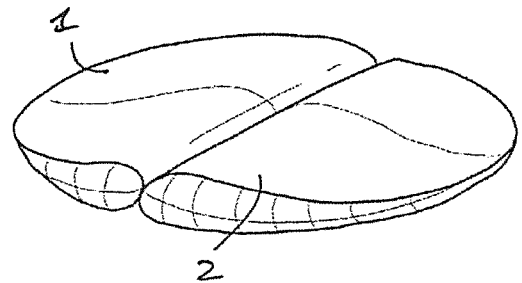
FIG. 2 is a view of the device of FIG. 1 in an inflated state.

FIG. 2 shows the leaves 1, 2 in an overlapped configuration when inflated. Some overlap remains once inflated— FIG. 2 shows a configuration at the limit of where the inflated leaves 1, 2 create an effective seal.

Figure 3:
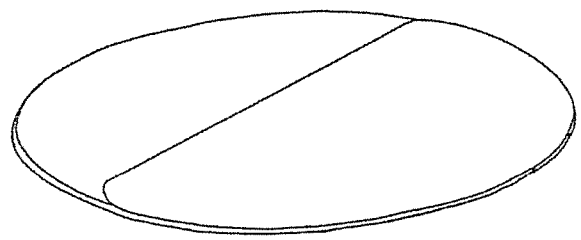
FIGS. 3 and 4 are views of another hand access device in uninflated and inflated states.
Figure 4:
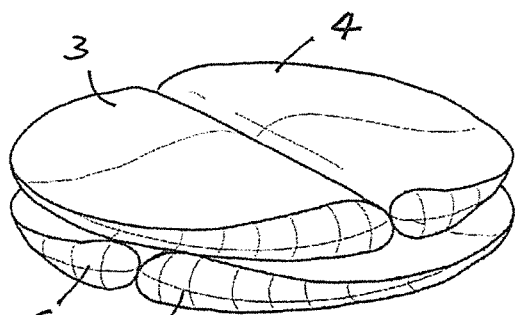

FIGS. 3 and 4 illustrate another hand access device which in this case comprises four chambers or leaves 3, 4, 5, 6 in an overlapped configuration at rest. In this case the leaves are fully independent of each other. The leaf edges of the top layer comprising the leaves 3, 4 are parallel to each other and perpendicular to the leaf edges of the leaves 5, 6 of the lower layer.

Figure 5:
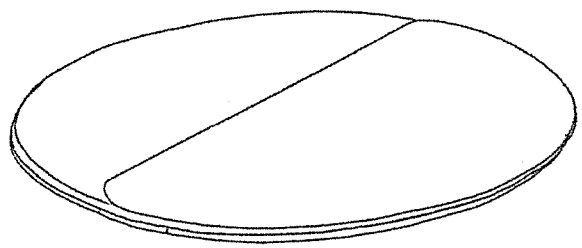
FIGS. 5 and 6 are views of a further hand access device in uninflated and inflated states.

FIG. 5 illustrates a further hand access device which in this case comprises six chambers or leaves 10, 11, 12, 13, 14, 15 in an overlapped configuration at rest. In this case the leaves are fully independent of each other. The leaf edges of the top layer 10, 11 are parallel to each other and perpendicular to the leaf edges of the lower layer 12, 13 and the leaf edges of the bottom pair 14, 15 perpendicular to this.

Figure 6:
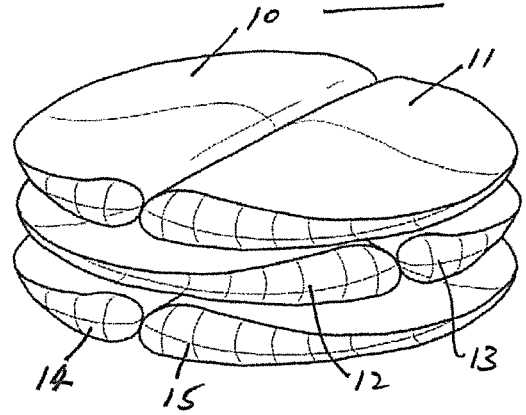

FIG. 6 shows that when inflated with air or gas the leaves 10, 11, 12, 13, 14, 15 butt against each other with sufficient pressure to cause a seal. Some overlap will usually remain. The drawing represents the limits at which the fully inflated configuration will maintain a seal. The seal improves with each layer. It is believed that this is due to an increase in sealing surface area.

Figure 7:
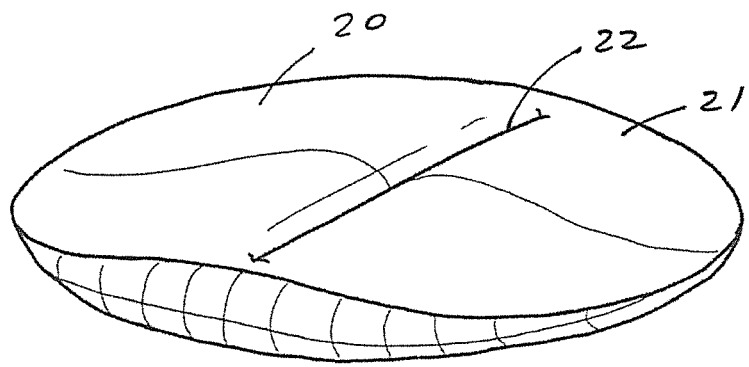
FIG. 7 is a view of a hand access device comprising two inter-connected leaves.

FIG. 7 illustrates a hand access device comprising two inter-connected leaves 20, 21 joined by material 22 either side of an orifice, allowing air to flow back and forth between the leaves 20, 21 freely when required. The material 22 creates a seal at rest when inflated.

Figure 8:
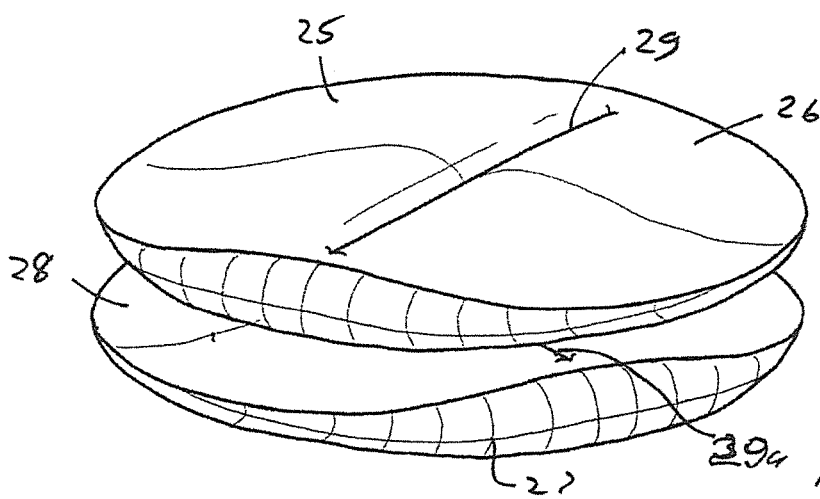
FIG. 8 is a view of a hand access device comprising two layers of two inter-connected leaves.

FIG. 8 shows two layers of two leaves 25, 26, 27, 28 interconnected at 29, 29a in which air is free to move within each set of interconnected leaves but not between different layers.

Figure 9:
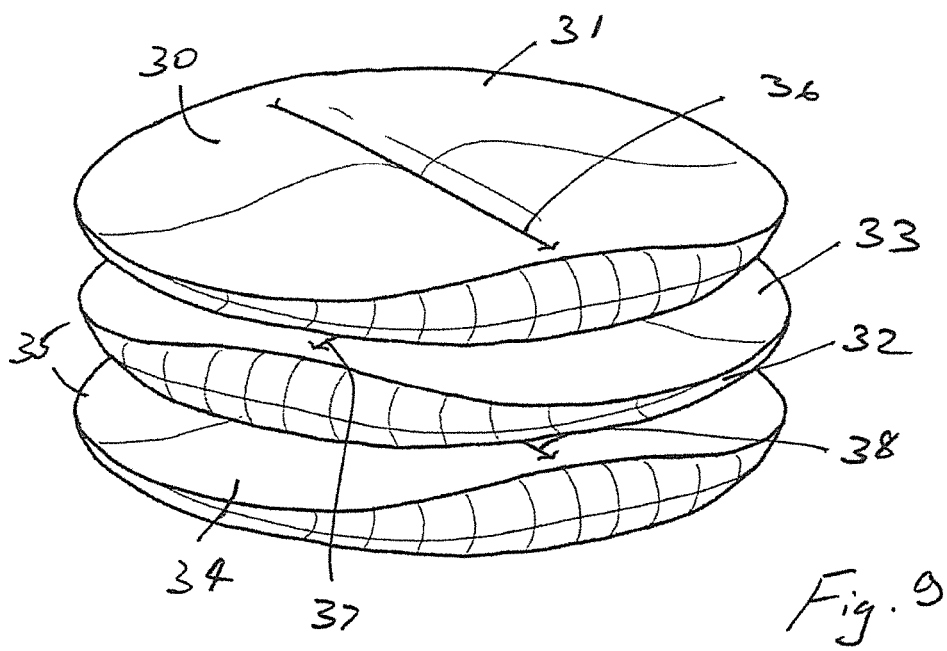
FIG. 9 is a view of a hand access device comprising three layers of two inter-connected leaves.

FIG. 9 illustrates three layers of two leaves 30, 31, 32, 33, 34, 35 interconnected at 36, 37, 38 in which air is free to move within each set of interconnected leaves but not between different layers. An increased number of layers increases seal performance.

Figure 10:
FIG. 10 is a view of a hand access device comprising four leaves.

FIG. 10 illustrates a configuration comprising four leaves 40, 41, 42, 43 in which a single leaf of material is folded in such a way as to create four leaves. The configuration of the leaves is similar to these described above in which each layer overlaps and is parallel to each other while perpendicular to a lower layer.

Figure 11:
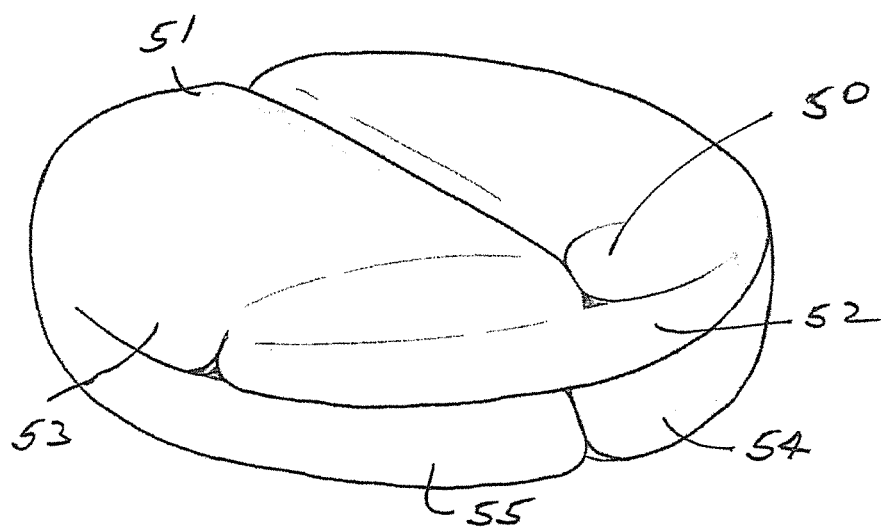
FIG. 11 is a view of another hand access device comprising six leaves.

FIG. 11 illustrates a configuration comprising six leaves 50, 51, 52, 53, 54, 55 in which a single leaf of material is folded in such a way as to create six leaves. The configuration of the leaves is similar to these described above in which each layer overlaps and parallel to each other while perpendicular to a layer immediately below it. Air is free to move from any leaf to any other leaf when required. Air may be moved by means of increased constriction/pressure.

Figure 12:
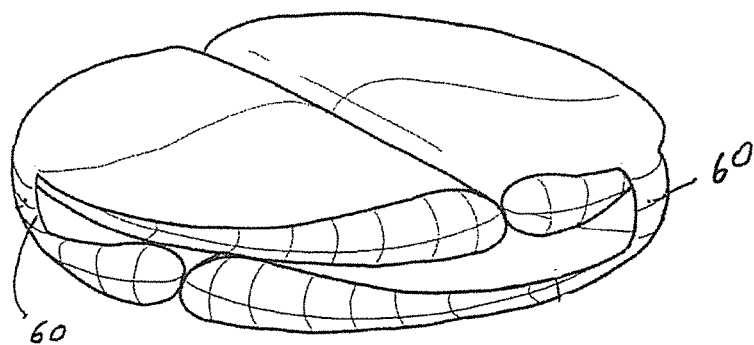
FIG. 12 is a view of a hand access device comprising four leaves which are connected to each other.
Figure 13:
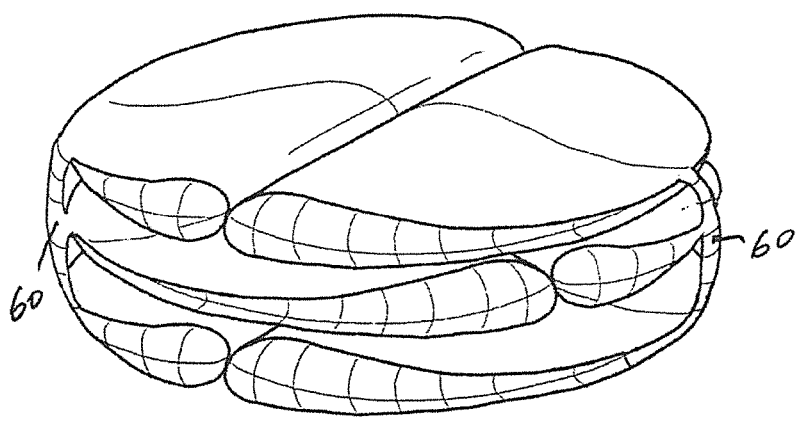
FIG. 13 is a view of a hand access device comprising six leaves which are connected to each other.

FIGS. 12 and 13 illustrate devices that function similarly to FIGS. 10 and 11. In this case the leaves are connected to each other by means of an additional chute or channel 60 to allow air to flow from leaf to leaf when required. The chute 60 may be of the same material or different material to that of the leaves and may be rigid, flexible or any configuration that allows for passage of air (with or without constriction on the flow).

Figure 14:
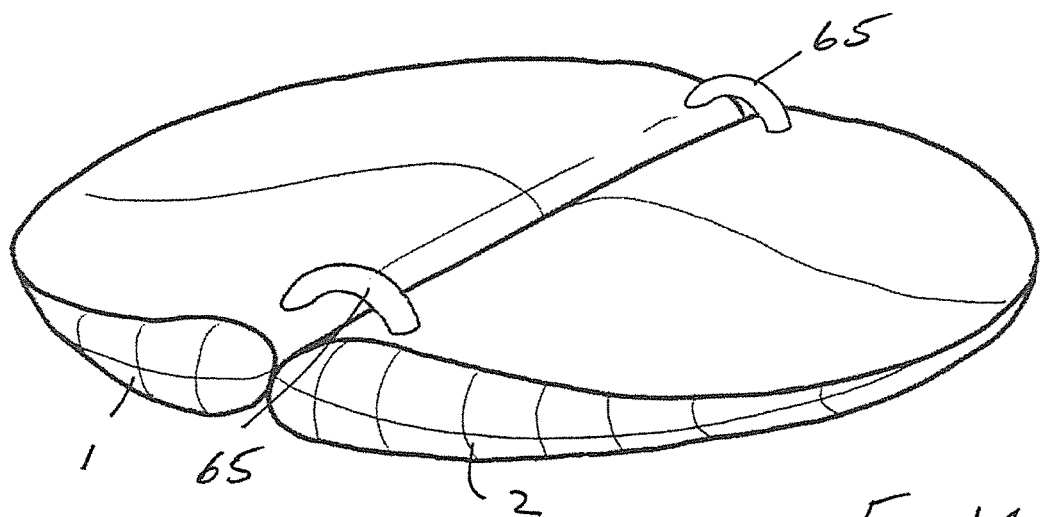
FIGS. 14 and 15 illustrate connections between leaves.
Figure 15:
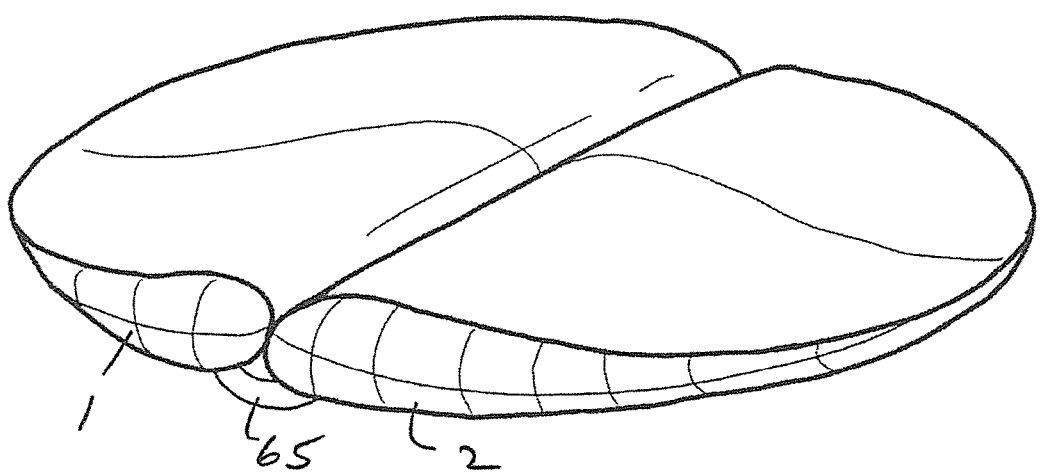
Figure 19:
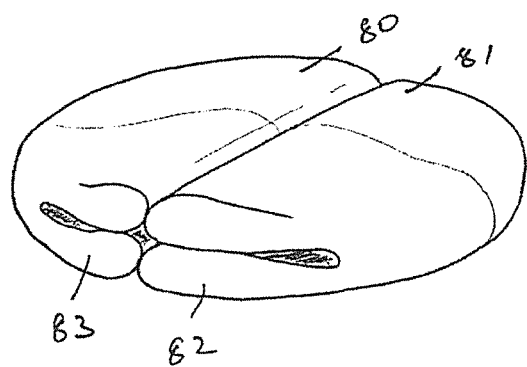
FIGS. 19 to 23 are views of a hand access device in which the leaves are parallel but with interconnections between the leaves.
Figure 20:
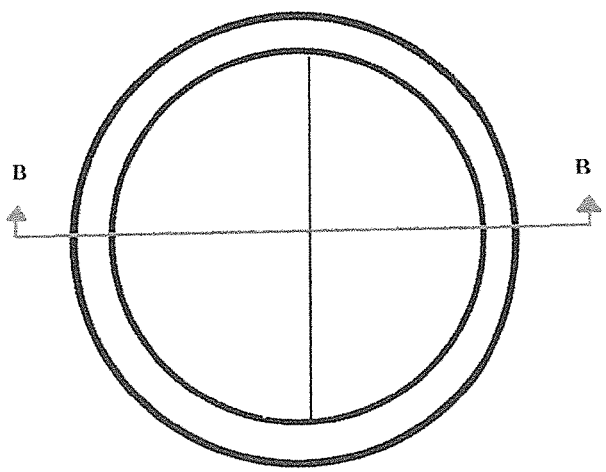
Figure 21:

FIGS. 14 and 15 are further illustrations demonstrating ways in which the leaves can be connected by connectors 65.

FIG. 16 shows a two-leaf 70, 71 overlapped configuration in uninflated and inflated states. The inflated version seals with some overlap present over a large surface area.

FIG. 17 shows a three-leaf 73, 74, 75 in parallel overlapped configuration in uninflated and inflated states. The inflated version interlocks with increased sealing surface area.

FIG. 18 illustrates a four-leaf 76, 77, 78, 79 with top layer perpendicular to bottom layer in overlapped configuration. Leaf 79 which is in front of leaf 78, is not visible in FIG. 18. The lower layer applies pressure upwards (and vice versa) to create an even larger sealing surface with tighter sealing where leaves come together.

Figure 22:
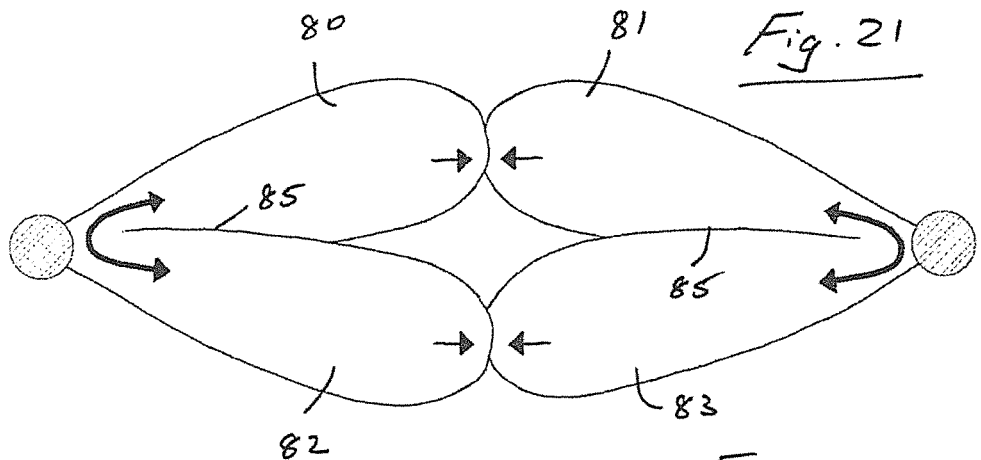
Figure 23:
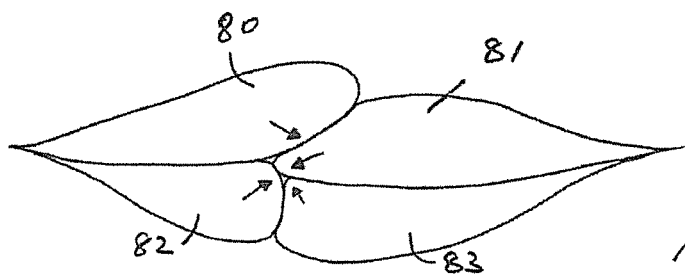
Figure 24:
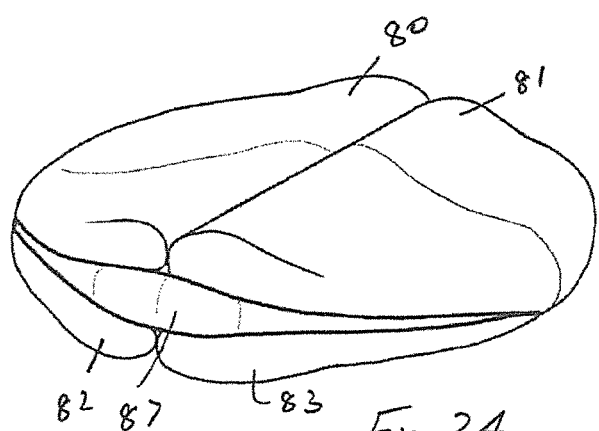
FIGS. 24 to 27 are views of a modified hand access device with an intermediates layer.
Figure 25:
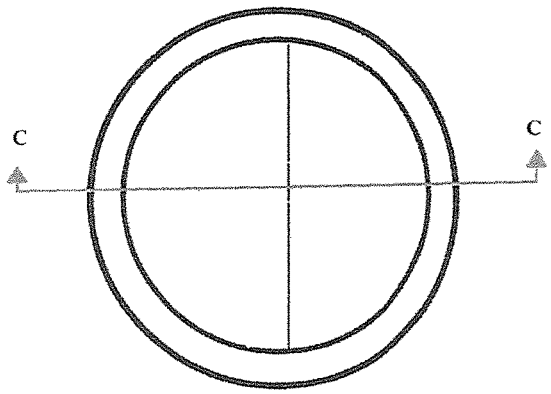
Figure 26:
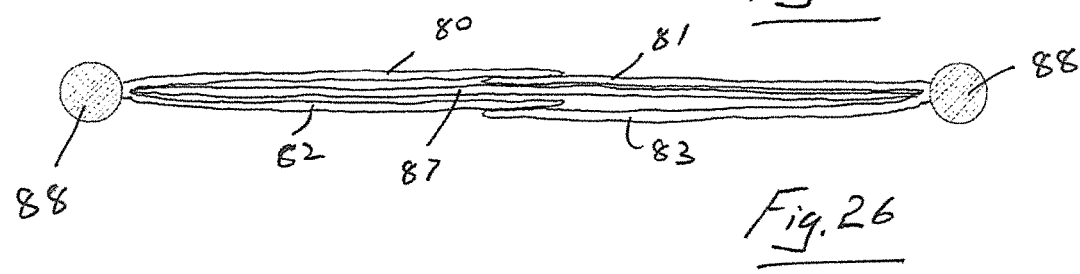
Figure 27:
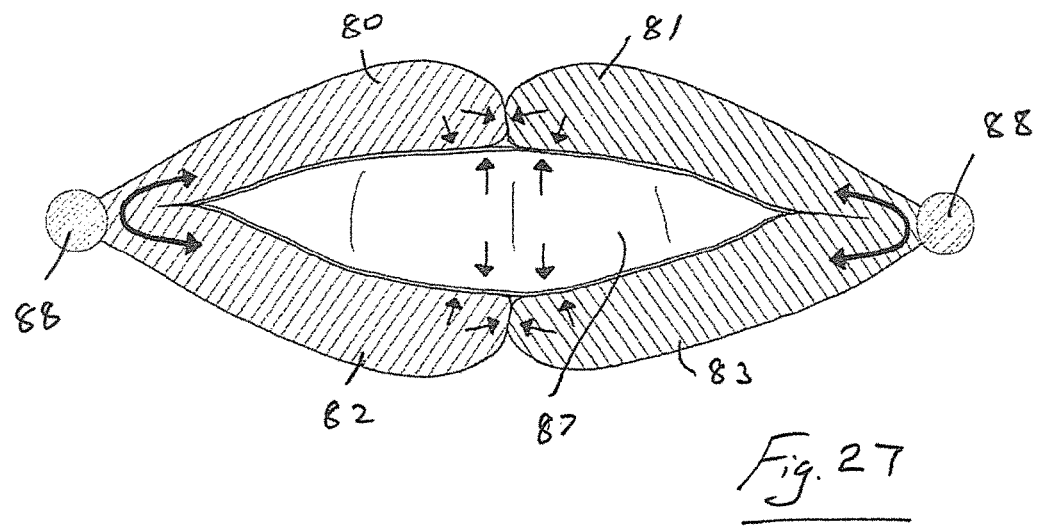

Referring to FIGS. 19 to 23 there is illustrated a four leaf 80, 81, 82, 83 configuration in which all leaves are parallel but each leaf is connected to the leaf below it by means of a fold or partial fixation 85. The leaves overlap as shown at rest in a stepped interlocking fashion. Once inflated, the configuration at the limit of creating a seal is shown in FIG. 22 whereby the leaves butt against each other. However, a more realistic configuration when inflated is shown in FIG. 23 with non-uniform spread of sealing surfaces across all leaves.

FIGS. 24 to 27 illustrates a device that differs from the device of FIGS. 19 to 23 in that an intermediary (and perpendicular) layer of two leaves 87 is introduce between the folded leaves. This creates an enhanced universal seal while allowing air to move from the top layer to the bottom layer leaf pairs as shown. Sealing surfaces are more dispersed and more effective.

Although, not illustrated in some embodiments, the inclusion of an outer casing or ring (such as indicated by 88 in FIGS. 26 and 27) may be important to the performance of the sealing system of the invention. Such a casing may serve as a radial constrictor which biases the leafs towards the centre, allowing them to seal reliably and repeatedly.

Figure 28:
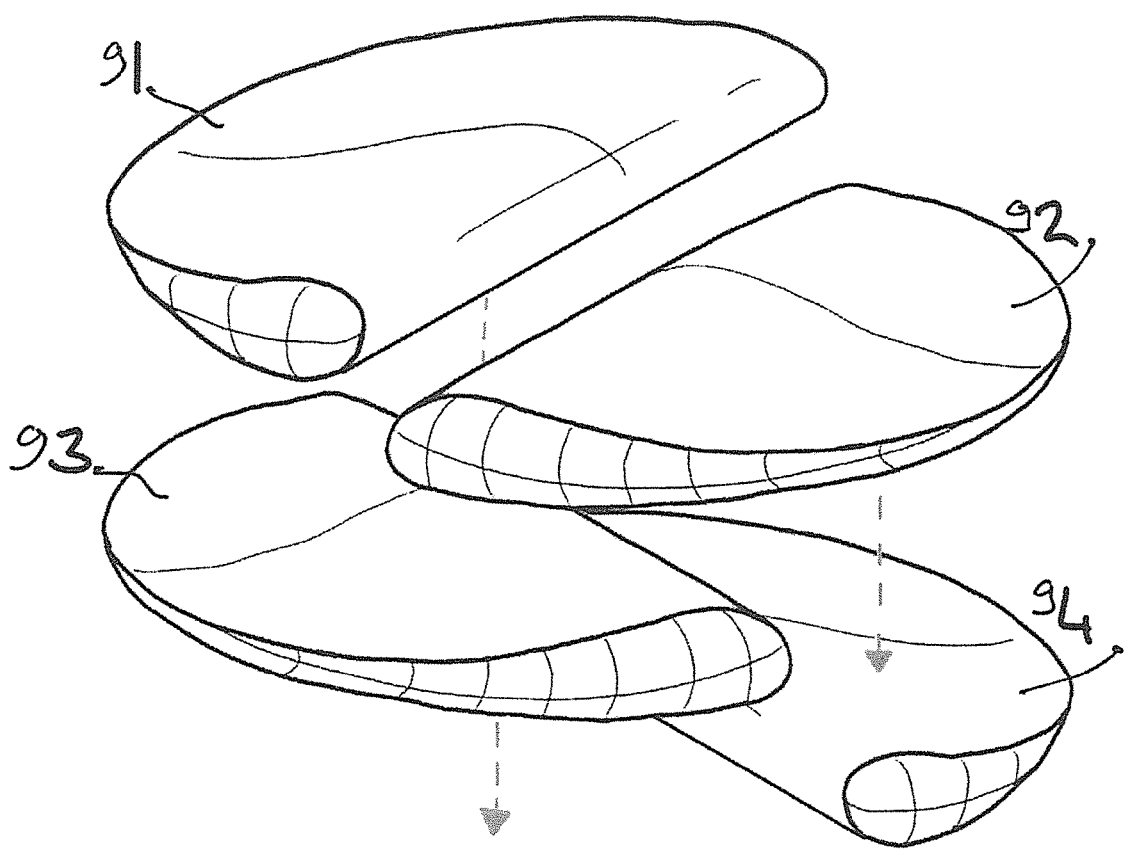
FIG. 28 is an exploded view showing multiple leaves.

FIG. 28 is an exploded view of a 4-leaf configuration with numbered leaves (91 to 94 but not limited to 4). There may be any number of combinations of leaves connected to each other for the purpose of air flow between them in order to maintain a seal when pressure is applied to one or more than one leaf. In one case all leaves are connected to all other leaves (directly or indirectly). In another case all four leaves are completely independent. Alternatively any combination of leaves may be independent and/or connected together. For example, leaf 91 could be connected to leaf 92, 92 connected to 93, and 93 to 94. Leaf 91 would not be directly connected to leaf 94 in this particular scenario, but air could move from 91 to 94 through 92 and 93. Similarly, 91 could be connected directly to 94 and 92 connected only to 93. These are just examples of the many configurations and permutations that may be used.

Figure 29:
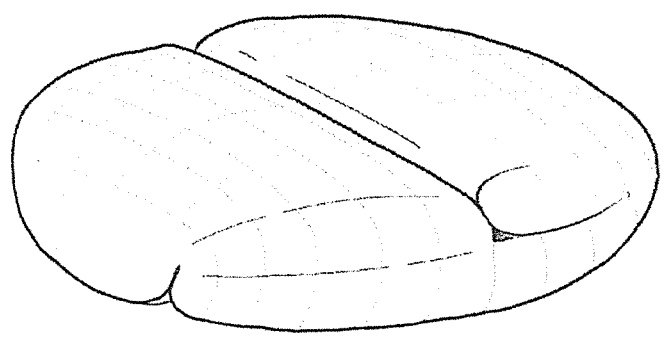
FIGS. 29 and 30 are views of another hand access device with four leaves.
Figure 30:
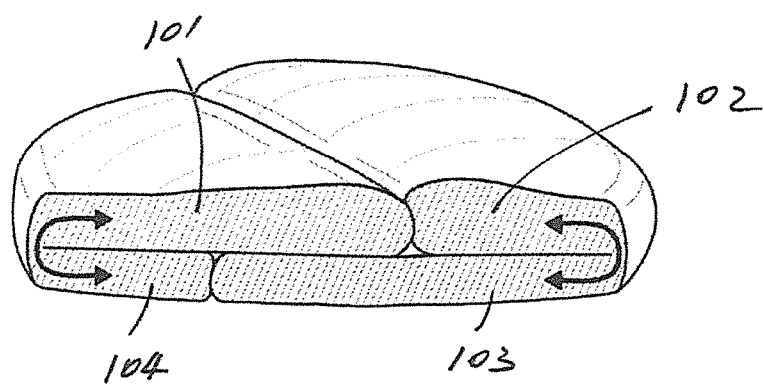

FIGS. 29 and 30 illustrates another device in which the cut section view of FIG. 30 shows an example configuration of a device comprising four leaves 101, 102, 103, 104 in one body. The arrows indicate that air can move from one leaf to another, in this case via a folded configuration. As mentioned previously, the means by which the air flows between leaves is not limited to folds.

Referring to FIGS. 31 and 32 there is illustrated another version in which one body is used to create two leaves 110, 111 which lie one on top of the other and perpendicular (or some arbitrary angle) to each other.

FIGS. 33 to 35 show a four leaf 113, 114, 115, 116 version in which the bottom layer is perpendicular to the top layer. Section D-D (FIG. 34) shows that the sealing surface of the bottom layer (white leaf) is perpendicular to the top layer and section E-E (FIG. 35) shows the opposite, where only one of the sealing surfaces on the top layer is visible.

Figure 36:
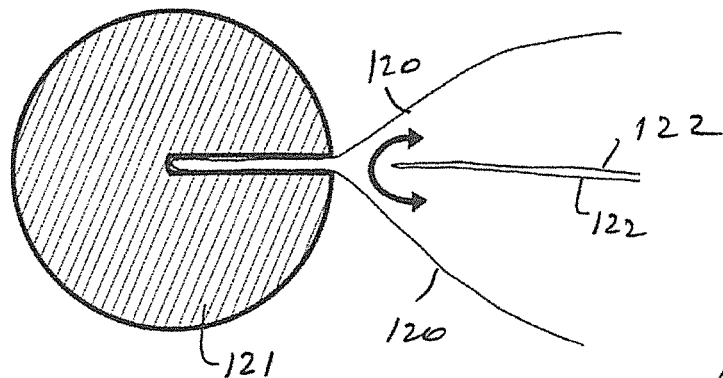
Figure 37:
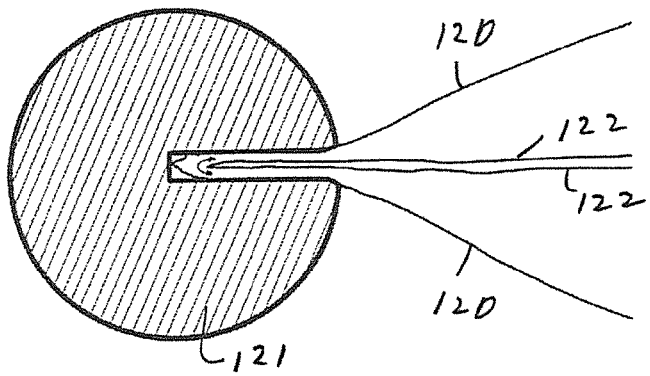
Figure 38:
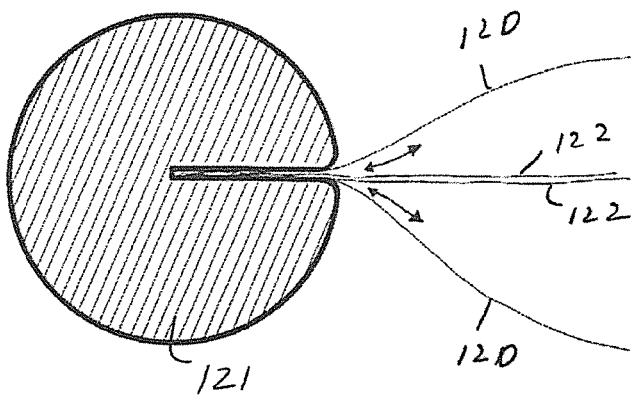

FIGS. 36 to 38 illustrate a number of possible methods by which the sealing leaves can be fixed or clamped at its edges in a casing, usually circumferentially, using a ring 121 which may be rigid.

FIG. 36 shows an example in which the outermost sheets 120 of the leaves are clamped within a casing 121 and inner sheets 122 are left unclamped while maintaining their structure/fold by other means, thus allowing air to move freely and unrestricted.

FIG. 37 is an example in which the entire fold is clamped within the casing 121 in a somewhat loose configuration whereby the entire fold remains within the casing at all times and yet offers little or no restriction to the flow of air across the fold, as shown by the arrow within the fold. This provides an unconstricted flow while fixing the entire fold within the casing 121.

FIG. 38 is similar to FIG. 37 in that the entire fold is also clamped and fixed within the casing 121. The primary difference with this configuration is that the air path is constricted. This means that air does not flow freely and easily through the fold/chute but instead requires an external force and pressure increase in one leaf in order to move air through the casing or into another connected leaf.

In all cases, there may be unconstricted or constricted air flow between the leaves.

Figure 39:
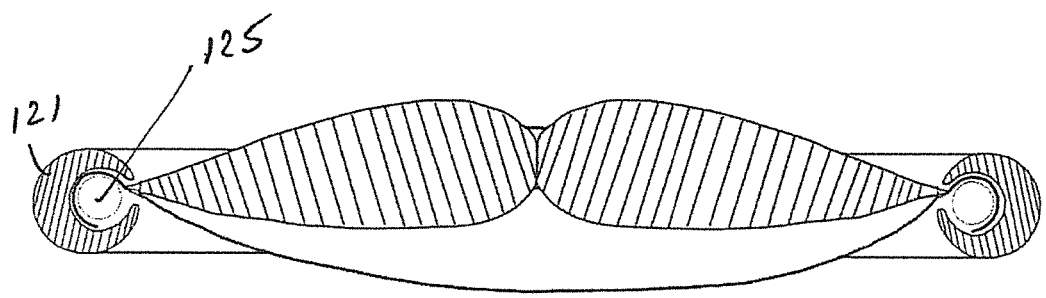

FIG. 39 shows another possible method of clamping the leaves to the casing 121 using an inner body such as a ring 125. This inner ring 125 may be friction locked, glued or engaged by any other means with the outer casing 121.

Figure 40:
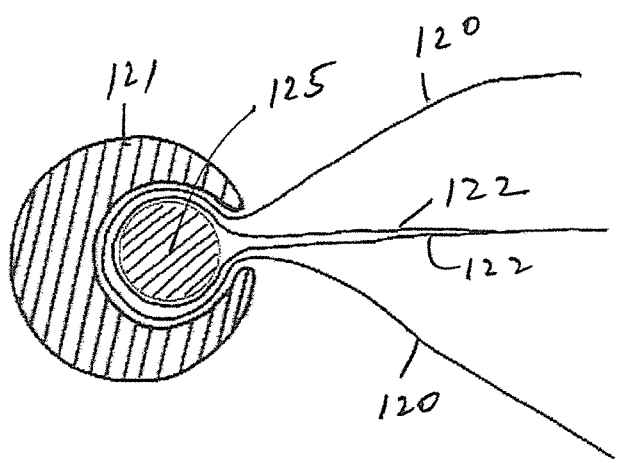

FIG. 40 shows a configuration in which the leaves are folded around an inner ring 125 rather than fixed and this serves as the folding point and air flow constriction. The physical contact against the inner ring 125 serves to constrict the flow in a similar way to the above versions where an external force is required to move the air from one leaf to another. The rings 121, 125 may be sized to achieve a desired level of constriction to the flow path.

FIGS. 41 and 42 illustrate one possible method of manufacture. The final leaf configuration is achieved by taking single body 130 fully sealed on all edges (but with an additional feature that allows venting and filling of air) and folding in it in such a way as to achieve four overlapping leaves. The two top leaves are perpendicular to the layer below. The excess material after the last fold is trimmed and sealed off. This illustrates possible processes of folding and sealing that may be used to achieve desired performance features.

Figure 43:
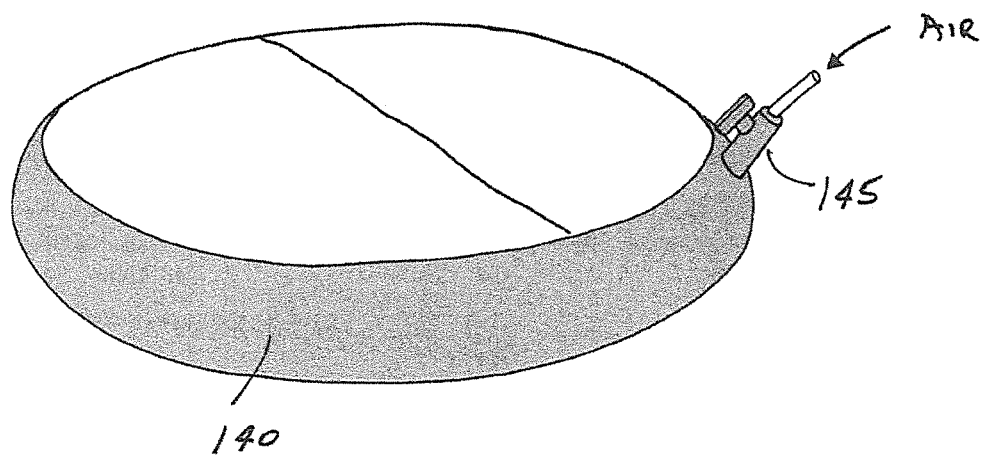
FIGS. 43 and 44 illustrate a hand access device according to the invention with an outer-casing enclosing the edges of the leaves.
Figure 44:
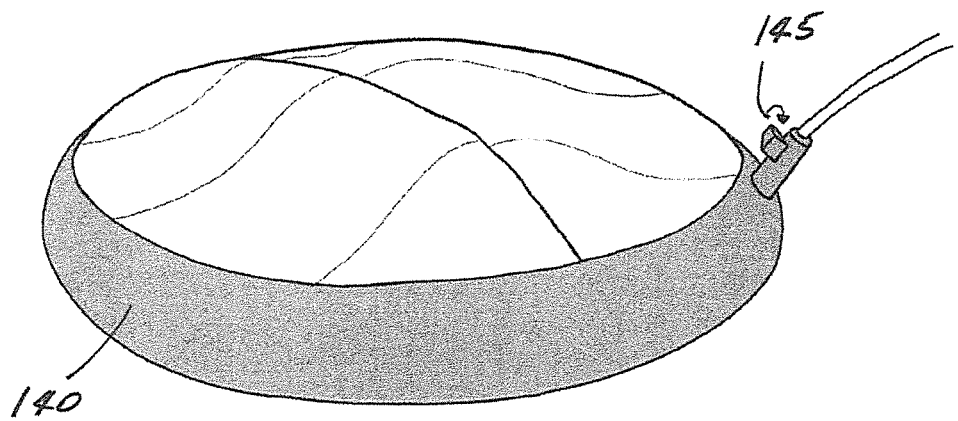
Figure 45:
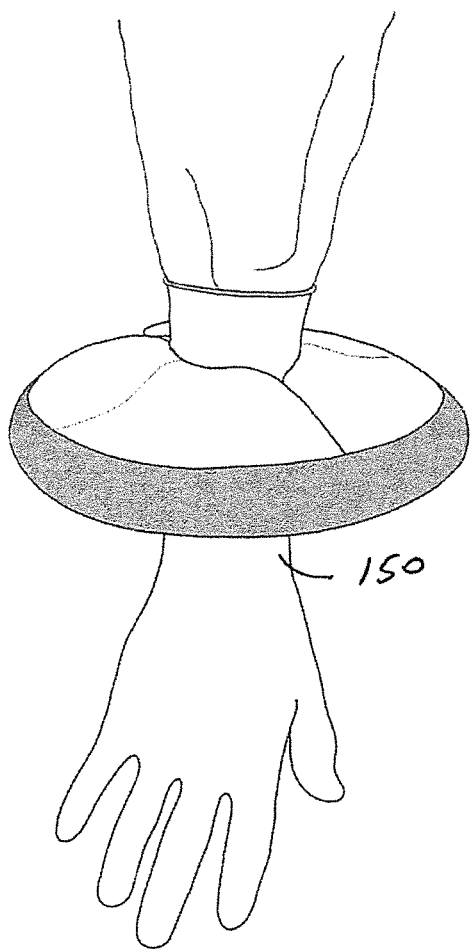
FIGS. 45 to 54 are a series of images that illustrate the hand access device of the invention in different configurations of use.
Figure 46:
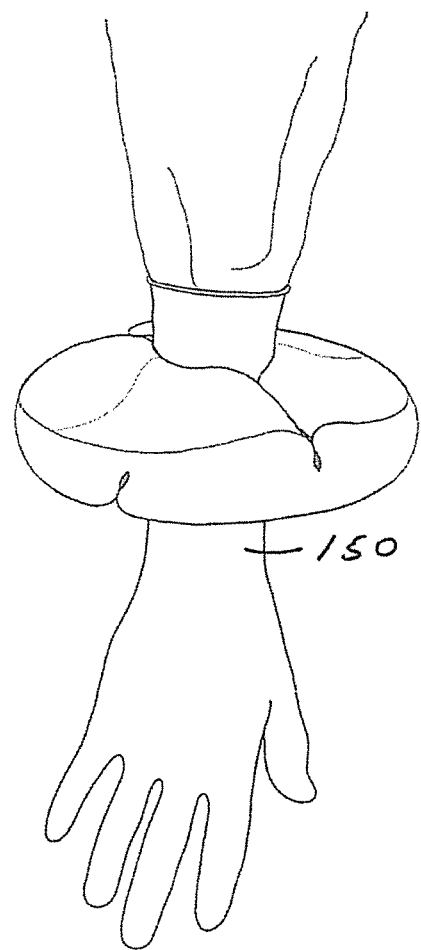
Figure 47:
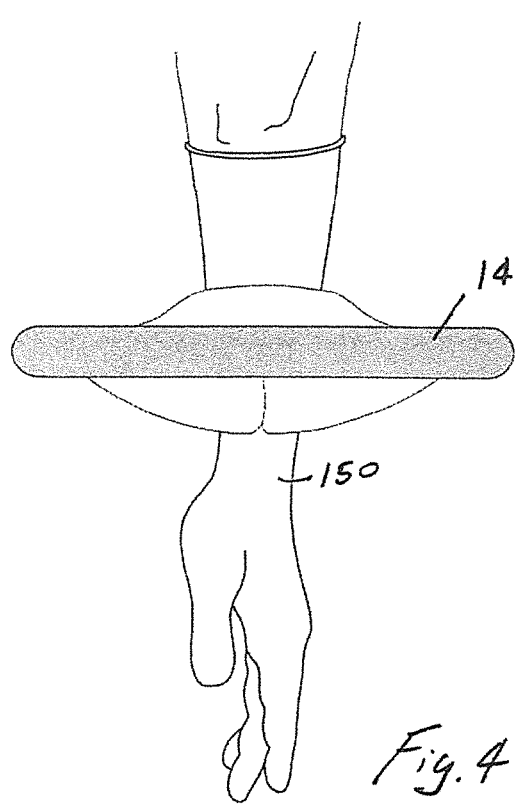
Figure 48:
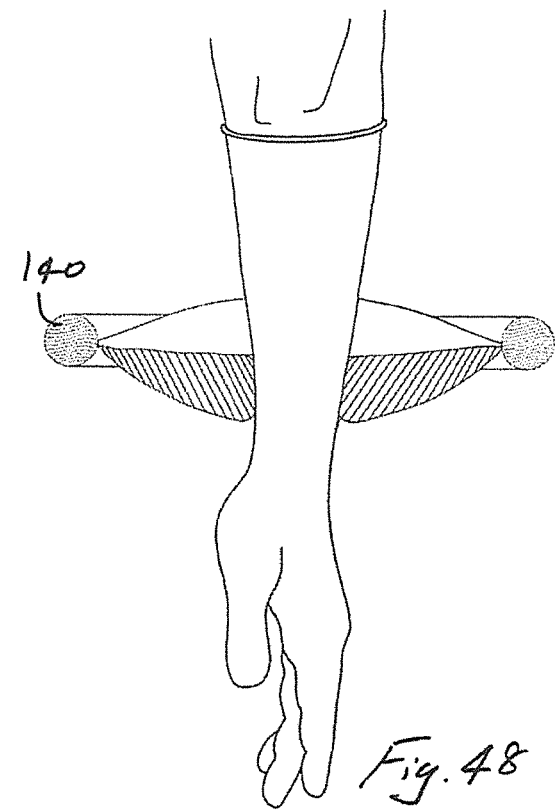
Figure 49:
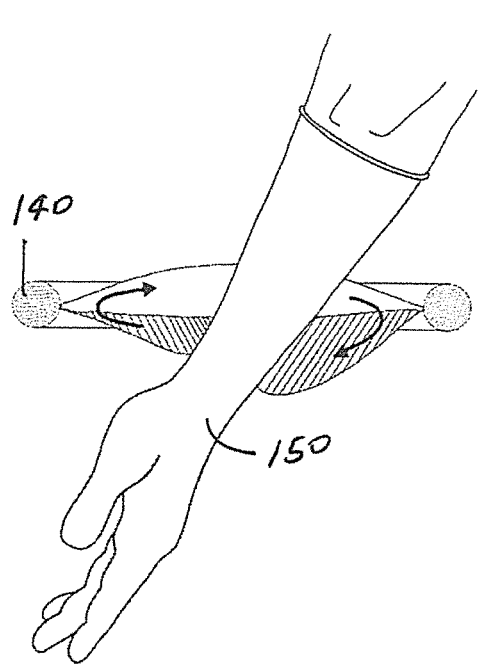
Figure 50:
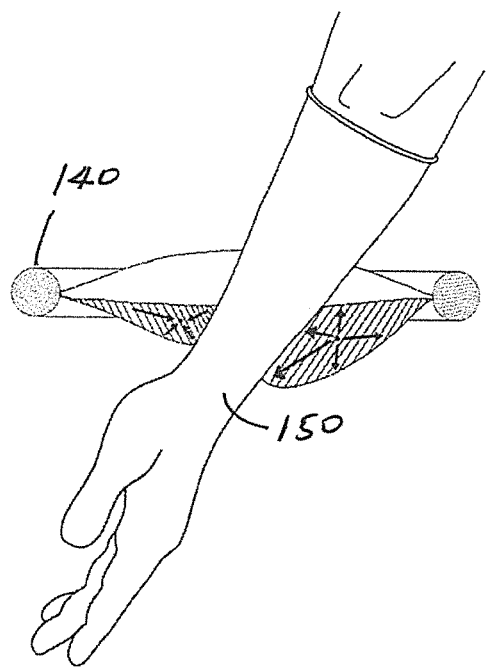
Figure 51:
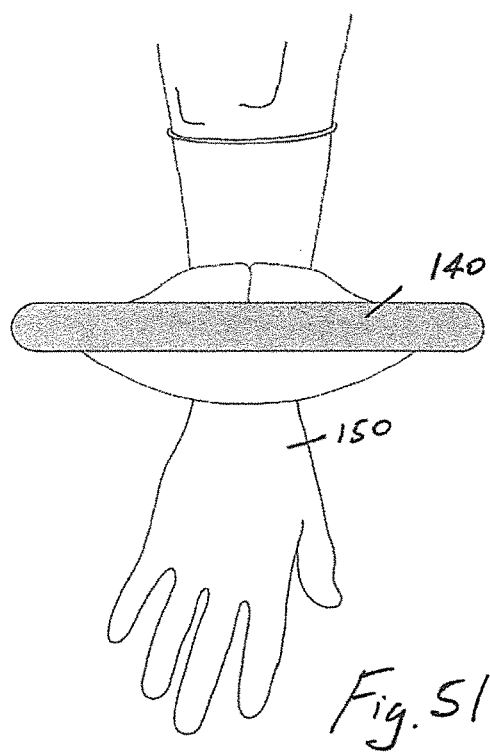
Figure 52:
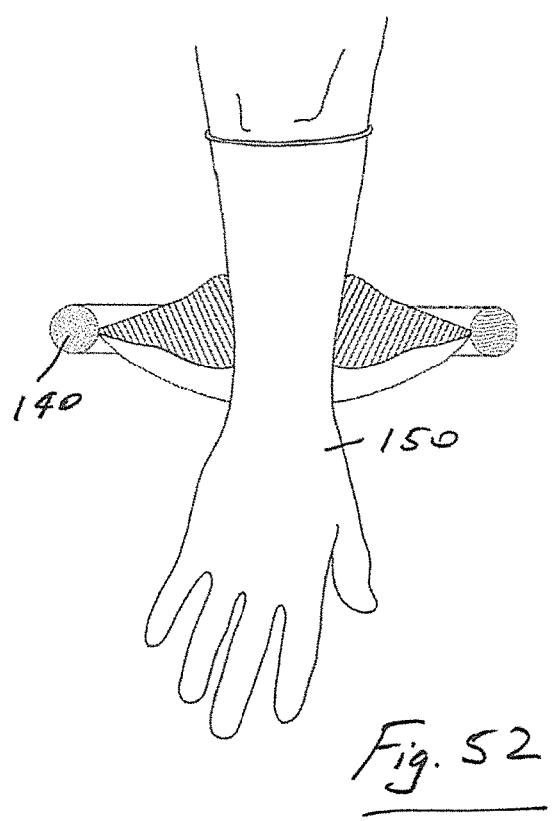
Figure 53:
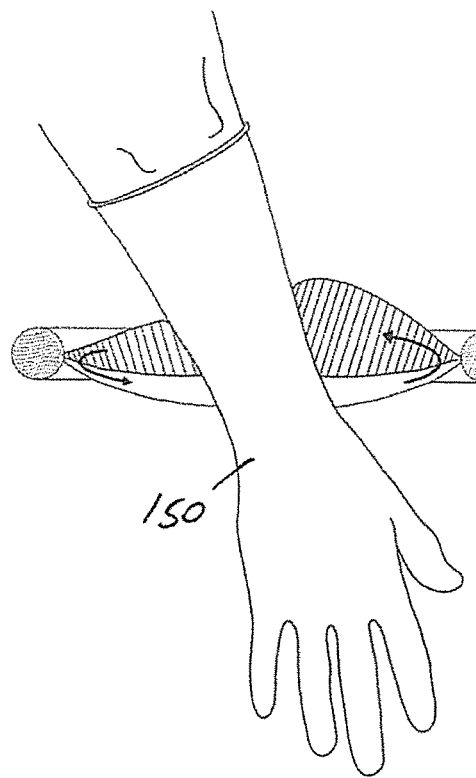
Figure 54:
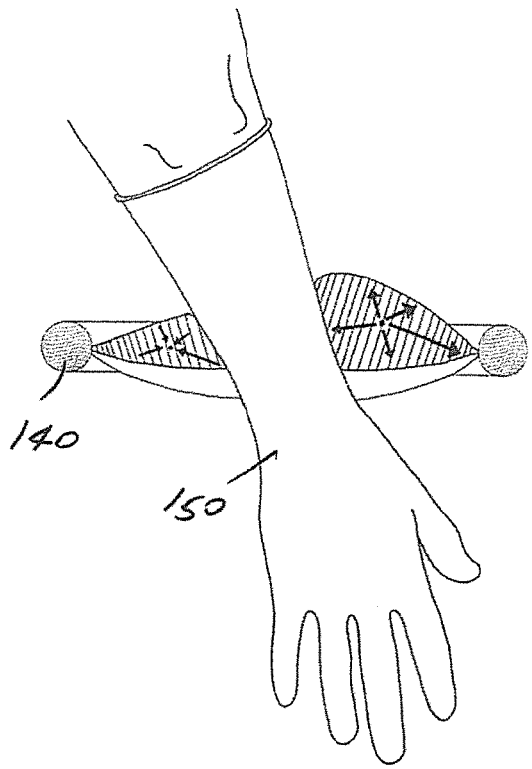
Figure 55:
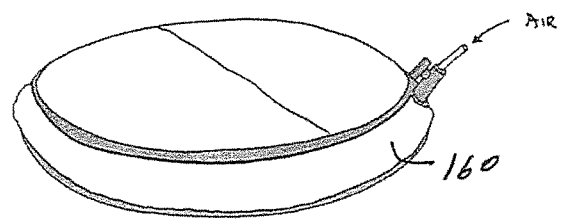
FIGS. 55 to 59 are various images of a hand access device including an overflow chamber.
Figure 56:
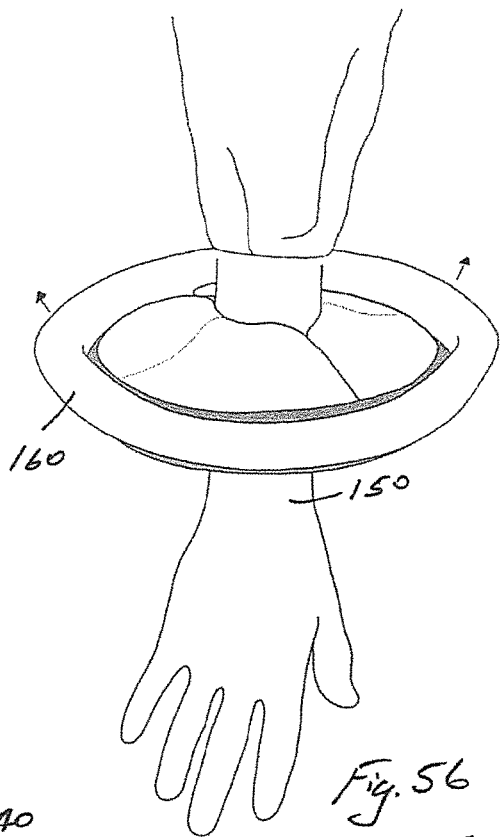
Figure 57:
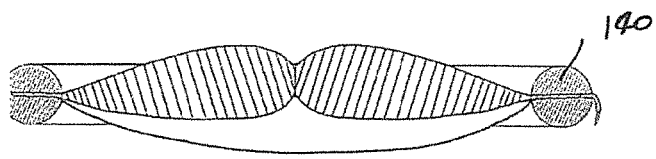
Figure 58:
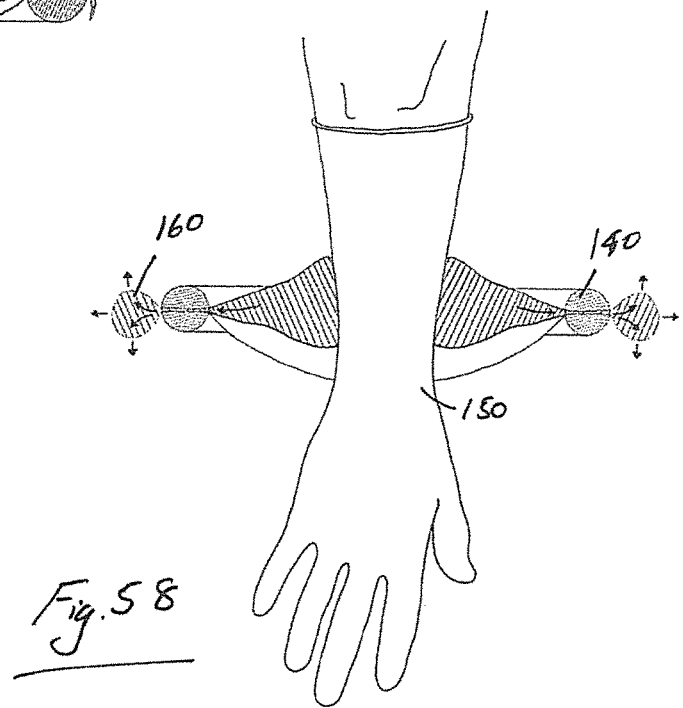

FIGS. 43 and 44 illustrate an outer casing 140 enclosing the edges of leaves. There are four overlapping leaves with the bottom two overlapping leaves perpendicular to the top two overlapping leaves. The casing allows air flow from one leaf to another via a fold enclosed within the casing. FIG. 43 shows the device in a non-inflated state and FIG. 44 shows the device in an inflated state with a luer lock (or any means of locking) valve/switch 145 to maintain inflation in the leaves. This air entry point could be used throughout the procedure if necessary to reduce or increase pressure. The valve functions as an effective zero-seal prior to hand insertion FIGS. 45 and 46 show a hand 150 in situ within an inflated device. The leaves readily deform to the geometry of the wrist in order to maintain a seal.

FIGS. 47 to 50 show the device function in use. With the hand in-situ in the valve the leaves have deformed to the wrist to form a wrist seal (similar in function to that of a lip seal). The difference between this wrist seal and a lip seal is that this wrist seal is highly flexible and extremely adaptable and caters for a wide range of movement and a wide range of wrist sizes. When the wrist is moved in any given direction the leaves accommodate the movement by moving air around into neighbouring leaves to equalise pressure and maintain the seal.

FIGS. 51 to 54 are similar to FIGS. 47 to 50 (but in the perpendicular plane) and illustrate the primary method by which the wrist seal is maintained throughout. When pressure is increased on/in one or more leaves, air is forced out of that particular leaf and into surrounding leaves where pressure is reduced by the same movement. This is illustrated by reducing and increasing in volume respectively and usually is most notable with opposing leaves (i.e. equal and opposite reaction). In this way it is believed that the pressure on the wrist is kept relatively constant and the seal is maintained through a wide range of positions and wrist sizes. Removal of the wrist returns the device to a zero seal.

FIGS. 55 to 58 illustrate a device including an overflow chamber 160. In this embodiment, instead of air moving between leaves when pressure is increased in areas of the system the air moves into an additional overflow chamber that may be of same or different material. It keeps the leaves independent from one another while still embodying the adaptability and constant pressure wrist seal.

Figure 59:
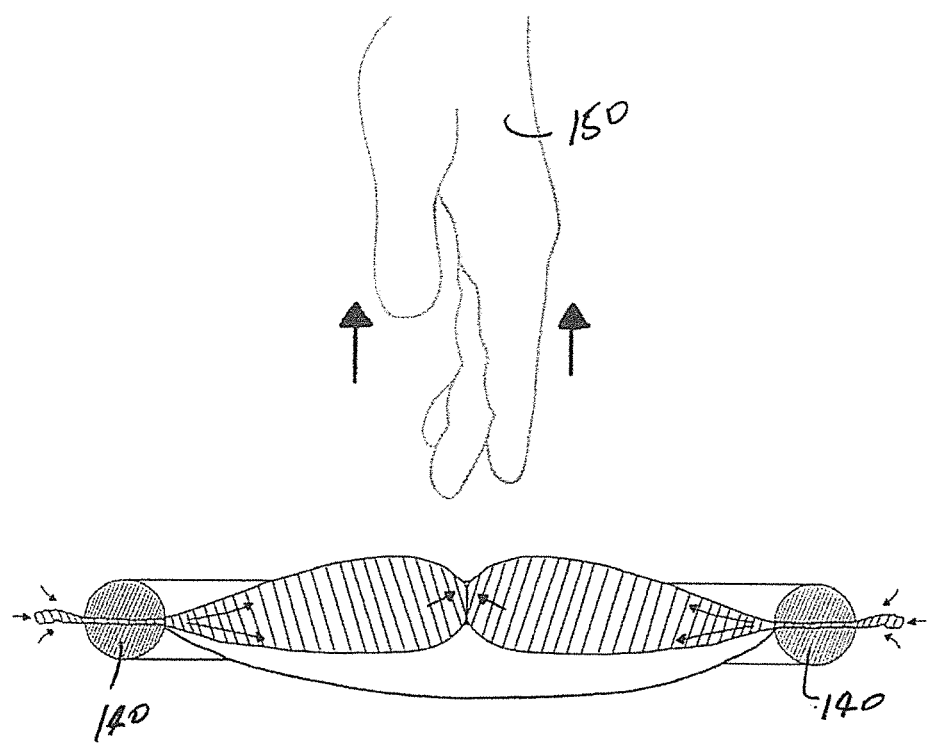

FIG. 59 illustrates an arrangement in which, once the hand 150 is removed from the valve, the air flows back out of the overflow chamber into the valve leaves once more. Air is biased to remain fully largely within the primary sealing leaves unless pressure is exerted on them. When this external pressure is removed the bias is on the air to expel from the overflow chamber in order to reset the zero seal. This bias can be created through many means. In the example to the left the overflow chamber has inherent elasticity. The overflow chamber could be a different material or be biased by any number of mechanical means.

FIGS. 60 and 61 illustrate an example of a mechanical biasing system in which a built in mechanism, that is not limited to the arrangement shown including a push plate 170 and a spring 171, is incorporated to resist inflation of the overflow chamber 160 up to a certain pressure and also re-inflate the leaves on removal of hand or instrument. Other means to create a mechanical bias may include additional elasticated resistance, sprung metal or plastic, hydraulics and the like.

Figure 62:
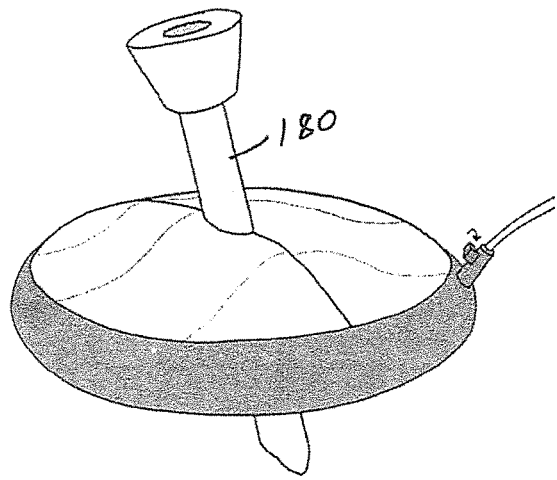
FIGS. 62 to 69 illustrate various hand access devices suitable for use with trocars.

FIG. 62 shows the system similarly compatible with trocars 180 whereby trocars 180 are inserted in the same manner as the hand and wrist, through the sealing leaf system.

Figure 63:
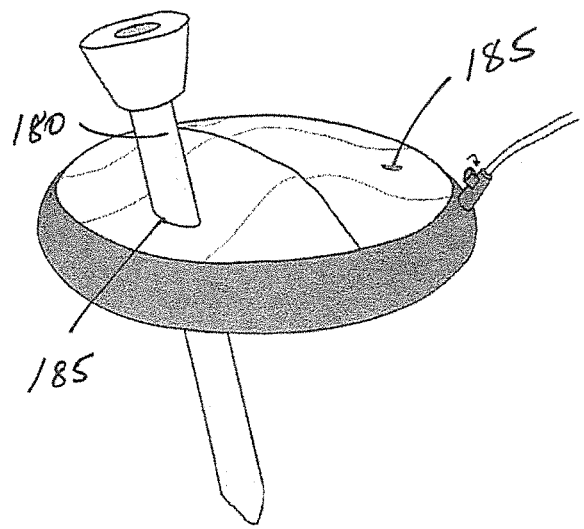

FIG. 63 shows an arrangement in which a trocar 180 is inserted through one or more leaves offset from the main sealing point through a sealed channel/chute 185.

Referring to FIGS. 62 and 63 the chutes 185 can self-close under inflation pressure in somewhat of a circumferential diaphragm manner or could have their own inflatable walls that constrict against any leak.

Figure 64:
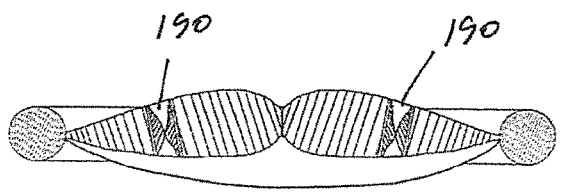
Figure 65:
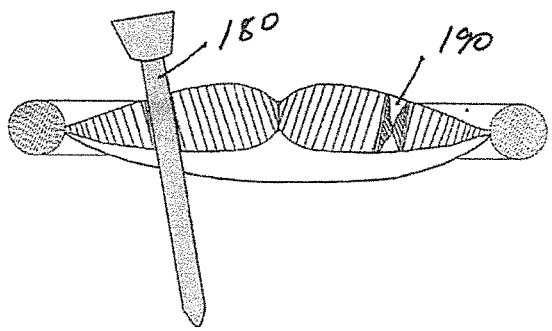
Figure 66:
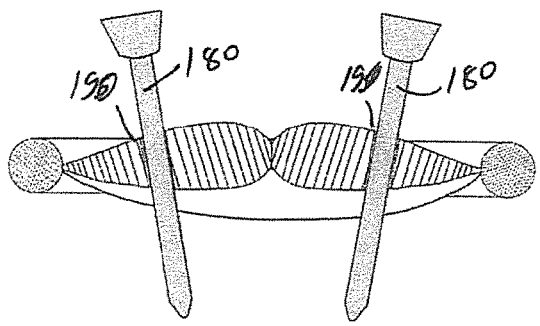

FIGS. 64 to 66 show an embodiment of a sealing chute 190 that is built into the leaf system that seals effectively when the system is inflated (i.e. zero valve) but allows a trocar 180 to pass through when required. The channel/chute 190, due to circumferential pressure from the volume of air in the leaf, seals against the trocar or instrument 180. The chutes 190 can vary in size to accommodate all sizes of instruments and can appear in multiples. The leaves can accommodate numerous instrument chutes each or between them, and therefore facilitate multi-port procedures.

Figure 67:
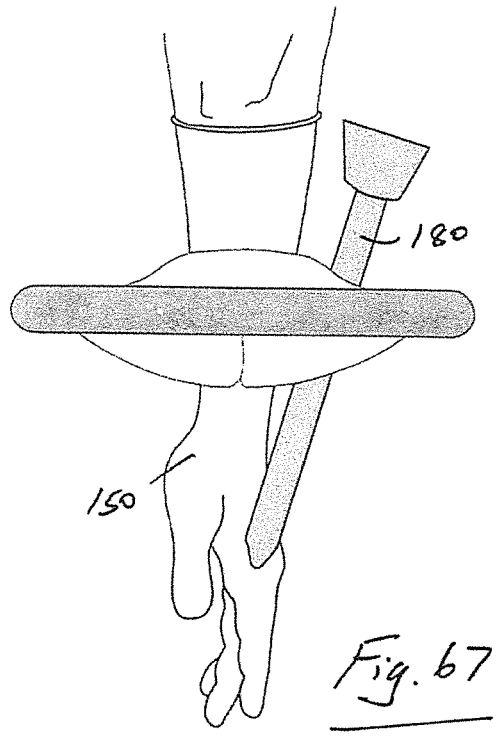

FIG. 67 shows that offsetting instrument chutes 190 facilitates introducing one or more trocars 180 at the same time as hand or other instrument insertion.

Figure 68:
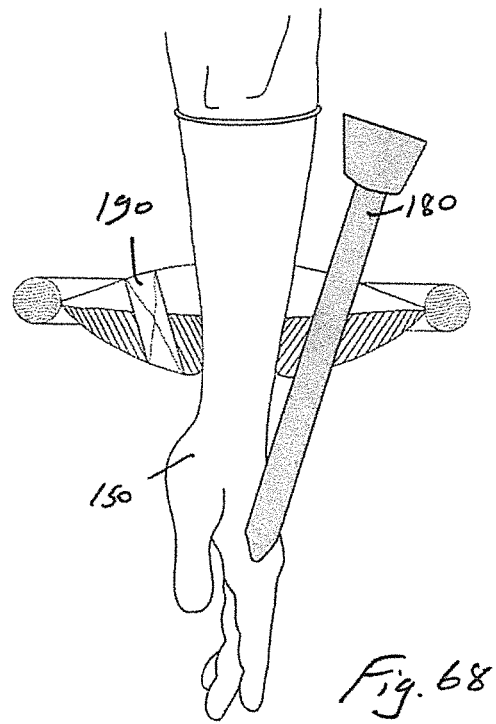
Figure 69:
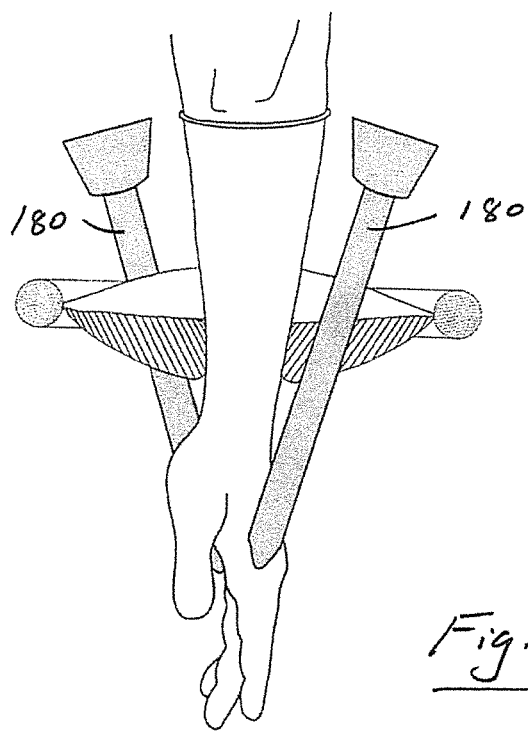

FIGS. 68 and 69 illustrate how both hand 150 and trocar 180 can be accommodated at the same time. The system could also accommodate instruments directly through the chutes 190 rather than needing insertion of a trocar first.

Figure 70:
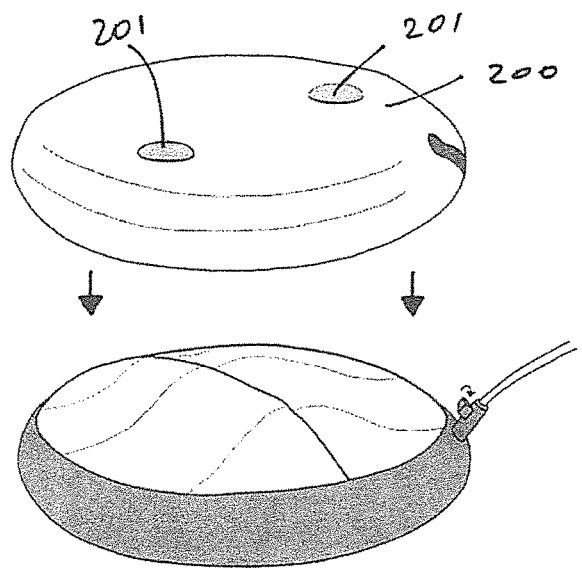
FIGS. 70 to 73 show a hand access device and a valve cap having valves through which instruments may be inserted.
Figure 71:
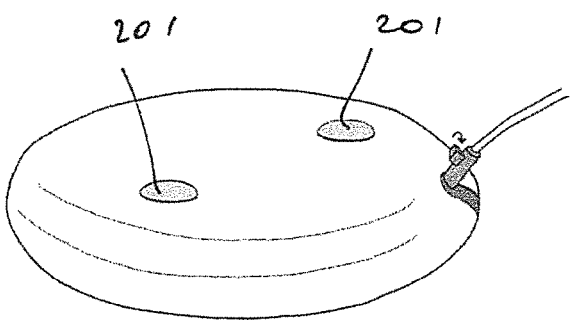

FIG. 70 illustrates the addition of a valve cap 200 with built-in instrument valves 201. The cap 200 may go over a leaf valve system while deflated or inflated and could be implemented in a wholly modular system which can readily and easily switch between hand access and multi-port surgery Referring to FIG. 71 the valve cap 200 may have at least one instrument valve 201 and up to however many are necessary and can vary in size to cater for any instrument. The valve cap 200 may remain locked in situ over the device casing as long as is necessary. Locking could be achieved via a friction fit, screw fix, snap fit or any other suitable means.

Figure 72:
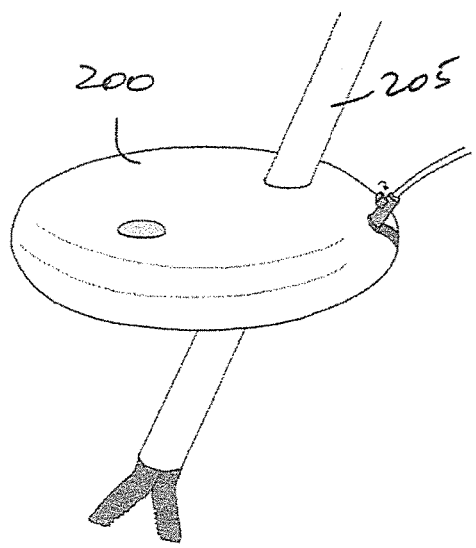
Figure 73:
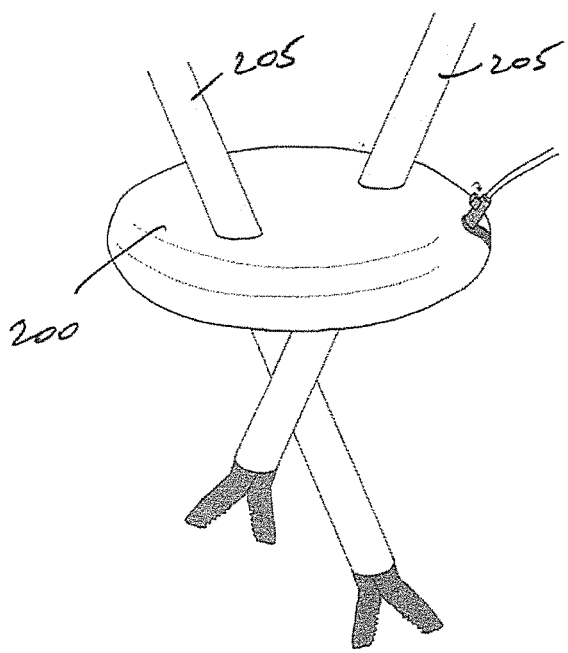

Referring to FIGS. 72 and 73 when in place, the cap 200 can be used to insert one or more instruments 205 of various size while sealing effectively against gas leak. Each valve may have a zero seal.

Figure 74:
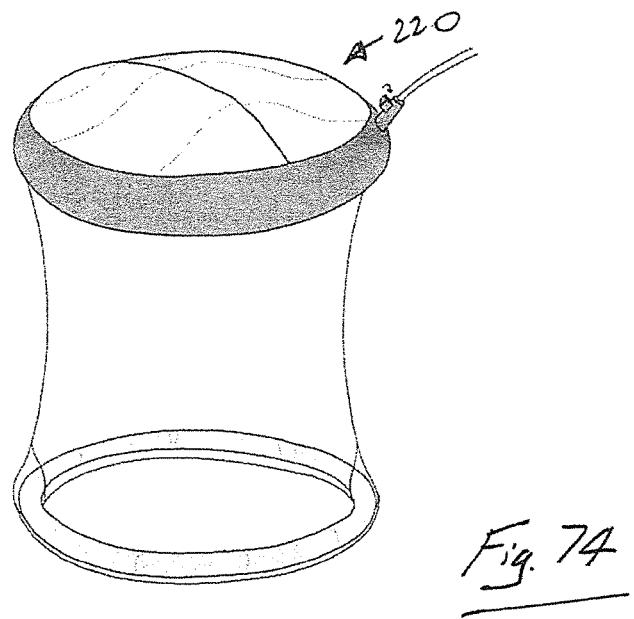
FIGS. 74 to 77 illustrate a hand access device of the invention and an associated retractor.

FIG. 74 illustrates the device in use with a wound retractor system 210. The system may be completely independent from the valve system 220 on top or may be inter-connected or part thereof. For example, the retraction sleeve may be an extension of the material piece used to create the leaves in the valve system. The wound retraction sleeve may be double-walled and inflatable in order to aid retraction and could therefore also be connected to the valve leaves either directly or via an additional air chute. In another embodiment the inflatable retraction sleeve could serve as the 'overflow chamber' as mentioned in previous embodiments. In this particular embodiment the externally applied force to expel from the overflow chamber could in fact be the tension in the wound/incision itself.

Figures 75, 76, 77:
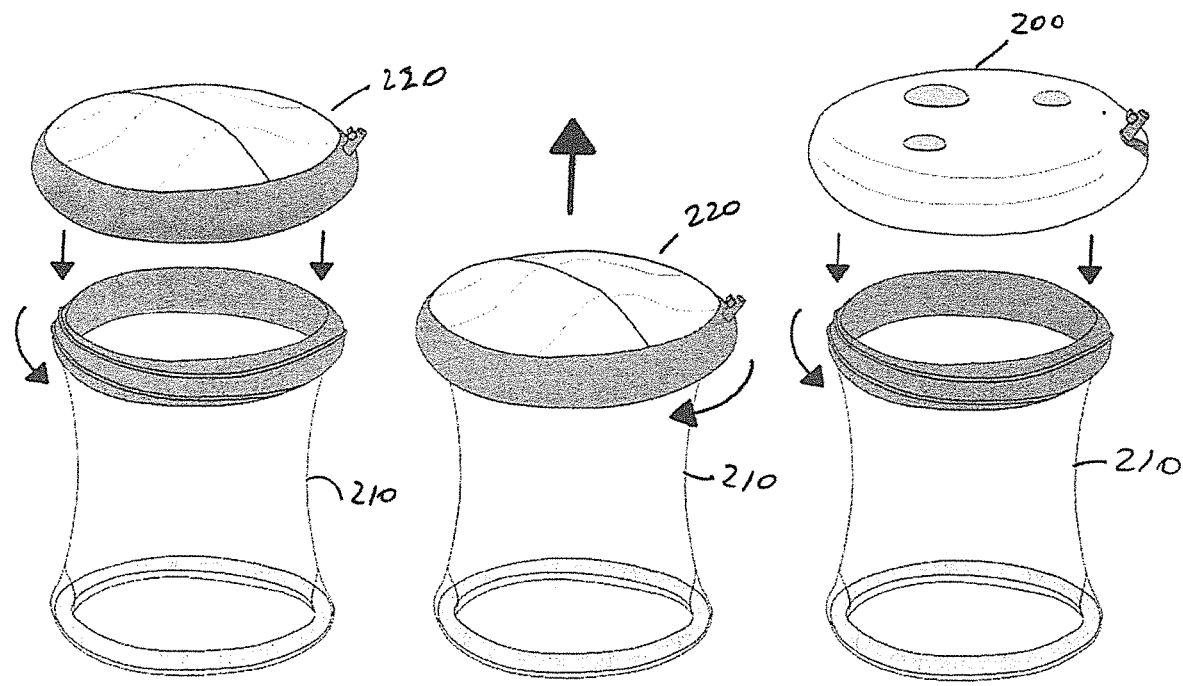

FIGS. 75 to 77 illustrate a modular device which in this case comprises two separate and completely independent valve caps 220, 200 that readily remove and attach by means of a simple locking system (screw thread illustrated but not limited to this means). In order to switch between single port surgery and hand access, one cap is removed to be replaced by the other. A wound retractor 210 can also be used in a deflated abdomen without any valve cap in order to remove tissue, for example.

Figure 78:
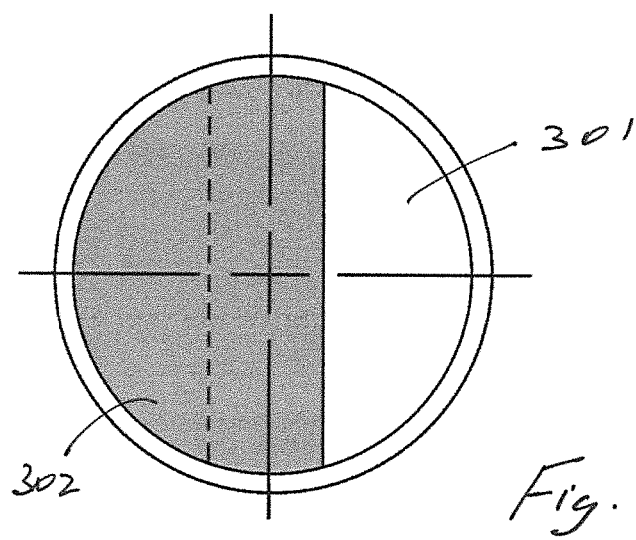
FIGS. 78 and 79 are plan and side cross sectional views illustrating an overlap.
Figure 79:
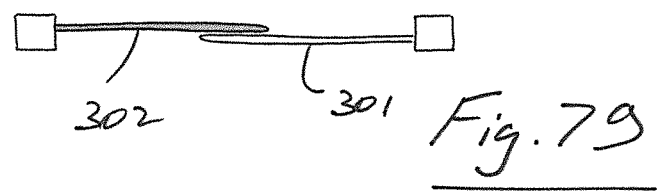

FIGS. 78 and 79 illustrate a hand access device comprising two leaves or chambers 301, 302 which are overlapped. The overlap in some cases may vary. The overlap in some cases may be from 20 mm to 40 mm. In one case the overlap is about 30 mm.

Figure 80:
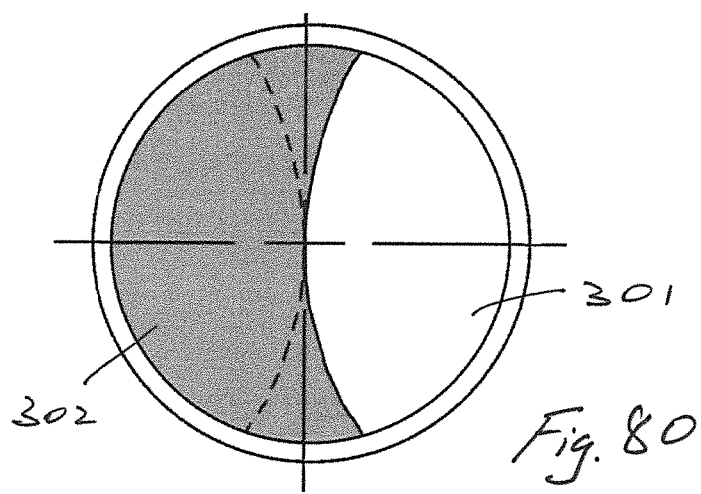
FIGS. 80 and 81 are plan and side cross sectional views illustrating the change in the overlap as the valve inflates.
Figure 81:
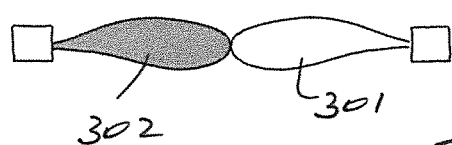

FIGS. 80 and 81 illustrate what happens to the overlap of one leaf of the device as it inflates. The chambers 301, 302 move into sealing engagement on inflation.

Figure 82:
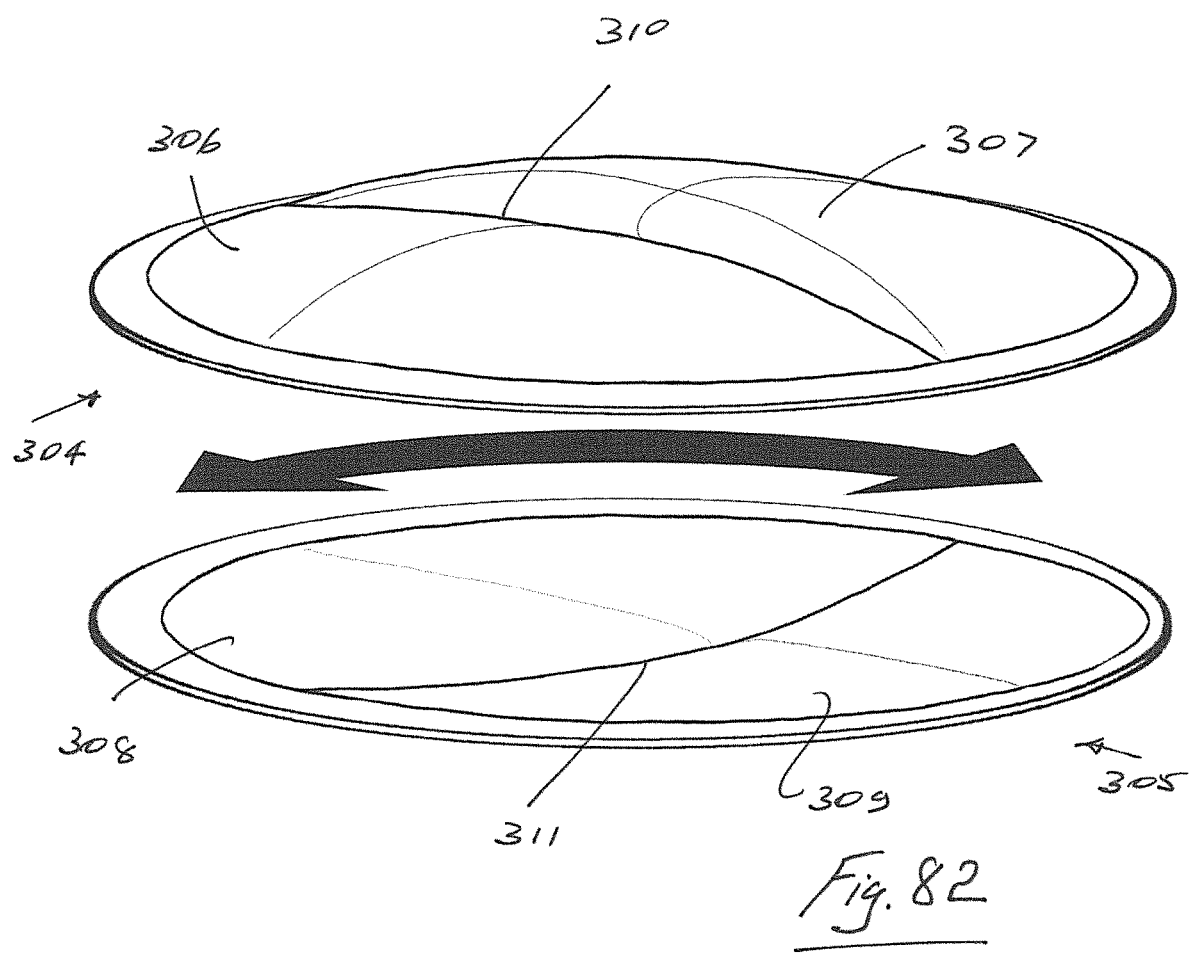
FIG. 82 illustrates a range of relative rotation between two valves.

FIG. 82 is a partially exploded view of a hand access device comprising two layers 304, 305. Each layer comprises two overlapping leaves 306, 307 and 308, 309. There is an overlap zone 310 between the leaves 306, 307 of one layer 304 and an overlap zone 311 between the leaves 308, 309 of the second layer 305. The overlap zones 310 and 311 are offset in relation to each other. The offset angle may be any suitable angle greater than 0° and less than 180°. For example, the angle may be from 5° to 175°, 10° to 170°, 15° to 165°, 20° to 160°, 25° to 155°, 30° to 150°, 35° to 145°, 40° to 140°, 45° to 135°, 50° to 130°, 55° to 125°, 60° to 120°, 65° to 115°, 70° to 110°, 75° to 105°, 80° to 100° or 85° to 95°.

Figure 83:
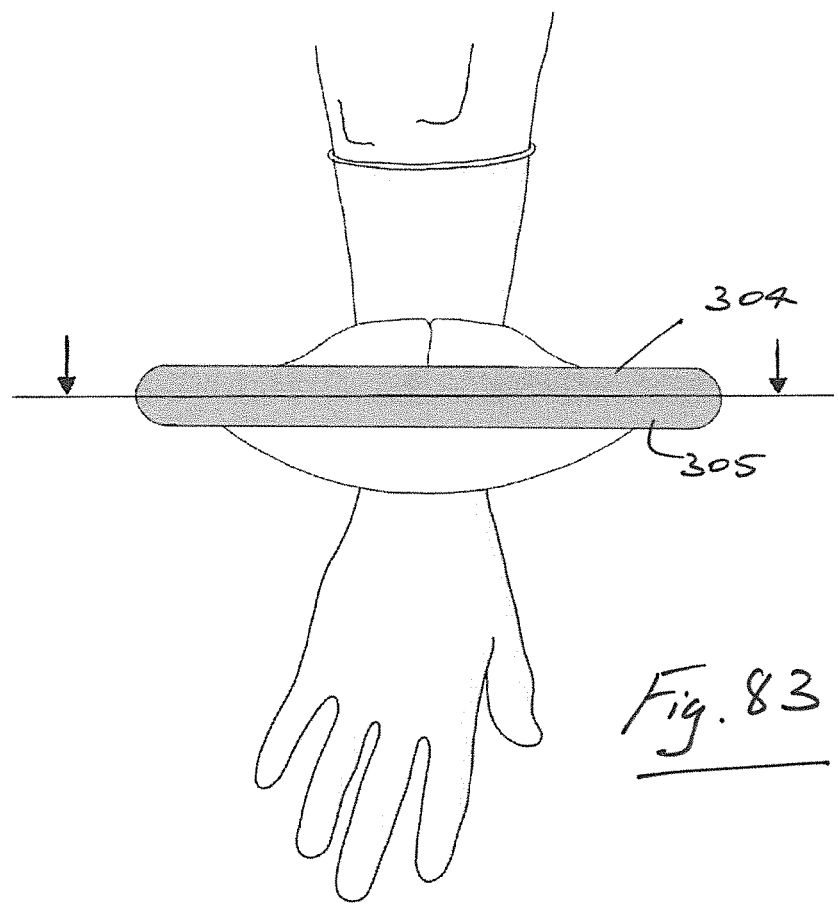
FIGS. 83 and 84 illustrate a device with a wrist in situ.
Figure 84:
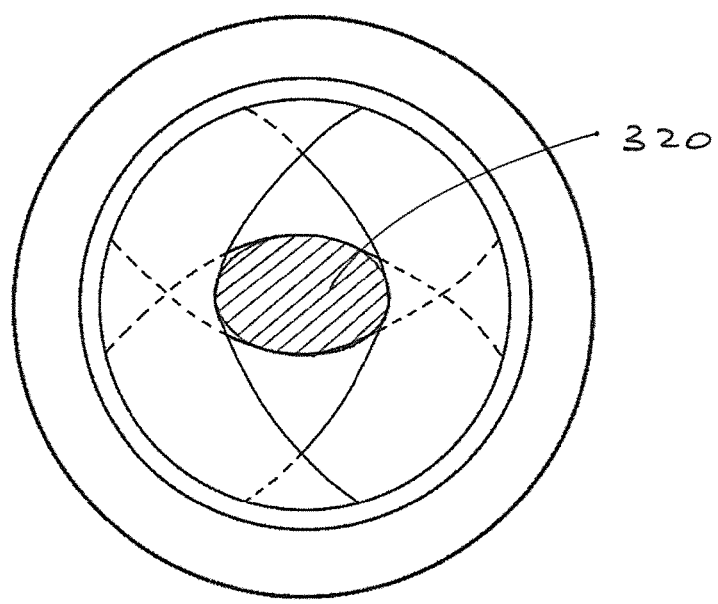

FIGS. 83 and 84 illustrate a hand access device comprising two layers 304, 305 with a wrist 320 is in situ. The close sealing to the wrist will be noted.

Figures 85A, 85B:
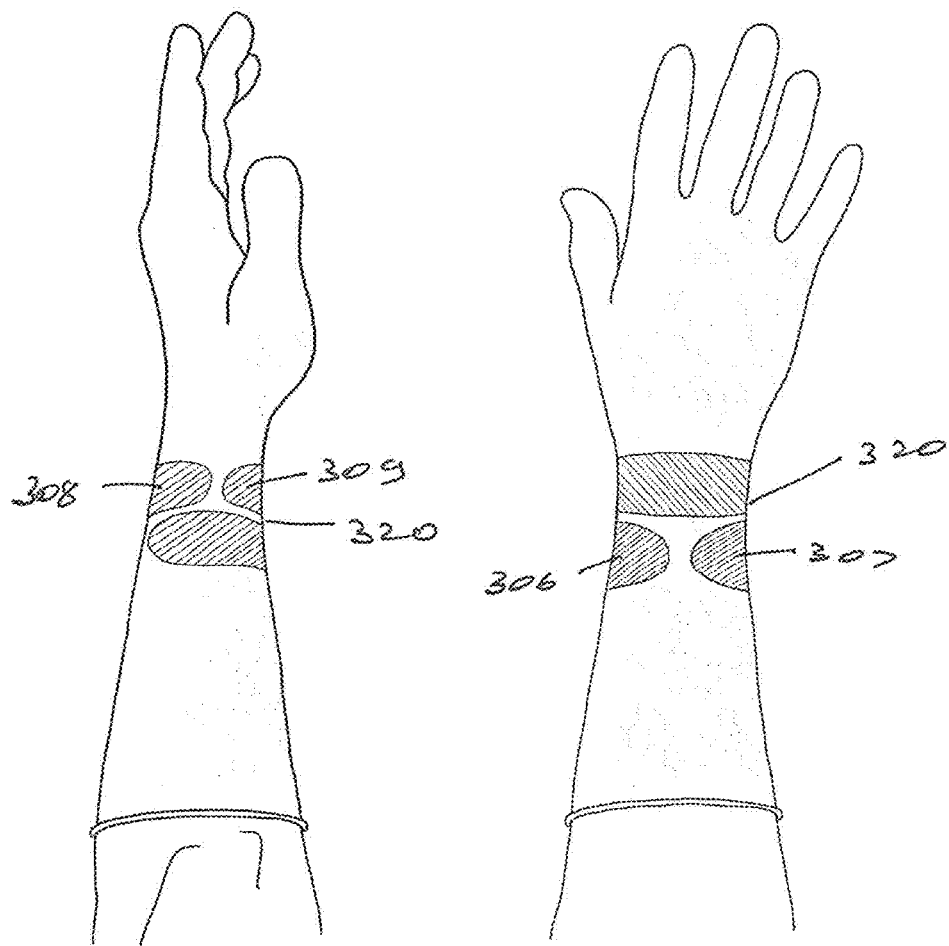
FIGS. 85(a) and 85(b) illustrate a surgeons arm and wrist with overlapping valves in situ.

FIGS. 85(a) and 85(b) illustrate the sealing engagement to an object, in this case a surgeon's wrist inserted through the region of overlap. It will be noted that due to the layout of the leaves, they do not strangulate the wrist, allowing a blood flow path which reduces the chance and severity of tingling in the user's fingers and makes the valve more comfortable to use over a longer period of time. The device can be rotated around to move the pressure points if, over time, the pressure points become uncomfortable. The surgeon can also adjust the pressure in the leaves of the device to suit their needs by adding or releasing air via an inflation port.

It will be noted that the layers or chambers/leaves are axially spaced-apart relative to an object such as a surgeons arm inserted through the offset overlap zones.

The hand access device according to the invention may include an additional sealing layer as a means to further improve sealing at extreme positions of a surgeons arm. This may also act as a safety/back-up feature in the unlikely event of a major leak path occurring—for example due to puncturing of one or more of the leaves. The additional safety layer may be of any suitable type and/or material and may be non-inflating. Some examples include overlapping sheets, non-overlapping sheets, an overlap sheet or a lip seal. Such an additional sealing layer may be juxtaposed to one of the other layers (such as an inflatable layer) described herein.

Figure 86:
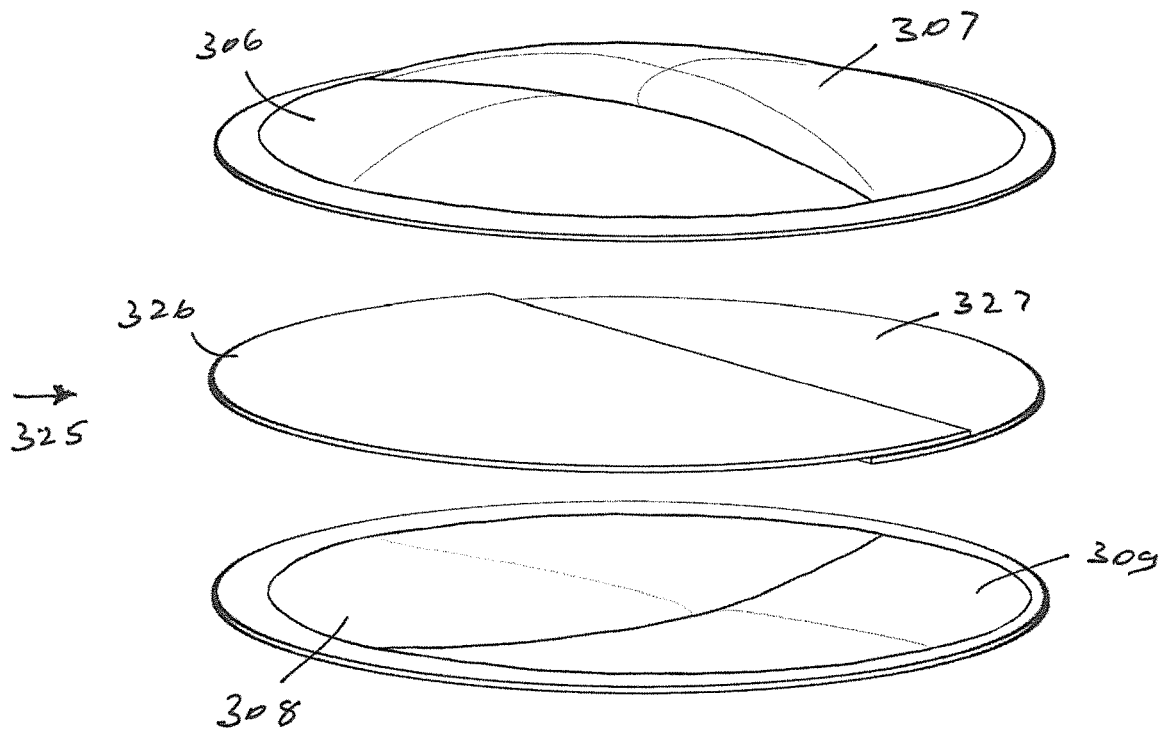
FIGS. 86 and 87 are exploded views of devices according to the invention with an additional layer in place.
Figure 87:
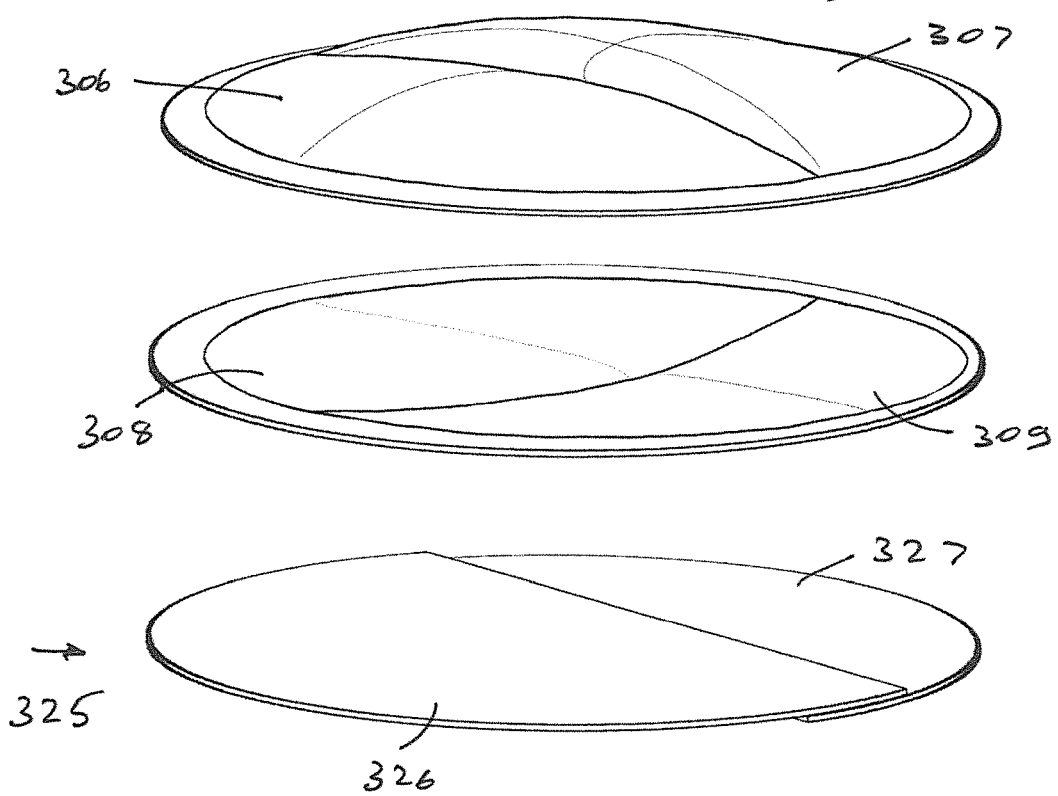

Referring to FIGS. 86 and 87 in these cases a hand access device has an additional overlap sealing layer 325 comprising two or more overlapping sheets 326, 327. In the arrangement illustrated in FIGS. 86 and 87 the additional overlap sealing layer 325 is located between and juxtaposed to the upper layers of leaves 306, 307 and the lower layer of leaves 308, 309.

In the arrangement illustrated in FIG. 87 the additional overlap sealing layer 325 is located below the lower layer of leaves 308, 309.

For ease of use, the overlap between the sheets 326, 327 may be orientated in line with the overlap of the upper or lower leaves or offset therefrom.

Referring to FIGS. 88 and 89 there is illustrated hand access devices with another additional sealing layer similar to FIGS. 86 and 87. In this case the additional valve 330 comprises sheets 331, 332 which are not overlapped. Instead there is a gap therebetween that does not cause pressure on an inserted wrist but still serves to significantly reduce leakage at extreme positions/angles of use.

Figure 90:
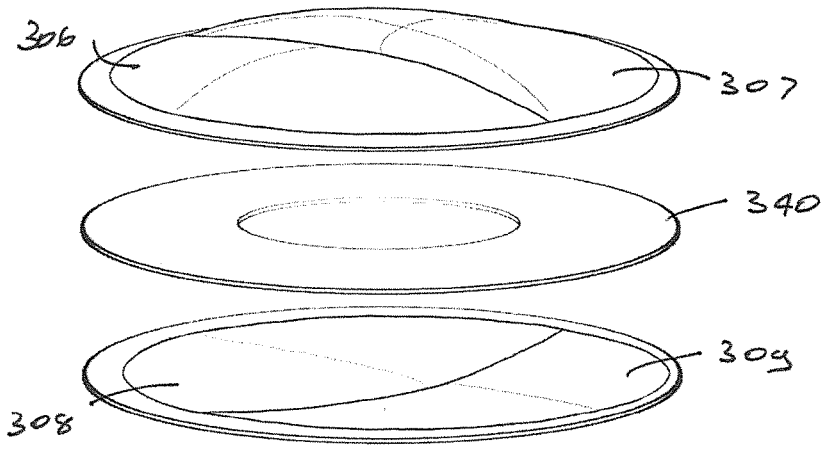
FIGS. 90 and 91 are exploded views of further devices with a lip seal sheet in place.
Figure 91:
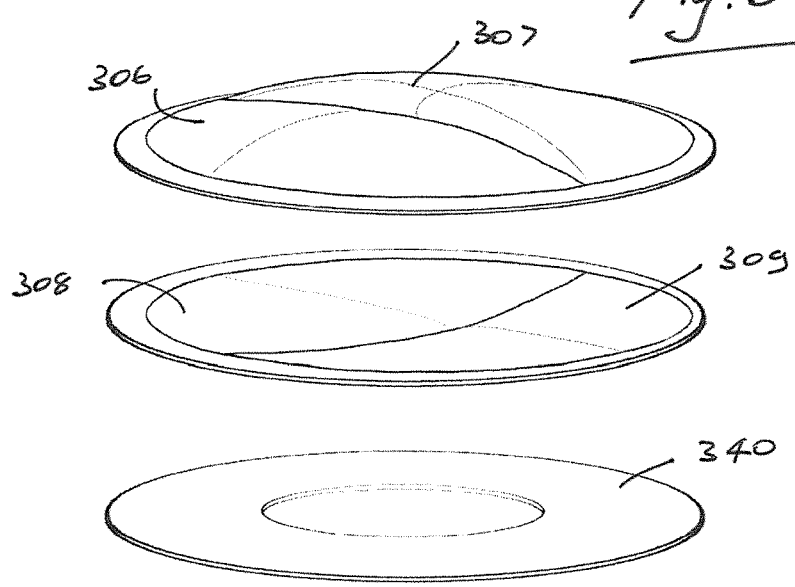

FIGS. 90 and 91 illustrate an additional non-inflating sealing layer—in this case a lip-seal sheet 340—that plugs catastrophic leak path without causing any pressure on the wrist—can be located between layers (FIG. 90) or below layers (FIG. 91).

Figure 92:
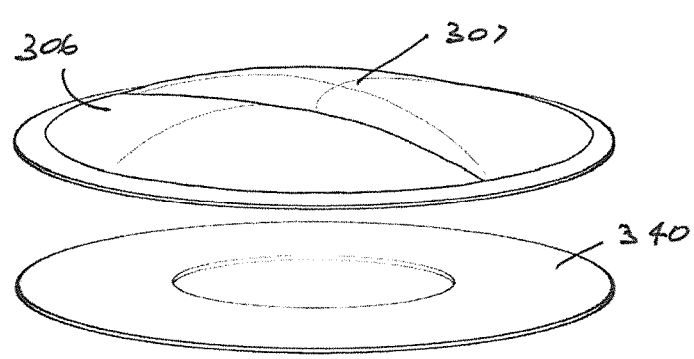
FIG. 92 is an exploded view of another device with one valve layer and a lip seal layer.

FIG. 92 illustrates an additional non-inflating layer—lip-seal sheet 340—with just one layer of leaves (the additional valve layer acts as zero seal—lip seal and seals when a wrist is in place.

Figure 93:
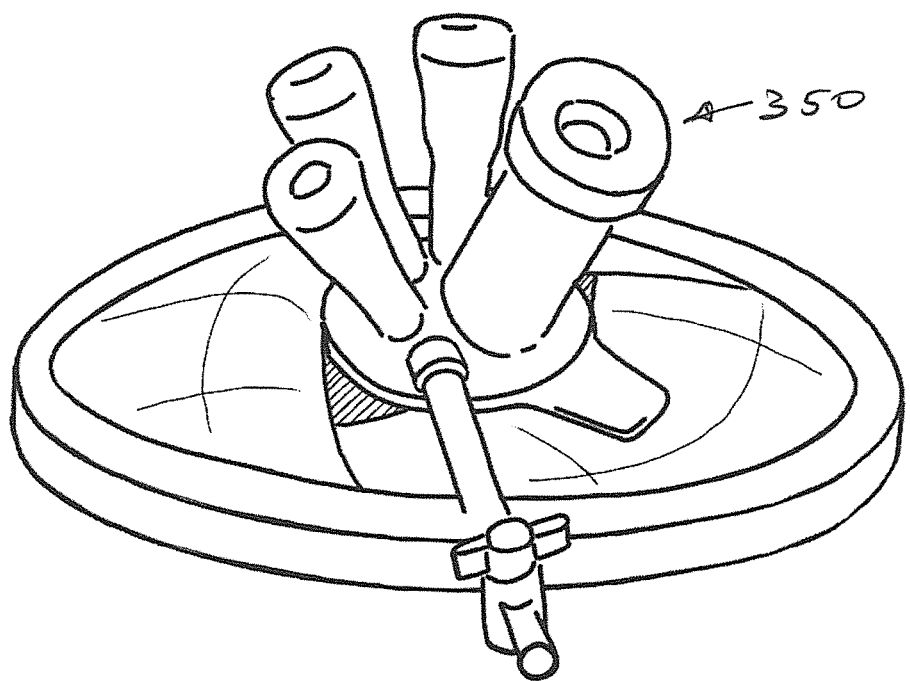
FIGS. 93 and 94 are isometric and cross sectional views of a device of the invention with an instrument port and base retractor in place.
Figure 94:
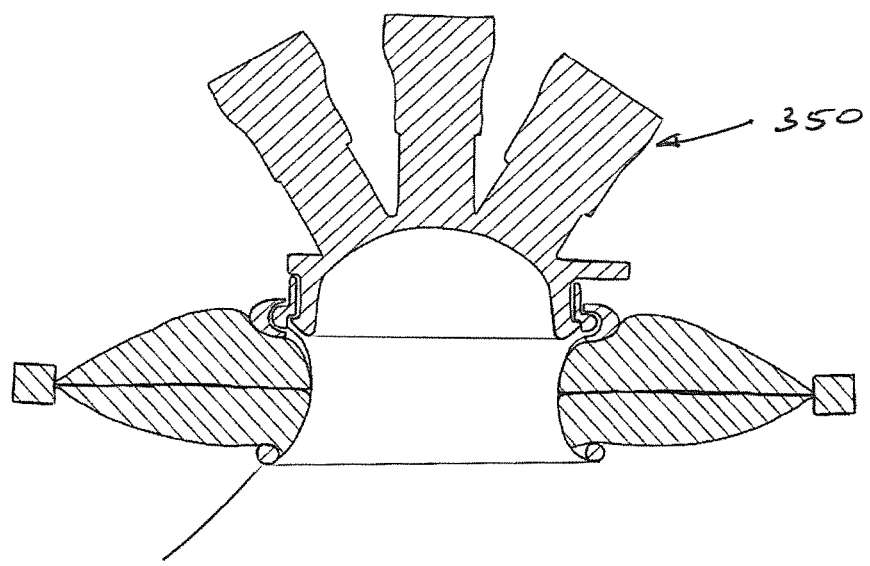

FIGS. 93 and 94 illustrate the device of the invention used with an instrument access port 350 and a base retractor 351.

The instrument access port may be of any suitable type such as those described in our U.S. Pat. No. 7,195,590, U.S. Pat. No. 7,998,068, U.S. Pat. No. 8,465,494, U.S. Pat. No. 8,021,296, U.S. Pat. No. 8,187,178 and/or U.S. Pat. No. 8,657,740, the entire contents of which are incorporated herein by reference.

The retractor may also be of any suitable type such as those described in our U.S. Pat. No. 6,846,287, U.S. Pat. No. 6,254,534, and/or U.S. Pat. No. 7,599,893, the entire contents of which are incorporated herein by reference.

As described above an air flow path may be provided between the chambers/leaves within a layer and/or between layers in a number of different ways.

Figure 95A:
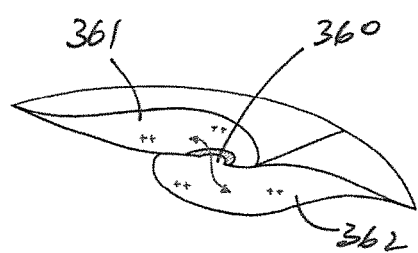
FIGS. 95(a) and 95(b) illustrate flow path configurations between chambers.
Figure 95B:
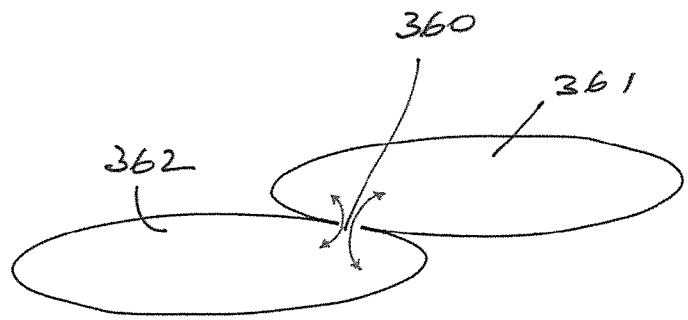

FIGS. 95(*a*) and 95(*b*) illustrate flow path configurations between leaves/chambers of some hand access devices of the invention. In this case, chamber walls are attached, such as welded to each other and a hole 360 is punctured through to facilitate air flow between the leaves 361, 362.

Figure 96A:
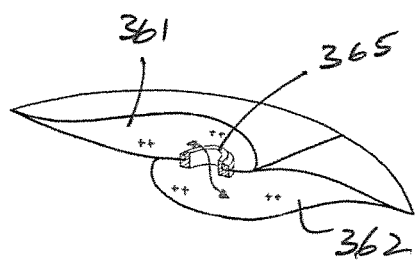
FIGS. 96(a) and 96(b) illustrate the use of a rivet to puncture and seal the flow path.
Figure 96B:
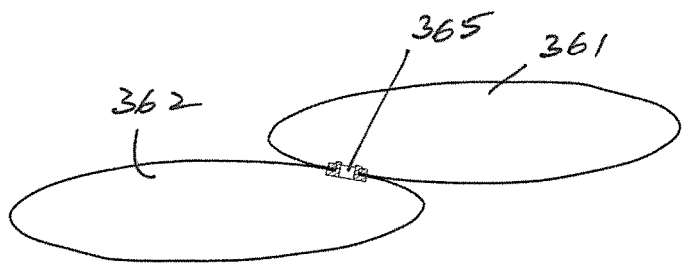

FIGS. 96(*a*) and 96(*b*) illustrate a moulded rivet type component 365 that may be used to puncture and seal the flow path.

As described above, the hand access devices of the invention may include secondary ports which may be used for various purposes such as for instrument access and/or for a probe such as a camera.

FIGS. 97 and 98(*a*) to 98(*d*) illustrate secondary valve locations/configurations 370. The secondary valves may be located within the leaves (FIGS. 97, 98(*a*), 98(*b*)) or may extend through the device housing as illustrated in FIGS. 98(*c*) and 98(*d*).

FIGS. 99 and 100 illustrate a secondary valve utilising a flap 380 configuration and a reinforced hole 381. The flap may be made from the same material or a tougher material to that used in the valve. The hole 381 is reinforced with a more rigid material to prevent tearing. The flap 380 is held in place below the hole 381. Passage of an instrument moves the flap 380 to the side during use and the flap 380 moves back into a zero seal position under the pressure of insufflation in the abdomen when the instrument is removed.

FIG. 101 illustrates a hand access device having a housing 385 that includes a means through which to inflate the valve system. The inflation system may consist of tubing, luer connector and the like. The entire valve may be inflated through one single attachment point 386 on the housing 385. Similarly, the valve could be inflated through one or more attachment points through the housing and each layer and/or chamber could be inflated independently. For example there may be up to 4 inflation points for a four chamber valve, up to 6 inflation points for a 6 chamber valve.

FIGS. 102 to 104 show a valve housing 390 which contains a conduit/airtight piping system 391 which serves to circulate air from one chamber to another and from layer to layer rather than connecting chambers directly. The housing 390 serves the same function as the airflow connection in previous embodiments but in this case the leaves need not be physically bound to one another. Instead, all air transfer may occur through the housing.

Figure 105:
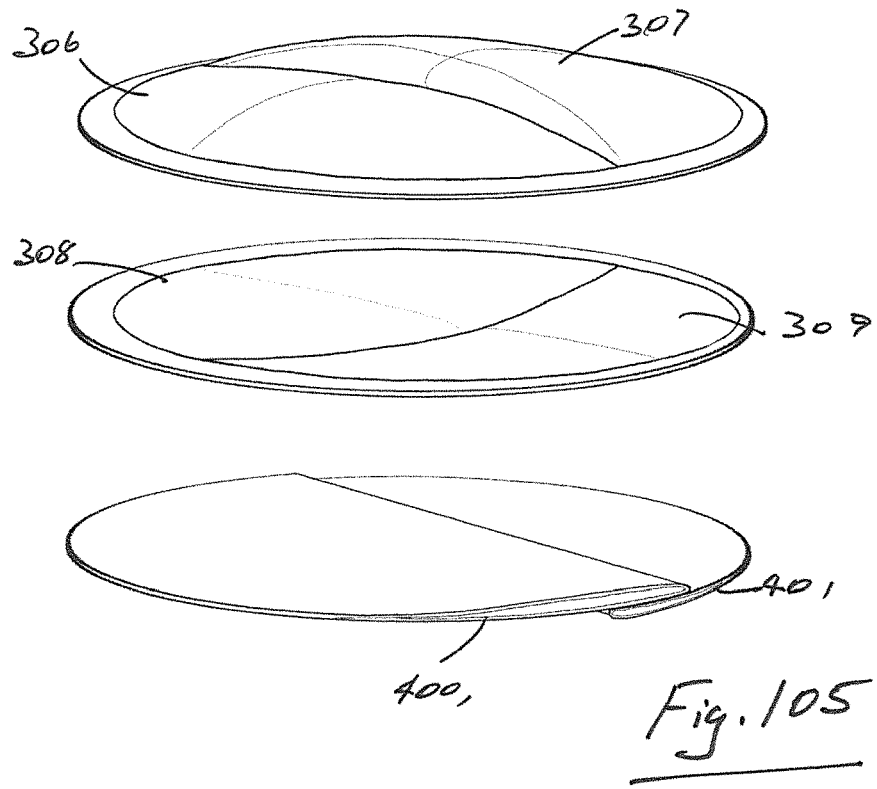
FIGS. 105, 106 and 107 are exploded views of further devices according to the invention.
Figure 106:
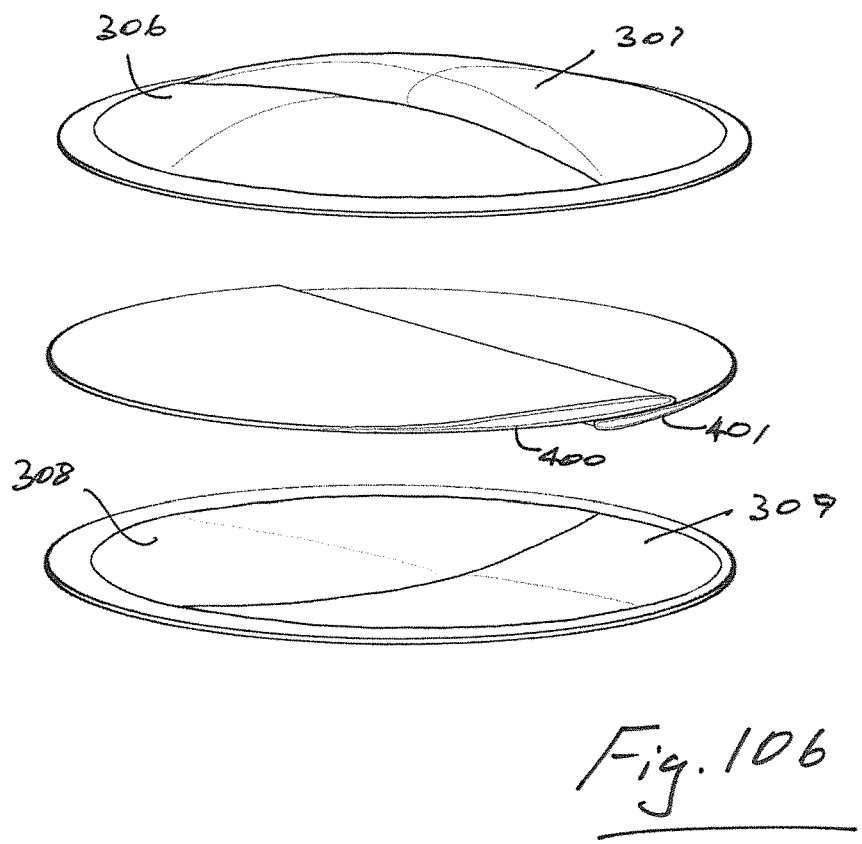

FIGS. 105 and 106 illustrates a hand access device which is similar to other embodiments incorporating a further valve such as an additional layer/lip seal/backup seal that reduces 'catastrophic' leak paths in extreme movements. In this case the additional valve layer comprises chambers 400, 401, similar to those of the inflatable valve. In this case the additional chambers 400, 401 do not inflate. They may be located at the bottom, top or in-between inflatable layers and may be overlapped or assembled with a gap. In one case the chambers 400, 401 are in same orientation as top layer but can be at any angle to the valve systems. The folded chamber-like configuration, though not inflated, provides a larger surface area for sealing and less risk of discomfort to the surgeon. This arrangement has no pre-defined sealing edge and therefore is more accommodating to an inserted arm/wrist of a surgeon.

Figure 107:
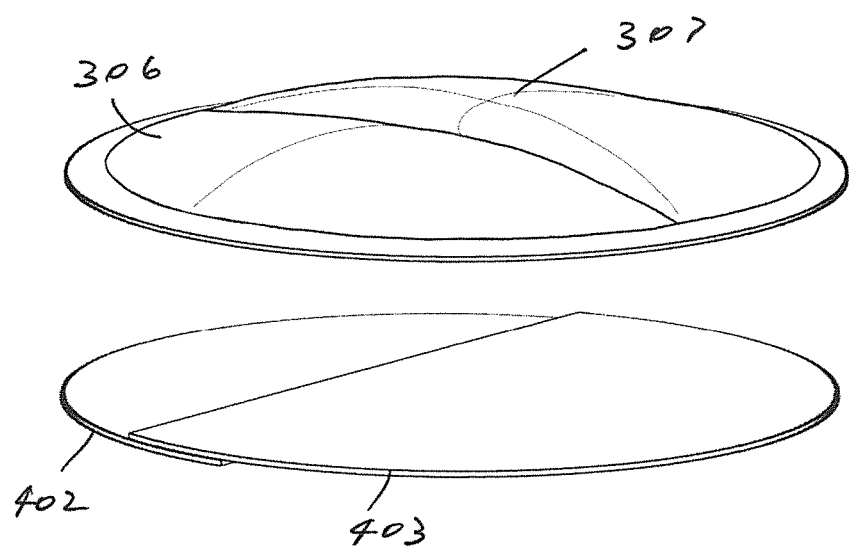

FIG. 107 is similar to FIGS. 105 and 106 except that the device has only one inflatable layer and one non-inflated backup seal layer 402, 403 which may be either non-inflated chambers or flat sheets as described above.

FIGS. 108 and 109(*a*) to 109(*d*) illustrate a secondary (instrument) valve 410 situated on the hand access device. Such a valve 410 functions as a zero seal and also a lip seal when an instrument inserted. There may be a multitude of such valves located around the primary inflatable valve. Various two-part assemblies that snap together/bond together while clamping down on the valve material are illustrated. The valves 410 may consist of a zero sealing duck bill valve or similar and/or a lip seal. The valve material can be bonded to the outside of the secondary valve or the material can be clamped between the two parts. Two parts can be snap fit, friction fit, bonded together or similar.

Figure 110A:
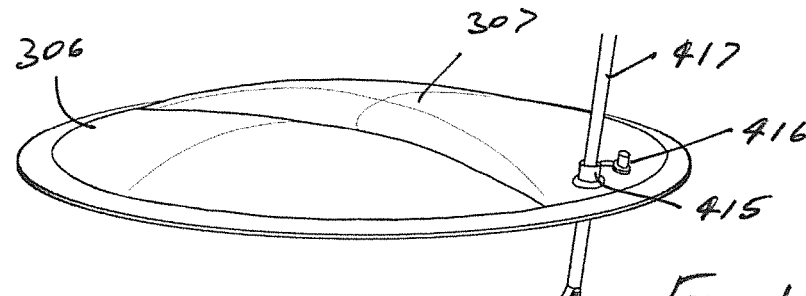
FIGS. 110(a) and 110(b) are perspective views of devices with a further secondary (instrument) valve.
Figure 110B:
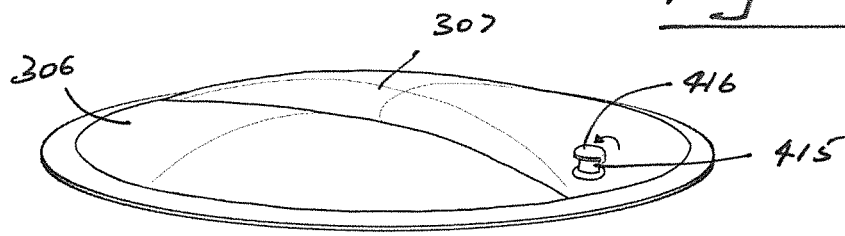

FIGS. 110(*a*) and 110(*b*) illustrate another secondary (instrument) valve 415 situated in any suitable location on the inflatable valve system that functions similar to the valve on a beach ball or an inflatable armband. The valve has a tethered cap 416 that serves as complete zero seal when in situ and when removed an instrument 417 can slide through the partial zero seal within while serving as a lip seal.

Figure 111A:
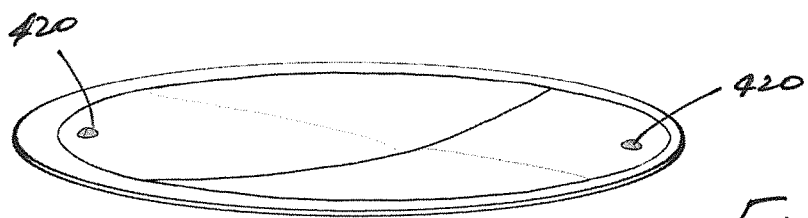
FIGS. 111(a) to 111(c) are views illustrating another secondary seal.
Figure 111B:
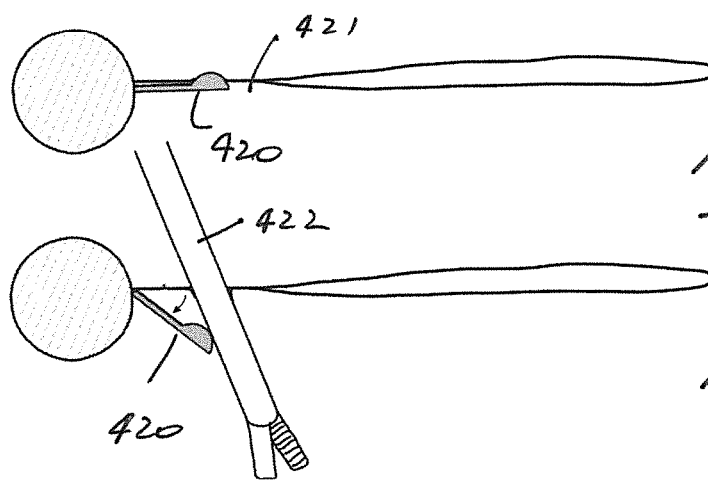
Figure 111C:
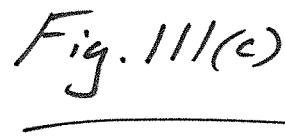

FIGS. 111(*a*) to 111(*c*) illustrates a hand access device that includes a secondary seal in which a pre-placed hole 421 in the valve is filled by a 'lever' type plug 420 that is hinged on the housing of the valve. The plug 420 is biased to a position (aided by back pressure during Pneumo) where it plugs the hole 421 effectively as a zero seal but is easily deflected by an instrument 422 when inserted. The hole 421 then serves as the lip seal for the valve itself. The hole/secondary valve may be located in a predetermined area where all layers of the primary inflatable valve have been locally heat sealed together to behave as one sheet of (thicker) film material rather that individual layers. The plug lever may also be on the upper side of hand access device.

FIGS. 112 to 115 illustrate a secondary seal in which a chute/tube valve 425 is attached to the top surface of the primary valve and fed through the leaves to appear on the bottom side of the primary valve. With no instrument in place the pressure in the inflated chambers along with the torturous path compresses the floppy tube to create a zero seal. When an instrument 426 is passed through, the chute/ tube 425 is forced to open to allow passage of the instrument 426 and serves as a competent lip seal. The chute/tube 425 may be tacked or bonded to the bottom layer also to prevent inversion.

FIGS. 116 and 117 shows a similar embodiment to FIGS. 112 to 115 in which a tube 430 itself has a shape memory effect/default position where it coils up on itself in order to create enough constriction to cause zero seal. Insertion of an instrument 426 causes the tube 430 to straighten out to allow passage with no significant obstruction. The tube 436 to serves as lip seal. The tubes/chutes described herein may be made from a number of materials.

FIGS. 118 to 120 illustrate an embodiment in which a region 450 of the primary valve is heat sealed together to form one uniform film material. In this case it is a circumferential (or partially circumferential) seal. In this case, the sealed region 450 is a defined area which the surgeon can puncture to gain access with an instrument 451 into the abdomen. In this case the material of the valve itself may function as a lip seal.

If the instrument 451 is removed a series of plugs 455 may be provided to act as a zero seal post-puncture as illustrated in FIGS. 121 to 123. In this embodiment the surgeon has the freedom to puncture anywhere in the predetermined area 450 to gain access and in a number of different positions, if required.

Figure 124:
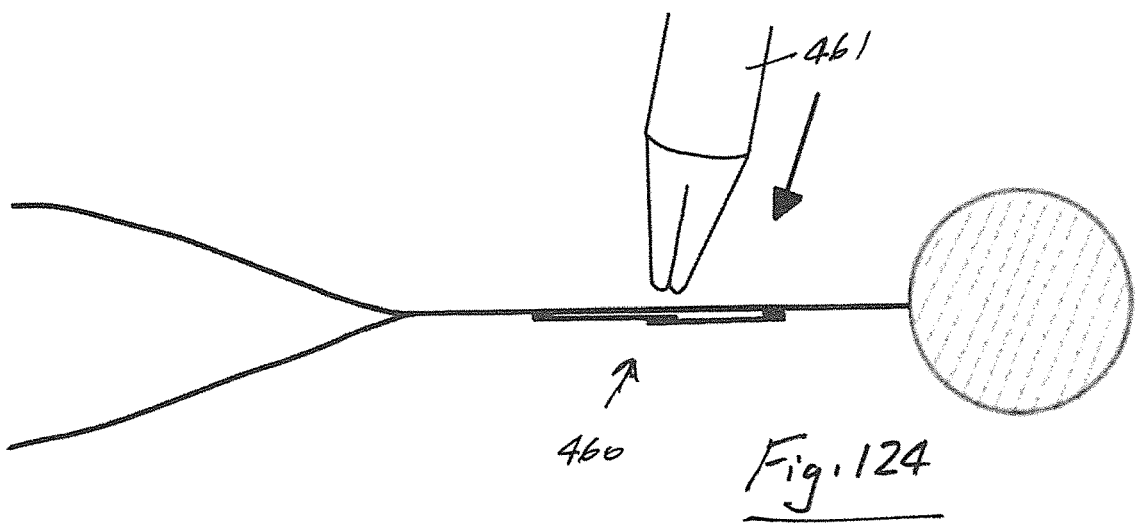
FIGS. 124 to 126 are views of another device of the invention with a sealing valve.
Figure 125:
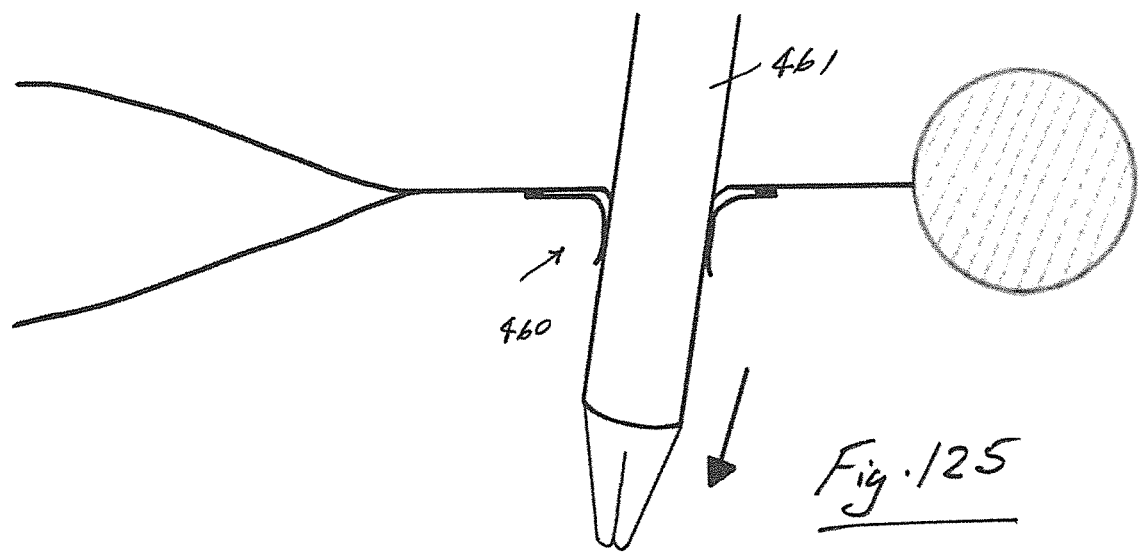
Figure 126:
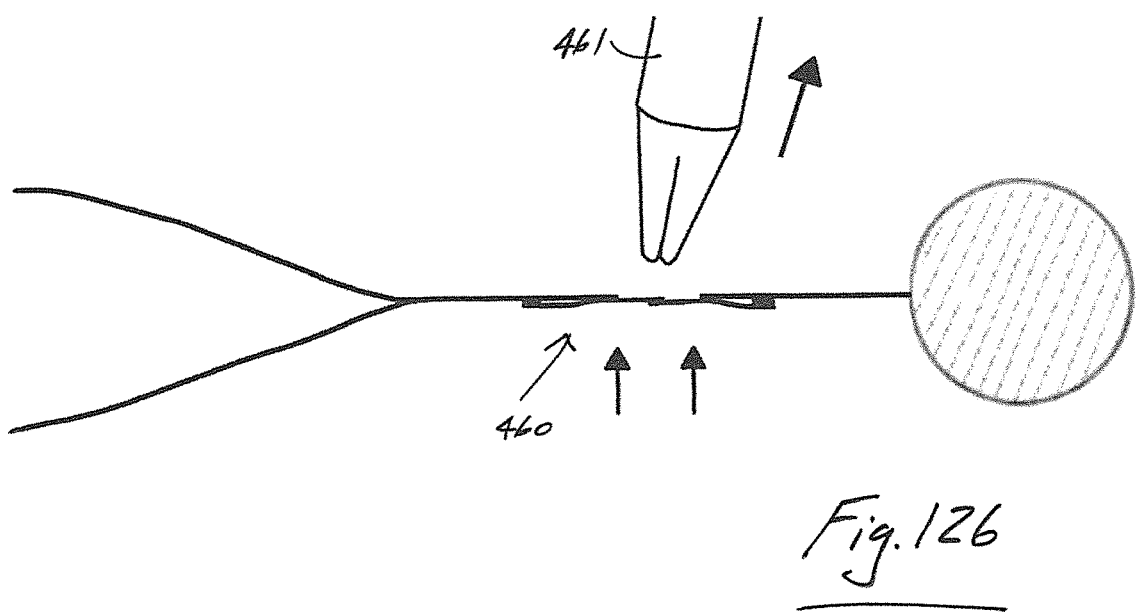

FIGS. 124 to 126 show a circumferential sealing 'flap' valve 460 on the underside of this puncture area. This flap (or multitude of overlapping flaps), biased in a sealing position and aided by back pressure during Pneumo, serves as a zero seal when an instrument is removed. These flaps and also the material of the chambers combine to function as a lip seal during use of an instrument 461.

FIGS. 127 and 128 show a similar embodiment of sealing with flaps 470 which may be either circumferential or localized. There may be per-determined holes 471 placed in the primary valve through which an instrument 472 may be inserted rather that than allowing the surgeon to puncture.

FIG. 129 is a view from the underside of a hand access device with one fully circumferential flap valve 480 (in grey), fixed to the inner diameter of the valve housing 481.

Figure 130:
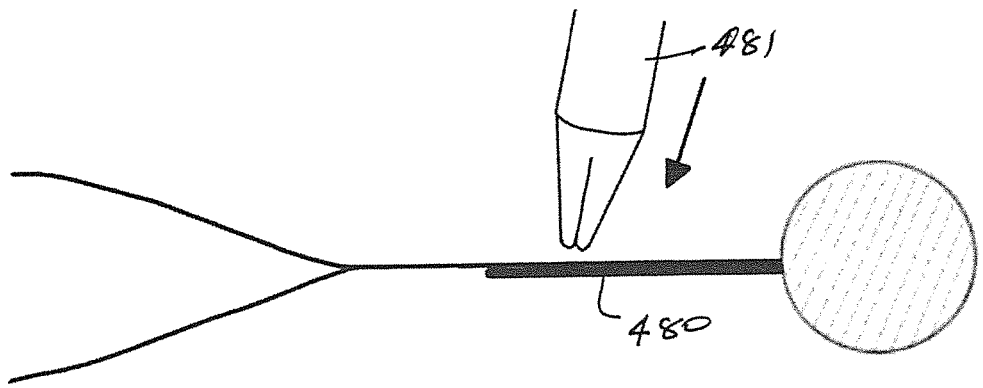
FIGS. 130 to 132 illustrate another device with a different flap seal arrangement.
Figure 131:
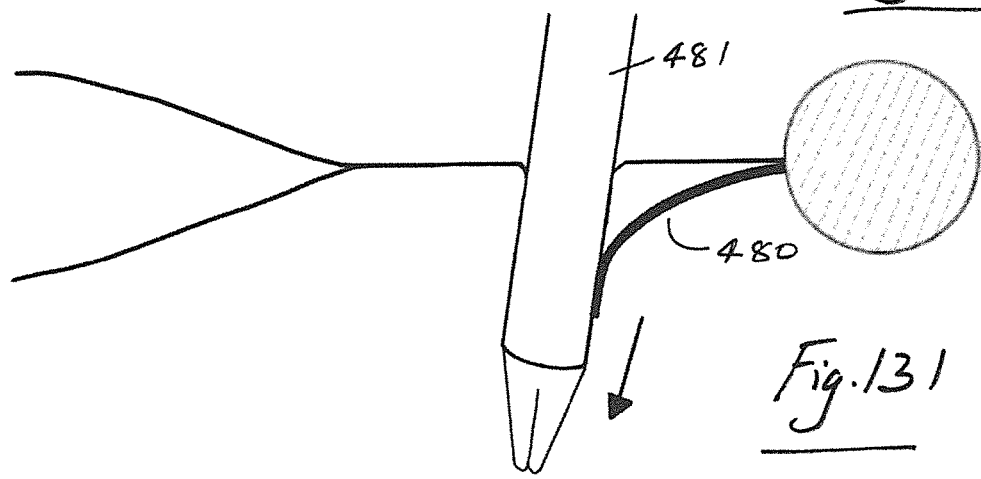
Figure 132:
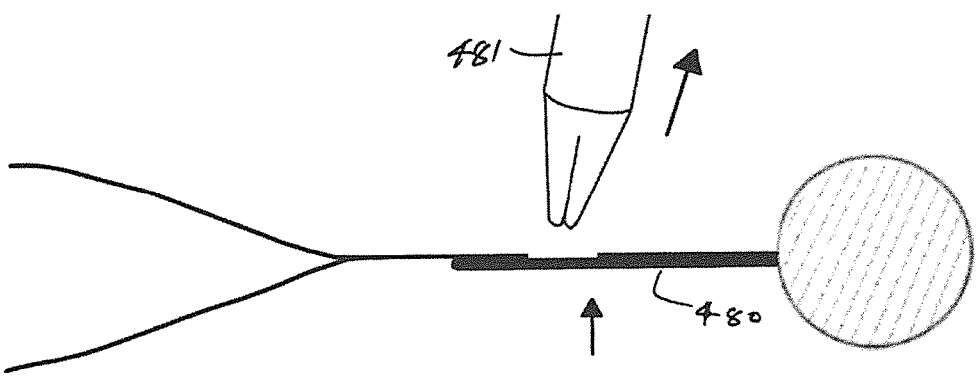

FIGS. 130 to 132 illustrate a single, fully circumferential flap seal 480 that overlaps a defined zone where the valve can be punctured. Once punctured by an instrument 481, the flap 480 is locally deflected to allow passage of the instrument, the material of the valve preforming as a lip seal. When the instrument 481 is removed the flap valve 480 readily returns to mate with the underside of the puncture site, with the aid of Pneumo back pressure, creating zero seal. The radial nature of the flap caters to the ability to puncture in any position circumferential to the primary valve.

Figure 133:
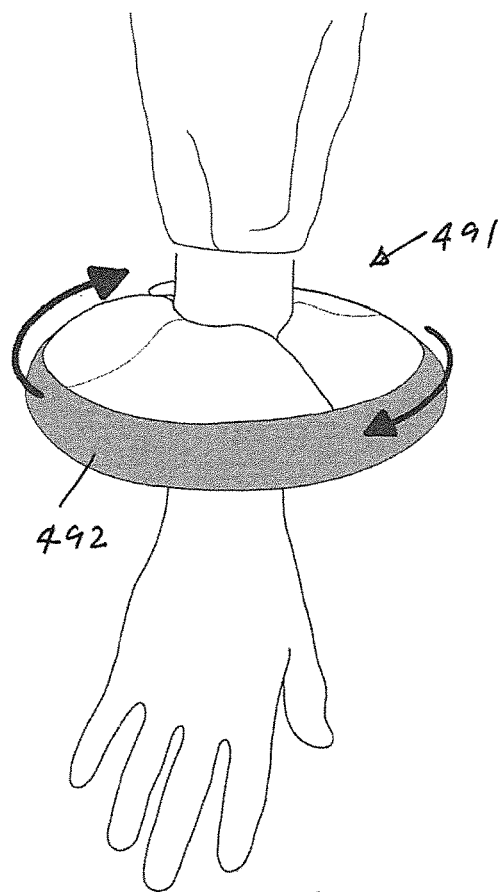
FIGS. 133 and 134 are isometric views that illustrate the ability of the device to rotate when in situ.
Figure 134:
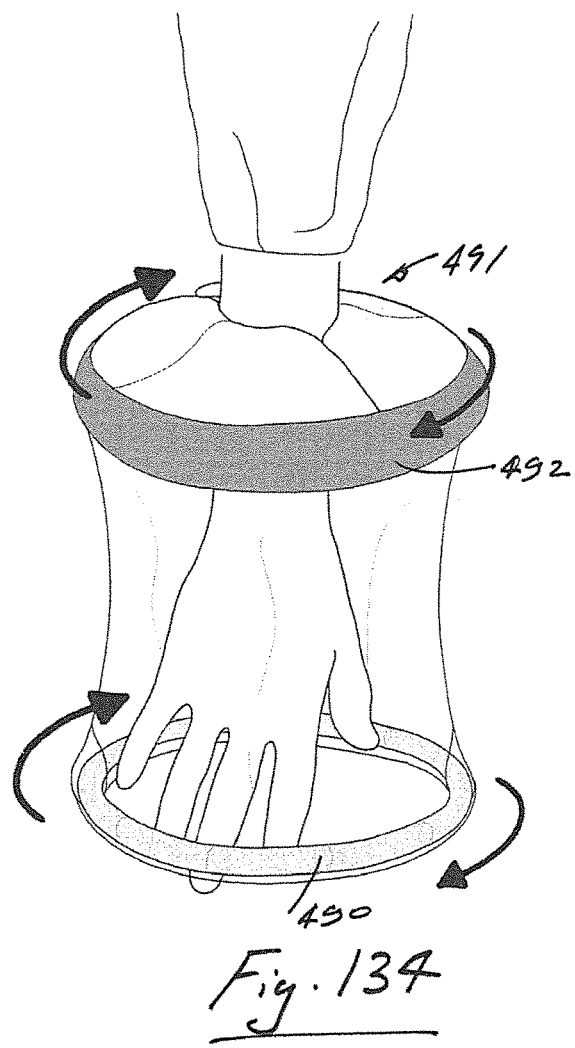

FIGS. 133 and 134 illustrate the ability of the hand access device 491 to spin freely in the wound of the patient during use to allow for preferred orientations. The illustrations show the device rotating with and without a distal ring 490. FIG. 134 shows the distal ring 490 rotating in tandem with the housing 492 and valve 491.

Figure 135:
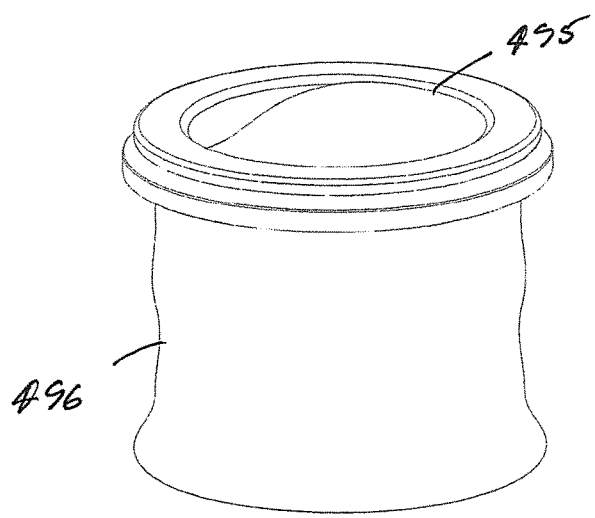
FIGS. 135 to 137 illustrate a method of attaching a valve and valve housing to a base retractor component.
Figure 136:
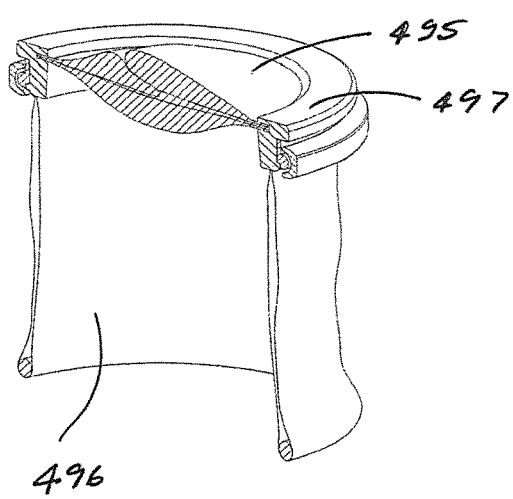
Figure 137:
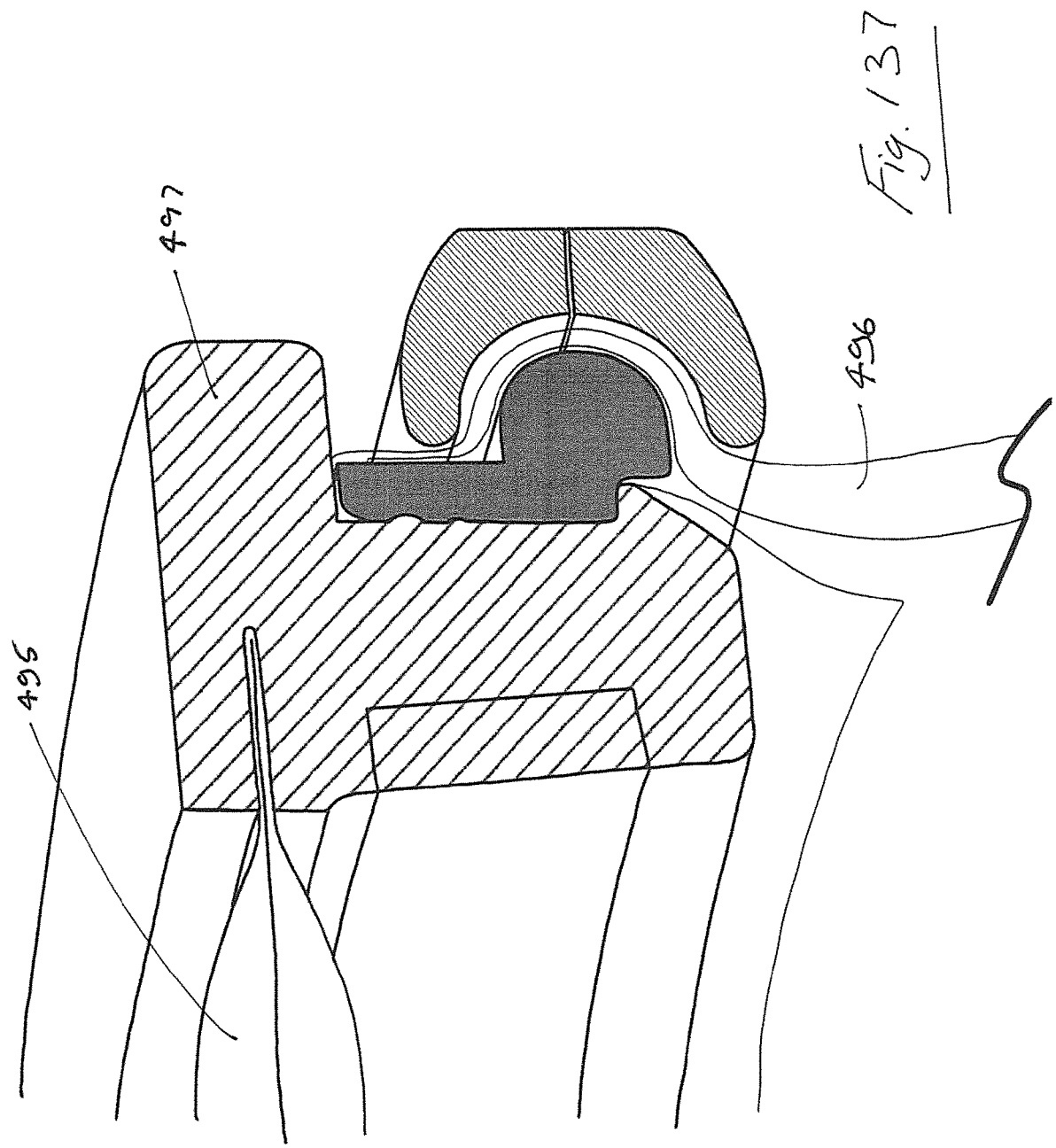

FIGS. 135 to 137 illustrate a method of attaching a hand access valve and valve housing to a base retractor 496. The hand access device housing 497 has a circumferential barb that hooks to features on the base retractor 496 in order to lock the retracted sleeve and lock to the base while sealing against abdominal pressure. The housing would have method of detachment in order to give leverage to the barb during removal. This could be a thumb tab, button, lever or design feature that allows simple removal of the valve system when required.

The invention is not limited to the embodiments hereinbefore described, which may be varied in construction and detail.

The invention claimed is:

1. A surgical access device comprising a plurality of chambers, the plurality of chambers having an uninflated configuration and an inflated configuration, the device comprising:
   a first group of inflatable chambers and a second group of inflatable chambers forming the plurality of chambers, the first group of inflatable chambers lying above the second group of inflatable chambers; and
   a port configured to one or more of inflate or deflate the plurality of chambers, wherein
   one inflatable chamber from the first group of inflatable chambers overlaps another inflatable chamber from the first group of inflatable chambers in a first region of overlap when the first group of inflatable chambers is in the uninflated configuration,
   one inflatable chamber from the second group of inflatable chambers overlaps another inflatable chamber from the second group of inflatable chambers in a second region of overlap when the second group of inflatable chambers is in the uninflated configuration, and
   the second region of overlap is offset from the first region of overlap,
   wherein the first group of inflatable chambers includes a curved shape extending away from the second group of inflatable chambers in the inflated configuration.

2. A device as claimed in claim 1, wherein the first region of overlap and the second region of overlap are offset by an angle of 5° to 175°, 10° to 170°, 15° to 165°, 20° to 160°, 25° to 155°, 30° to 150°, 35° to 145°, 40° to 140°, 45° to 135°, 50° to 130°, 55° to 125°, 60° to 120°, 65° to 115°, 70° to 110°, 75° to 105°, 80° to 100° or 85° to 95°.

3. A device as claimed in claim 1, wherein the first region of overlap and the second region of overlap are offset by about 90°.

4. A device as claimed in claim 1, wherein at least one of the first region of overlap and the second region of overlap extends laterally for a distance between 5 mm and 50 mm, from 10 mm to 45 mm, or from 20 mm to 40 mm.

5. A device as claimed in claim 1, further comprising an additional sealing member.

6. A device as claimed in claim 5, wherein the additional sealing member is located between the first group of inflatable chambers and the second group of inflatable chambers.

7. A device as claimed in claim 5, wherein the additional sealing member comprises a lip seal valve.

8. The surgical access device according to claim 5, wherein the additional sealing member is non-inflatable.

9. A surgical access device as claimed in claim 1, wherein the device includes a longitudinal axis and the first group of inflatable chambers and the second group of inflatable chambers extend laterally from the longitudinal axis.

10. A surgical access device as claimed in claim 1, wherein the device includes a longitudinal axis and the first region of overlap and the second region of overlap extend generally transverse to the longitudinal axis.

11. A surgical access device comprising a plurality of chambers, the plurality of chambers having an uninflated configuration and an inflated configuration, the device comprising:

a first group of inflatable bicuspid chambers and a second group of inflatable bicuspid chambers forming the plurality of chambers, the first group of inflatable bicuspid chambers lying above the second group of inflatable bicuspid chambers; and an intermediate sealing member positioned between the first group of inflatable bicuspid chambers and the second group of inflatable bicuspid chambers, wherein the intermediate sealing member is the only layer between the first group of inflatable bicuspid chambers and the second group of inflatable bicuspid chambers, wherein at least one of the first group of inflatable bicuspid chambers or the second group of inflatable bicuspid chambers includes a dome shape extending away from the intermediate sealing member in the inflated configuration.

12. The device according to claim 11, wherein one inflatable chamber from the first group of inflatable bicuspid chambers overlaps another inflatable chamber from the first group of inflatable bicuspid chambers in a first region of overlap when the first group of inflatable bicuspid chambers is in the uninflated configuration, one inflatable chamber from the second group of inflatable bicuspid chambers overlaps another inflatable chamber from the second group of inflatable bicuspid chambers in a second region of overlap when the second group of inflatable bicuspid chambers is in the uninflated configuration, and the second region of overlap is offset from the first region of overlap.

13. The device according to claim 11, further comprising a port configured to one or more of inflate or deflate the plurality of chambers.

14. The device according to claim 11, wherein the intermediate sealing member is non-inflatable.

15. The device according to claim 14, wherein the intermediate sealing member includes a lip seal valve.

16. A surgical access device comprising a plurality of chambers, the plurality of chambers having an uninflated configuration and an inflated configuration, the device comprising:

a first group of inflatable bicuspid chambers from the plurality of chambers, wherein the first group of bicuspid chambers are configured to sealingly abut at a first seal; and a second group of inflatable bicuspid chambers from the plurality of chambers, wherein the second group of bicuspid chambers are configured to sealingly abut at a second seal, wherein the first group of inflatable bicuspid chambers lie above the second group of inflatable bicuspid chambers and share a central longitudinal axis, and wherein the first seal and the second seal are rotatingly offset about the central longitudinal axis, and wherein at least one of the first group of inflatable bicuspid chambers or the second group of inflatable bicuspid chambers includes a curved shape extending away from the other of the first group of inflatable bicuspid chambers or the second group of inflatable bicuspid chambers in the inflated configuration.

17. The device according to claim 16, further comprising a non-inflatable sealing member.

18. The device according to claim 17, wherein the second group of inflatable bicuspid chambers is disposed between the first group of inflatable bicuspid chambers and the non-inflatable sealing member.

* * * * *